United States Patent [19]

Katoh

[11] Patent Number: 5,711,148
[45] Date of Patent: Jan. 27, 1998

[54] SENSOR ARRANGEMENT FOR ENGINE CONTROL SYSTEM

[75] Inventor: Masahiki Katoh, Hamamatsu, Japan

[73] Assignee: Sanshin Kogyo Kabushiki Kaisha, Hamamatsu, Japan

[21] Appl. No.: 435,715

[22] Filed: May 5, 1995

[30] Foreign Application Priority Data

| Jun. 5, 1994 | [JP] | Japan | 6-117645 |
| Jun. 30, 1994 | [JP] | Japan | 6-173625 |
| Jul. 13, 1994 | [JP] | Japan | 6-185418 |
| Jul. 13, 1994 | [JP] | Japan | 6-185419 |

[51] Int. Cl.$^6$ ..................... F01N 3/18
[52] U.S. Cl. ..................... 60/276; 123/703
[58] Field of Search ..................... 60/276; 123/703, 123/674, 672

[56] References Cited

U.S. PATENT DOCUMENTS

| 4,617,796 | 10/1986 | Abthoff | 60/276 |
| 4,831,820 | 5/1989 | Lassanske | |
| 4,903,648 | 2/1990 | Lasaanske | |
| 5,236,330 | 8/1993 | Buchheister | 60/276 |

*Primary Examiner*—Douglas Hart
*Attorney, Agent, or Firm*—Knobbe, Martens, Olson & Bear LLP

[57] ABSTRACT

A number of embodiments of feedback control systems for two-cycle, internal combustion engine management systems. Each embodiment employs an exhaust system sensor which senses the exhaust gases by drawing exhaust gases from the exhaust of the engine. In some instances this is done directly from the cylinder and in others it is done in the exhaust system. In each embodiment, the sensor is provided in an accumulator chamber so as to provide an accurate signal of instantaneous engine running conditions. The use of the accumulator chamber insures that the combustible gases will not be diluted with fresh air charge, but will be able to purge from cycle to cycle so as to provide cycle-by-cycle information. Various arrangements are provided for protecting the sensor including serpentine flow paths, shields, the direction in which the exhaust gases are delivered and combinations of these features.

88 Claims, 44 Drawing Sheets

SENSOR ARRANGEMENT FOR ENGINE CONTROL SYSTEM

BACKGROUND OF THE INVENTION

This invention relates to an engine control system and more particularly an improved sensor arrangement for such a system as particularly applied to two-cycle crankcase compression internal combustion engines.

The advantages to two-cycle internal combustion engines because of their simplicity and relatively low cost are well noted. However, the porting arrangement for these engines gives rise to certain problems in connection with exhaust emission control. Because of the overlap between the scavenging action and the exhaust, there is some difficulty in insuring good exhaust emission control. This is because some of the scavenging charge may actually pass out the exhaust port, and thus present the risk of unburned hydrocarbons escaping to the atmosphere.

In addition to this problems, because of the fact that the lubricant in a two-cycle engine is normally not recirculated but is consumed in the engine during its running, there is a likelihood of lubricant in the exhaust gases. Thus, this type of engine presents particular problems in controlling exhaust gas emissions.

Such features as the use of fuel injection and exhaust gas treatment as well as feedback controls have been proposed so as to permit the continued use of two-cycle engines, even in spite of environmental concerns. However, the use of some of these exhaust control methods also are made difficult by the inherent nature of the two-cycle engine operation.

For example, it has been the practice in four-cycle engines to use feedback control systems to maintain the desired air/fuel ratio under all running conditions. These feedback control systems employ oxygen sensors in the exhaust or other sensors to insure that the air/fuel ratio is maintained within the desired range and also to control exhaust emissions. The most commonly used type of sensor senses the presence of oxygen in the exhaust gases in order to provide an indication as to whether or not a stoichiometric mixture is being burned. However, due to the scavenging effect and the likelihood of some air charge in the exhaust gases, oxygen sensors may not be completely practical in these applications. This is that the oxygen sensor may receive some oxygen rather than exhaust gases during the final portions of the exhaust scavenged phase. Devices have been proposed for attempting to overcome these problems, but for a variety of reasons they have not been particularly successful.

It is, therefore, a principal object of this invention to provide an improved engine management system particularly adapted for use with two-cycle crankcase compression engines.

It is a further object of this invention to provide an improved sensor arrangement for feedback control in such engine management systems.

It is a still further object of this invention to provide an improved exhaust sensor arrangement for a two-cycle crankcase compression engine wherein the sensor is mounted and operated in such a way as to insure that primarily exhaust products will be delivered to the sensor.

In order to permit more accurate exhaust gas sensing in two-cycle engines, it has been proposed to provide an oxygen sensor arrangement wherein the oxygen sensor receives gases directly from the combustion chamber but only at times when the scavenging process is not at such a stage where the scavenge gases may contact the oxygen sensor. However, the type systems proposed for this purpose have, for the most part, required some form of valving arrangement for insuring that the oxygen sensor only receives exhaust gases. This provides not only a complicated structure, but also a possible source for malfunction.

It is, therefore, a still further object of this invention to provide an improved oxygen sensor arrangement for two-cycle engines wherein it can be insured that the sensor receives exhaust products from the engine but not scavenging gas products.

As has been previously noted, the exhaust gases in two-cycle engines may contain amounts of lubricant. The type of exhaust sensors utilized for engine management systems are relatively sensitive and can be easily contaminated if lubricant comes in contact with them.

It is, therefore, a still further object of this invention to provide an improved exhaust sensor arrangement for an engine wherein the sensor, per se, is protected from contamination.

SUMMARY OF THE INVENTION

A first feature of this invention is adapted to be embodied in a control system for an internal combustion engine having a combustion chamber that varies in volume cyclically during engine operation. An exhaust system receives exhaust gases from the combustion chamber during a cycle of engine operation. A fuel supply system is provided for supplying fuel to the engine for combustion in the combustion chamber. An accumulator chamber is provided that affords a volume in which exhaust gases from the combustion chamber may be accumulated and communicates with combustion chamber for at least a portion of the engine operating cycle. A sensor is provided in the accumulator chamber and displaces less than one-half of the volume of the accumulator chamber for providing a control signal for control of the fuel supply system.

Another feature of the invention is adapted to be embodied in a control system for a ported engine having at least two combustion chambers, each of which cyclically vary in volume during a single cycle of operation. An accumulator chamber containing an exhaust sensor for sensing the condition of the exhaust gases is provided. This exhaust sensor provides a signal for controlling a fuel supply system that supplies fuel to the combustion chamber for combustion therein. Communicating means communicate the accumulator chamber with at least two of the combustion chambers and controls the flow therethrough so that exhaust gases from only one of the combustion chambers enters the accumulator chamber.

A still further feature of the invention is adapted to be embodied in a control system for a two-cycle internal combustion engine having a combustion chamber that varies cyclically during engine operation. An exhaust system receives exhaust gases from the combustion chamber during a cycle of engine operation. A fuel supply system supplies fuel to the engine for combustion in the combustion chamber. An accumulator chamber provides a volume in which exhaust gases from the combustion chamber may accumulate and communicates with the combustion chamber for at least a portion of the engine operating cycle. A sensor is provided in the accumulator chamber for providing a control signal for control of the fuel supply system. Means prevent oil in the exhaust gases from contaminating the sensor.

DETAILED DESCRIPTION OF THE PREFERRED EMBODIMENTS OF THE INVENTION

Figure 1:
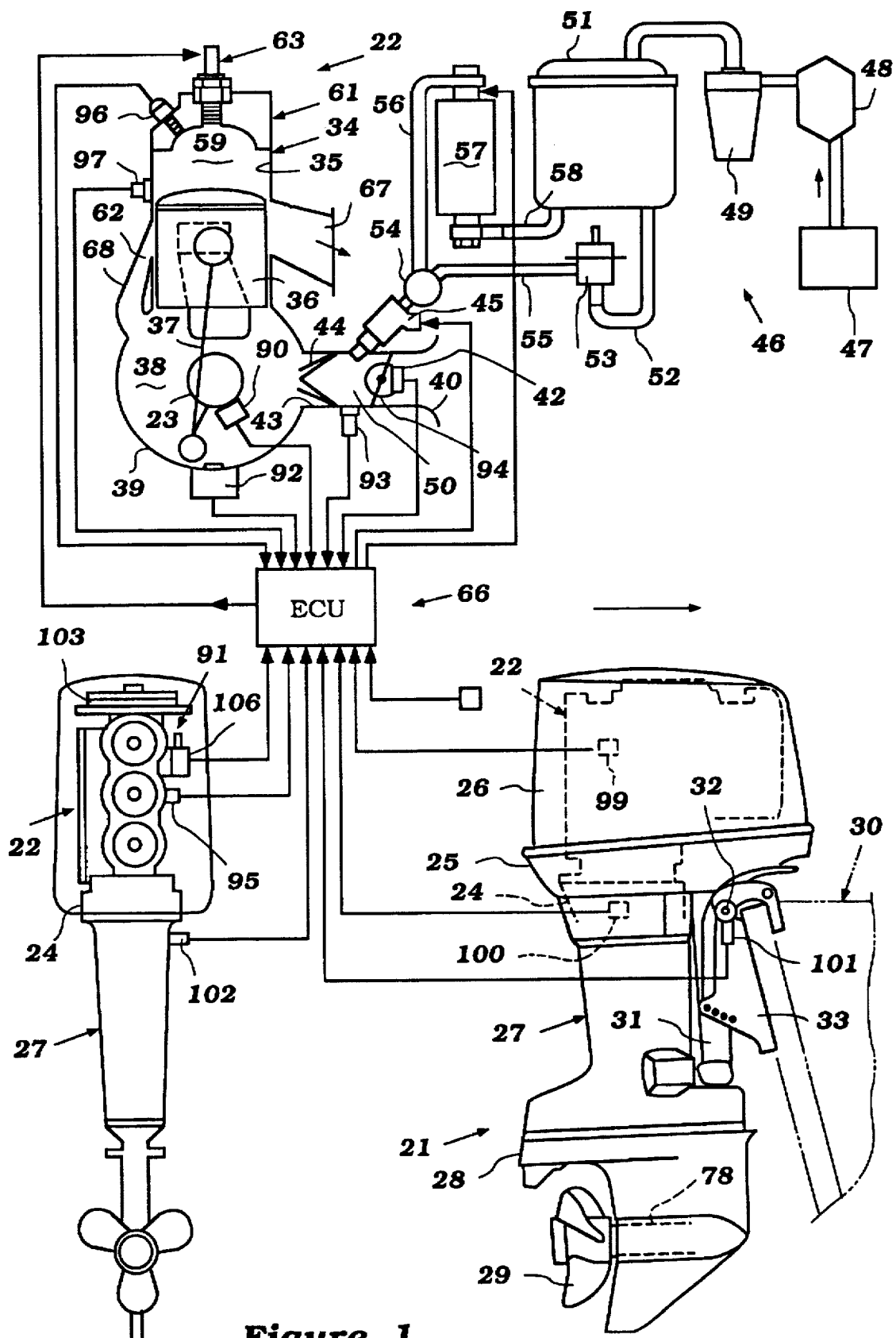
FIG. 1 is a partially schematic view showing an outboard motor constructed in accordance with an embodiment of the invention in side elevation, in rear plan with a portion of the protective cowling removed and in a schematic cross-sectional view, taken through one cylinder of the engine with the fuel supply system and feedback control system being shown in part schematically.
Figure 2:
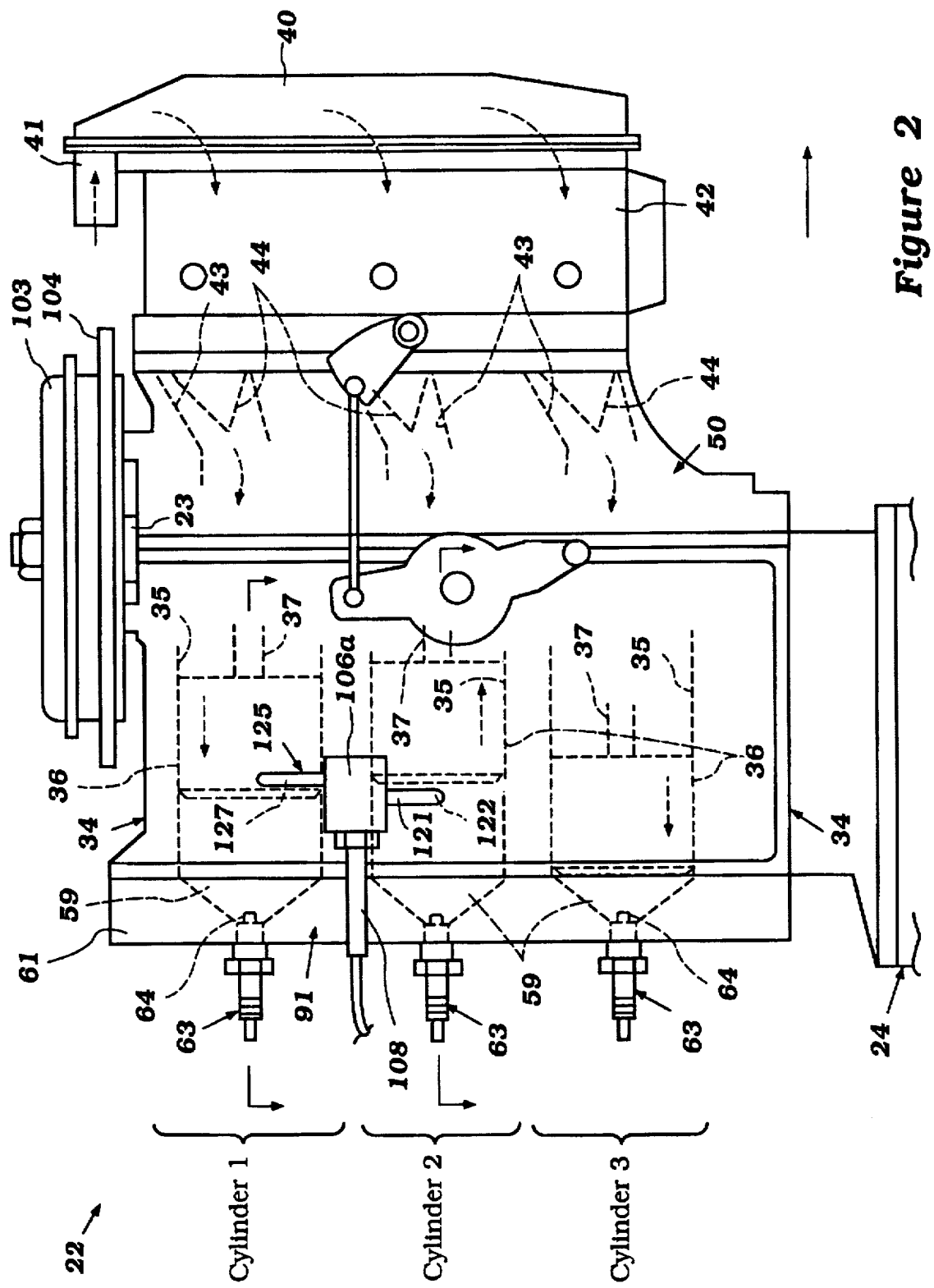
FIG. 2 is an enlarged side elevational view of the engine in the power head and looking in the same direction as the lower right-hand side view of FIG. 1.

Referring now in detail to the drawings, and to the embodiment of FIGS. 1–10 initially by reference to FIG. 1, an outboard motor is shown in the lower portion of this figure in rear and side elevation and is indicated generally by the reference numeral 210 The invention is shown in conjunction with an outboard motor because the invention has particular utility in conjunction with two-cycle crankcase compression engines. Such engines are normally used as the propulsion device for outboard motors. For these reasons, the full details of the outboard motor 21 will not be described and have not been illustrated. Those skilled in the art can readily understand how the invention can be utilized with any known type of outboard motor.

The outboard motor 21 includes a power head that is comprised of a powering internal combustion engine, indicated generally by the reference numeral 22. The engine 22 is shown in the lower left-hand portion of FIG. 3 and in the lower view of FIG. 1, with a portion broken away, and in a schematic cross-sectional view through a single cylinder in the upper view of this figure. The construction of the engine 22 will be described later, but it should be noted that the engine 22 is mounted in the power head so that its crankshaft, indicated by the reference numeral 23, rotates about a vertically extending axis. The engine 22 is mounted on a guide plate 24 provided at the lower end of the power head and the upper end of a drive shaft housing, to be described. Finally, the power head is completed by a protective cowling comprised of a lower tray portion 25 and a detachable upper main cowling portion 26.

The engine crankshaft 23 is coupled to a drive shaft (not shown) that depends into and is rotatably journalled within the aforenoted drive shaft housing which is indicated by the reference numeral 27. This drive shaft then continues on to drive a forward/neutral/reverse transmission, which is not shown but which is contained within a lower unit 28. This transmission provides final drive to a propeller 29 in any known manner for propelling an associated watercraft.

A steering shaft (not shown) is affixed to the drive shaft housing 27. This steering shaft is journalled for steering movement within a swivel bracket 31 for steering of the outboard motor 21 and the associated watercraft shown in phantom and indicated generally by the reference numeral 30 in a well-known manner.

The swivel bracket 31 is, in turn, pivotally connected by a pivot pin 32 to a clamping bracket 33. The clamping bracket 33 is adapted to be detachably affixed to the transom of the associated watercraft 30. The pivotal movement about the pivot pin 32 accommodates trim and tilt-up operation of the outboard motor 21, as is well known in this art.

Continuing to refer to FIG. 1 and now primarily to the lower left-hand side view and the upper view, the engine 22 is depicted as being of the two-cycle crankcase compression type and, in the specific illustrated embodiment, is of a three-cylinder in-line configuration. Although this particular cylinder configuration is illustrated, it will be apparent to those skilled in the art how the invention may be employed with engines having other numbers of cylinders and other cylinder orientations. In fact, certain facets of the invention may also be employed with rotary or other ported type engines.

The engine 22 includes a cylinder block 34 in which three cylinder bores 35 are formed. Pistons 36 reciprocate in these cylinder bores 35 and are connected by means of connecting rods 37 to the crankshaft 23. The crankshaft 23 is, in turn, journalled for rotation within a crankcase chamber 38 in a suitable manner. The crankcase chamber 38 is formed by the cylinder block 34 and a crankcase member 39 that is affixed to it in any known manner.

As is typical with two-cycle crankcase compression engine practice, the crankcase chambers 38 associated with each of the cylinder bores 35 are sealed relative to each other in an appropriate manner. A fuel-air charge is delivered to each of the crankcase chambers 28 by an induction system which is comprised of an atmospheric air inlet device 40 (see also FIGS. 2 and 3) which draws atmospheric air through an inlet 41 from within the protective cowling. This air is admitted to the protective cowling in any suitable manner.

A throttle body assembly 42 is positioned in an intake manifold 50 downstream of the air inlet 41 and is operated in any known manner. Finally, the intake system discharges into intake ports 43 formed in the crankcase member 39. Reed-type check valves 44 are provided in each intake port 43 for permitting the charge to be admitted to the crankcase chambers 38 when the pistons 36 are moving upwardly in the cylinder bore 35. These reed-type check valves 44 close when the piston 36 moves downwardly to compress the charge in the crankcase chambers 38, as is also well known in this art.

Fuel is added to the air charge inducted into the crankcase chambers 38 by a suitable charge former. In the illustrated embodiments, this charge former includes fuel injectors 45, each mounted in a respective branch of the intake manifold downstream of the respective throttle valve 42. The fuel injectors 45 are preferably of the electronically operated type. That is, they are provided with an electric solenoid that operates an injector valve so as to open and close and deliver high-pressure fuel directed toward the intake port 43.

Fuel is supplied to the fuel injectors 45 under high pressure through a fuel supply system, indicated generally by the reference numeral 46. This fuel supply system 46 includes a fuel tank 47 which is positioned remotely from the outboard motor 21 and preferably within the hull of the watercraft 30 propelled by the outboard motor 21. Fuel is pumped from the fuel tank 47 by means of a fuel pump 48, which may be electrically or otherwise operated. This fuel then passes through a fuel filter 49, which preferably is mounted within the power head of the outboard motor 21. Fuel flows from the fuel filter 49 through a conduit into a fuel vapor separator 51, which includes a float controlled valve for controlling the level of fuel in the fuel vapor separator 51. Any accumulated vapor will condense, and excess vapor pressure can be relieved through a suitable vent (not shown).

Also mounted, preferably in the power head, is a high-pressure fuel pump 53 which is driven in any known manner as by an electric motor or directly from the engine 22. This fuel pump 53 draws fuel from the fuel vapor separator 51 through a conduit 52 and delivers fuel under high pressure to a fuel rail 54 through a conduit 55. The fuel rail 54 serves each of the injectors 45 associated with the engine.

A return conduit 56 extends from the fuel rail 54 to a pressure regulator 57. The pressure regulator 57 controls the maximum pressure in the fuel rail 54 that is supplied to the fuel injectors 45. This is done by dumping excess fuel back to the fuel vapor separator 51 through a return line 58. The regulated pressure may be adjusted electrically along with other controls, as will be described.

The fuel-air charge which is formed by the charge-forming and induction system as thus far described is transferred from the crankcase chambers 38 to combustion chambers, indicated generally by the reference numeral 59, of the engine. These combustion chambers 59 are formed by the heads of the pistons 36, the cylinder bores 35, and a cylinder head assembly 61 that is affixed to the cylinder block 34 in any known manner. The charge so formed is transferred to the combustion chamber 59 from the crankcase chambers 38 through one or more scavenge passages 62.

Spark plugs 63 are mounted in the cylinder head 61 and have their spark gaps 64 extending into the combustion chambers 59. The spark plugs 63 are fired by a capacitor discharge ignition system (not shown). This outputs a signal to a spark coil which may be mounted on each spark plug 63 for firing the spark plug 63 in a known manner.

The capacitor discharge ignition circuit is operated, along with certain other engine controls such as the regulated fuel pressure, by an engine management ECU, shown schematically and identified generally by the reference numeral 66.

When the spark plugs 63 fire, the charge in the combustion chambers 59 will ignite and expand so as to drive the pistons 36 downwardly. The combustion products are then discharged through exhaust ports 67 formed in the cylinder block 34. These exhaust gases then flow through an exhaust manifold, shown in FIG. 4 and identified by the reference numeral 68. The exhaust gases then pass downwardly through an opening in the guide plate 24 to an appropriate exhaust system (to be described later) for discharge of the exhaust gases to the atmosphere. Conventionally, the exhaust gases are discharged through a high-speed under-the-water discharge and a low-speed, above-the-water discharge. The systems may be of any type known in the art.

The engine 22 is water cooled, and for this reason, the cylinder block 34 is formed with a cooling jacket 69 to which water is delivered from the body of water in which the watercraft is operating. Normally, this coolant is drawn in through the lower unit 28 by a water pump positioned at the interface between the lower unit 28 and the drive shaft housing 27 and driven by the drive shaft. This coolant also circulates through a cooling jacket formed in the cylinder head 61. After the water has been circulated through the engine cooling jackets, it is dumped back into the body of water in which the watercraft is operating. This is done in any known manner and may involve the mixing of the coolant with the engine exhaust gases to assist in their silencing. This will also be described later.

Figure 3:
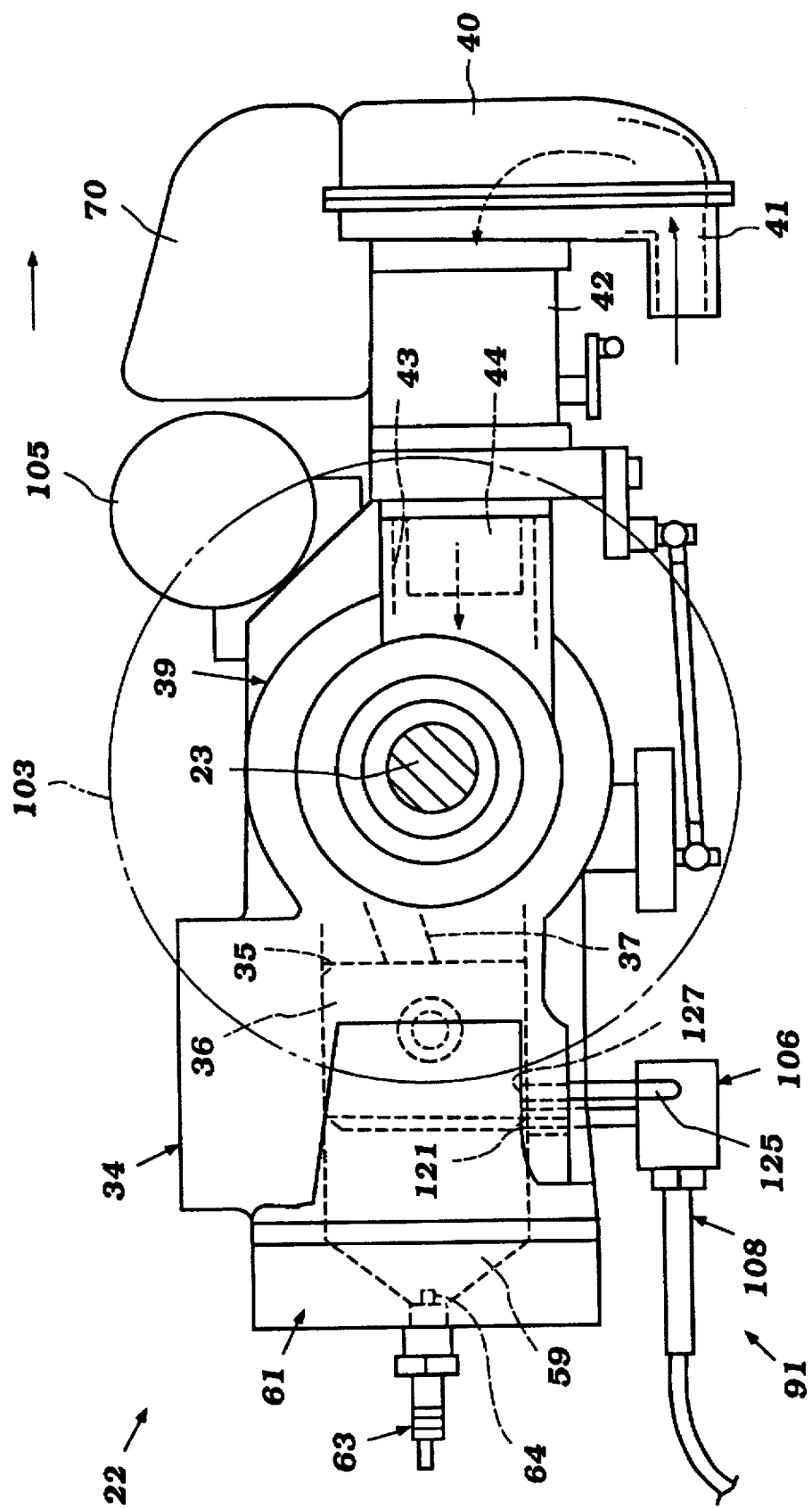
FIG. 3 is a top plan view of the engine as depicted in FIG. 2.

Although not completely shown in the drawings, the engine 22 is also provided with a lubricating system for lubricating the various moving components of the engine 22. This system may spray fuel into the intake passages in proximity to the fuel injector nozzles 45 and/or may deliver lubricant directly to the sliding surfaces of the engine 22. This lubricant is supplied from a tank 70 mounted adjacent the air inlet device 40 (FIG. 3).

Figure 4:
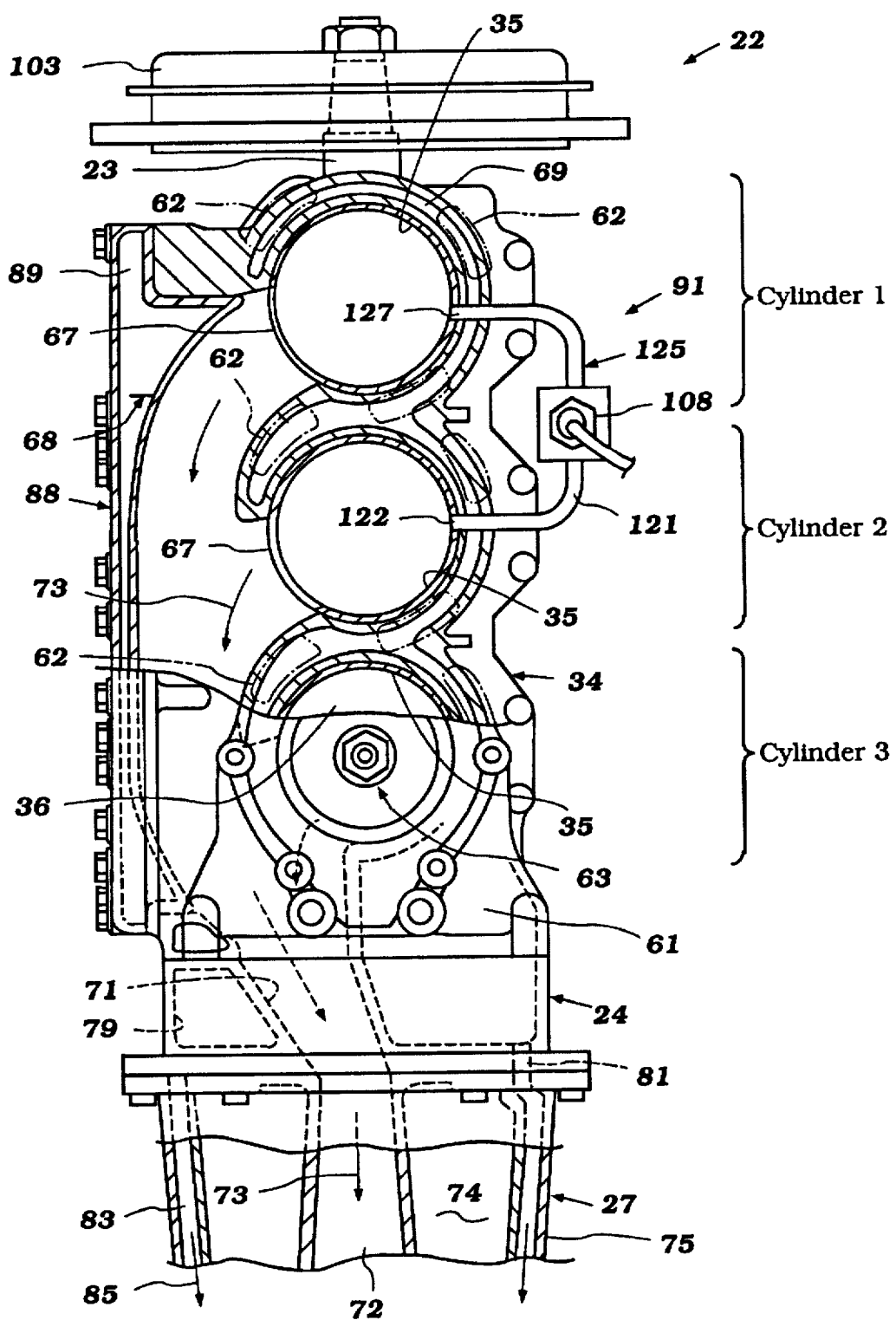
FIG. 4 is a view taken in the same direction as the rear elevational view of FIG. 1 on an enlarged scale and with portions of the engine broken away to more clearly show the construction.
Figure 5:
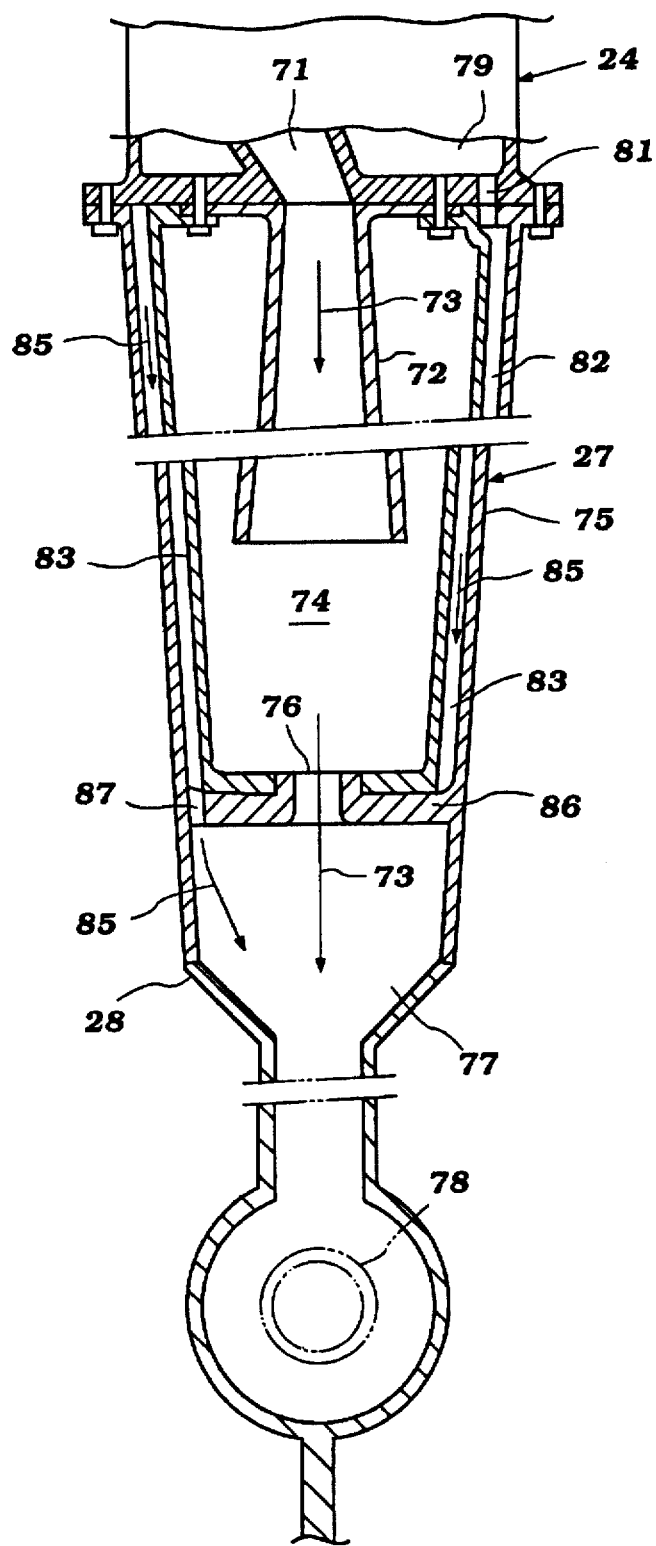
FIG. 5 is a view, in part similar to FIG. 4, and shows the portion of the outboard motor below the power head, and thus forms in part a continuation of FIG. 4 with a further part broken away and shown in section.

Referring now primarily to FIGS. 4 and 5, the exhaust system for discharging the exhaust gases to the atmosphere will be described. As has been noted, the exhaust manifold 68 communicates with an exhaust passage, indicated by the reference numeral 71, that is formed in the spacer or guide plate 24. An exhaust pipe 72 is affixed to the lower end of the guide plate 24 and receives the exhaust gases from the passage 71, as shown by the arrows 73.

The exhaust pipe 72 depends into an expansion chamber 74 formed within the outer shell 75 of the drive shaft housing 27. This expansion chamber 74 is defined by an inner member which has a lower discharge opening 76 that communicates with an exhaust chamber 77 formed in the lower unit 28 and to which the exhaust gases flow.

A through-the-hub, high speed, exhaust gas discharge opening 78 is formed in the hub of the propeller 29 and the exhaust gases exit the outboard motor 22 through this opening below the level of water in which the watercraft 30 is operating when traveling at high speeds. In addition to this high speed exhaust gas discharge, the outboard motor 21 may be provided with a further above-the-water, low speed, exhaust gas discharge (not shown). As is well know in this art, this above-the-water exhaust gas discharge is relatively restricted, but permits the exhaust gases to exit without significant back pressure when the watercraft 30 is traveling at a low rate of speed or is idling, and the through-the-hub exhaust gas discharge 78 will be deeply submerged.

As has been previously noted, the cooling water from the engine cooling jacket 69 may also be mixed with the exhaust gases. To accomplish this, the guide plate 24 is provided with a cooling jacket 79 which extends around the exhaust passage 71 and into which the spent cooling water from the engine 22 is returned. This water is then drained through one or more drain openings 81 formed in the lower surface of the guide plate 24. These openings 81 communicate with a water jacket 82 which is formed in the space 83 existent between the outer shell of the expansion chamber 74 and the inner surface of the drive shaft housing outer shell 75. This water flows in the direction of the arrows 85.

Finally, a horizontally extending wall 86 formed at a lower portion of the drive shaft housing 27 is provided with one or more water discharge openings 87. The water flows through these openings 87, as also indicated by the arrows 85, so as to mix with the exhaust gas flow 73 and be discharged back into the body of water in which the watercraft is operating.

Thus, the existence of the cooling jacket 83 around the expansion chamber 74 provides silencing and cooling. If desired, a cooling jacket may also be formed around the exhaust manifold 68, and this cooling jacket is formed, as shown primarily in FIG. 4, by a cover plate 88 that is affixed to the side of the cylinder block 34 and which defines a cooling jacket 89, as well as a portion of the exhaust manifold 68. Coolant is delivered to this cooling jacket 89 from the engine cooling jacket 69 in an appropriate manner. This water is also then discharged to the guide plate cooling jacket 79.

It has been noted that the ECU 66 controls the capacitor discharge ignition circuit and the firing of the spark plugs 63. In addition, the ECU controls the fuel injectors 45 so as to control both the beginning and duration of fuel injection and the regulated fuel pressure, as already noted. The ECU 66 may operate on any known strategy for the spark control and fuel injection control 45, although this system employs an exhaust sensor assembly indicated generally by the reference numeral 91 constructed in accordance with the invention.

So as to permit engine management, a number of sensors are employed. Some of these sensors are illustrated either schematically or in actual form, and others are not illustrated. It should be apparent to those skilled in the art, however, how the invention can be practiced with a wide variety of control strategies other than or in combination with those which form the invention.

The sensors as shown primarily in FIG. 1 include a crankshaft position sensor 90 which senses the angular position of the crankshaft 23 and also the speed of its rotation. A crankcase pressure sensor 92 is also provided for sensing the pressure in the individual crankcase chambers 38. Among other things, this crankcase pressure signal may be employed as a means for measuring intake air flow and, accordingly, controlling the amount of fuel injected by the injector 45, as well as its timing.

A temperature sensor 93 may be provided in the intake passage downstream of the throttle valve 42 for sensing the temperature of the intake air. In addition, the position of the throttle valve 42 is sensed by a throttle position sensor 94. Engine temperature is sensed by a coolant temperature sensor 95 that is mounted in an appropriate area in the engine cooling jacket 69. An in-cylinder pressure sensor 96 may be mounted in the cylinder head 61 so as to sense the pressure in the combustion chamber 59. A knock sensor 97 may also be mounted in the cylinder block 34 for sensing the existence of a knocking condition.

Certain ambient conditions also may be sensed, such as atmospheric air pressure by a sensor 98, intake cooling water temperature, as sensed by a sensor 99, this temperature being the temperature of the water that is drawn into the cooling system before it has entered the engine cooling jacket 69.

In accordance with some portions of the control strategy, it may also be desirable to be able to sense the condition of the transmission for driving the propeller 29 or at least when it is shifted into or out of neutral. Thus, a transmission condition sensor 100 is mounted in the power head and cooperates with the shift control mechanism for providing the appropriate indication.

Furthermore, a trim angle sensor 101 is provided for sensing the angular position of the swivel bracket 31 relative to the clamping bracket 33.

Finally, the engine exhaust gas back pressure is sensed by a back pressure sensor 102 that is positioned within the expansion chamber 74 which forms part of the exhaust system for the engine and which is positioned in the drive shaft housing 27.

The types of sensors which may be utilized for the feedback control system provided by the ECU 66 are only typical of those which may be utilized in conjunction with the invention. As has been noted, the invention deals primarily with the oxygen sensor 91 and its construction and the way in which exhaust gases are delivered to it. For that reason, further details of the description of the components of the engine and outboard motor that have no particular importance in conjunction with the understanding of the construction and operation of the oxygen sensor have been deleted.

To be able to understand the construction and operation of the oxygen sensor 91, it is also necessary to identify the various cylinders of the engine since, at least in some embodiments, the oxygen sensor 91 is associated with more than one cylinder of the engine 22, for reasons which will become apparent. In order to permit this description to be more clearly understood, the cylinders of the engine 22 have been numbered from top to bottom as cylinder 1, cylinder 2 and cylinder 3. In conjunction with the description of the exhaust sensor 91, therefore, certain of the components which have been employed to describe the actual physical parts of the cylinders may also be identified as associated with a particular cylinder through the use of a suffix indicating the cylinder number to the individual part number.

The cylinders are numbered from top to bottom with cylinder no. 1 being juxtaposed to a flywheel magneto assembly 103 that is affixed to the upper end of the crankshaft 23 in any well known manner. This flywheel magneto assembly 103 supplies electrical power for the aforenoted capacitor discharge ignition system. In addition, it may be provided with a ring gear 104 that cooperates with an electrically operated starter motor 105 (FIG. 3) that is affixed to one side of the cylinder block 34.

Figure 6:
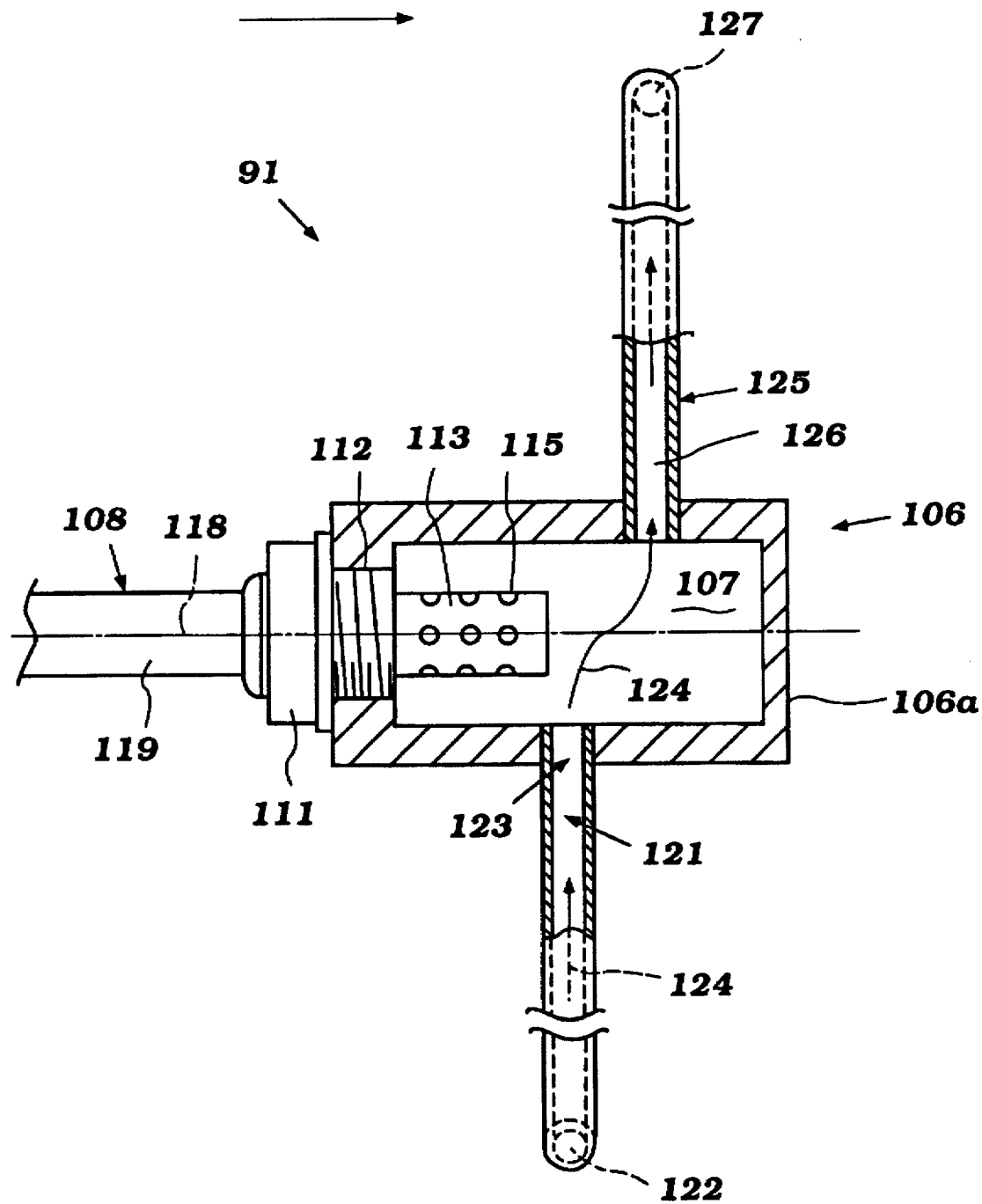
FIG. 6 is an enlarged view looking in the same direction as FIG. 2 with portions broken away and showing the sensor arrangement for the feedback control system of this embodiment.
Figure 7:
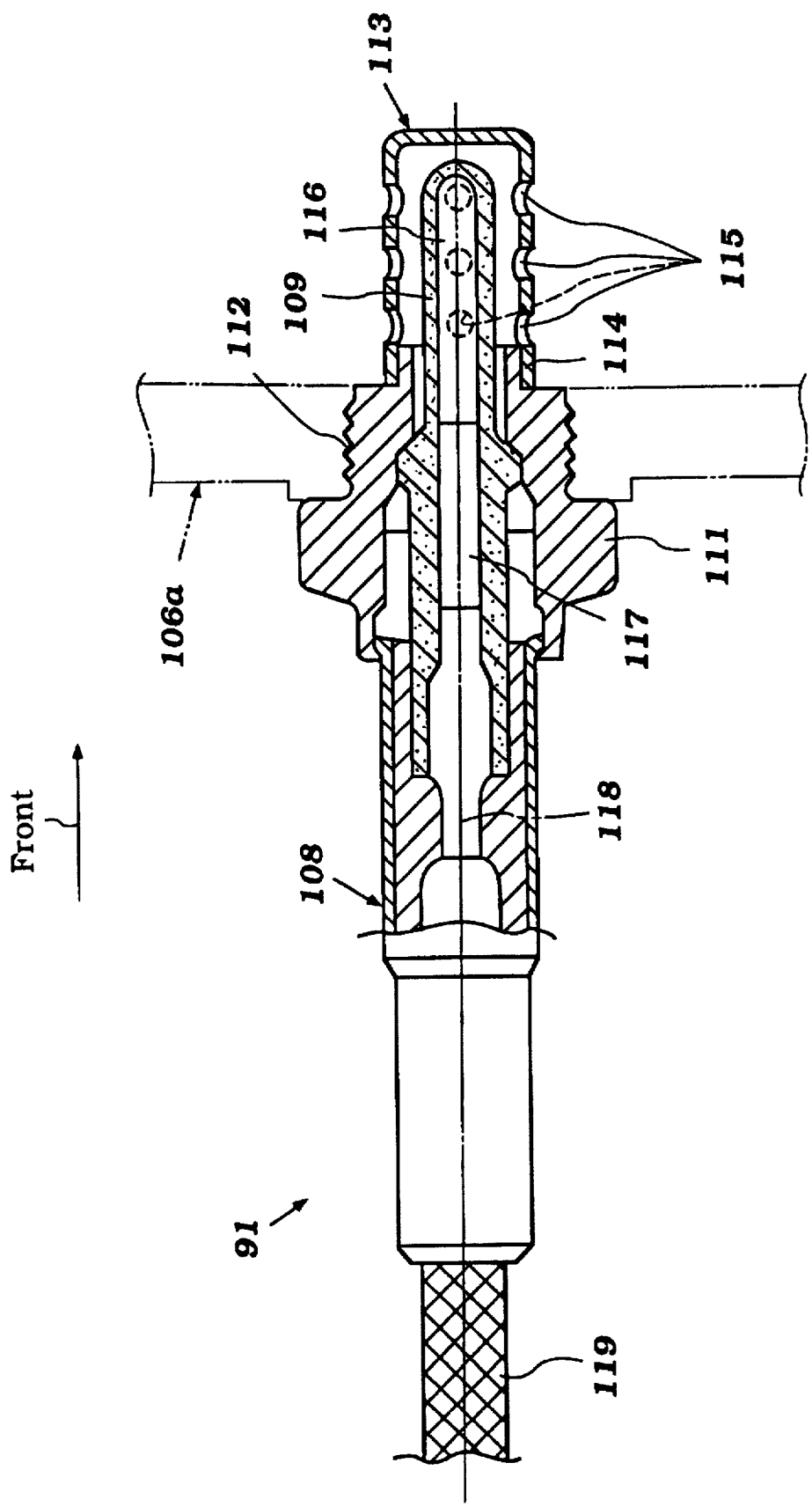
FIG. 7 is a further enlarged cross-sectional view, taken in the same direction as FIG. 6, but shows the sensor element, per se, and its protective arrangement.

The sensor assembly 91 has a construction as best shown in FIGS. 6 and 7, although its interaction with the engine will be described later by reference to other figures. The sensor assembly 91 is comprised of an outer housing assembly, indicated generally by the reference numeral 105, and which is comprised, in this embodiment, of an outer housing piece 106 that defines a relatively large accumulator volume 107.

A sensor element, in this case an oxygen sensor, indicated generally by the reference numeral 108, has its sensing portion 109 mounted within a fitting 111 which, in turn, has a threaded connection 112 with the outer housing element 106, so that the sensor portion 109 extends into the accumulator chamber 107. However, the sensor portion 109 is protected by means of a protecting shell 113 that is fitted onto a tubular projection 114 of the mounting fitting 111. A plurality of openings 115 are formed in the shell 113 so as to permit the communication of exhaust gases with the sensor portion 109, but also to protect the sensor portion 109 from damage.

The sensor portion 109 is formed as a platinum-plated glass tube having a hollow center 116. An electrical heater 117 extends in the hollow center 116 along the centerline 118 of the sensor 108 and which communicates with the ECU 66 through a shielded conductor 119. As is known, the element 109 will output a signal indicative of oxygen content in the exhaust gas, and thus provides an indicator whether the fuel/air mixture is stoichiometric or not. The actual constituency of the sensor 109 may be of any desired type utilized in this control art. The important features of the invention is that the sensor is positioned in the accumulator chamber 107 in such a manner and is of such a size that it occupies substantially less than one-half of the volume of the accumulator chamber 107. This ensures that the gas actually sensed by the sensor element 109 will be representative of the actual combustion products of the engine.

In this and in certain other embodiments, the exhaust gases or combustion products are delivered to the accumulator chamber 107 in a timed relationship from one cylinder of the engine. In this particular embodiment, the cylinder which supplies the exhaust gases to the accumulator chamber 107 is cylinder no. 2. The way in which this is accomplished will now be described by primary reference to FIGS. 6–10, although the structure also appears in certain of the other figures.

Figure 9:
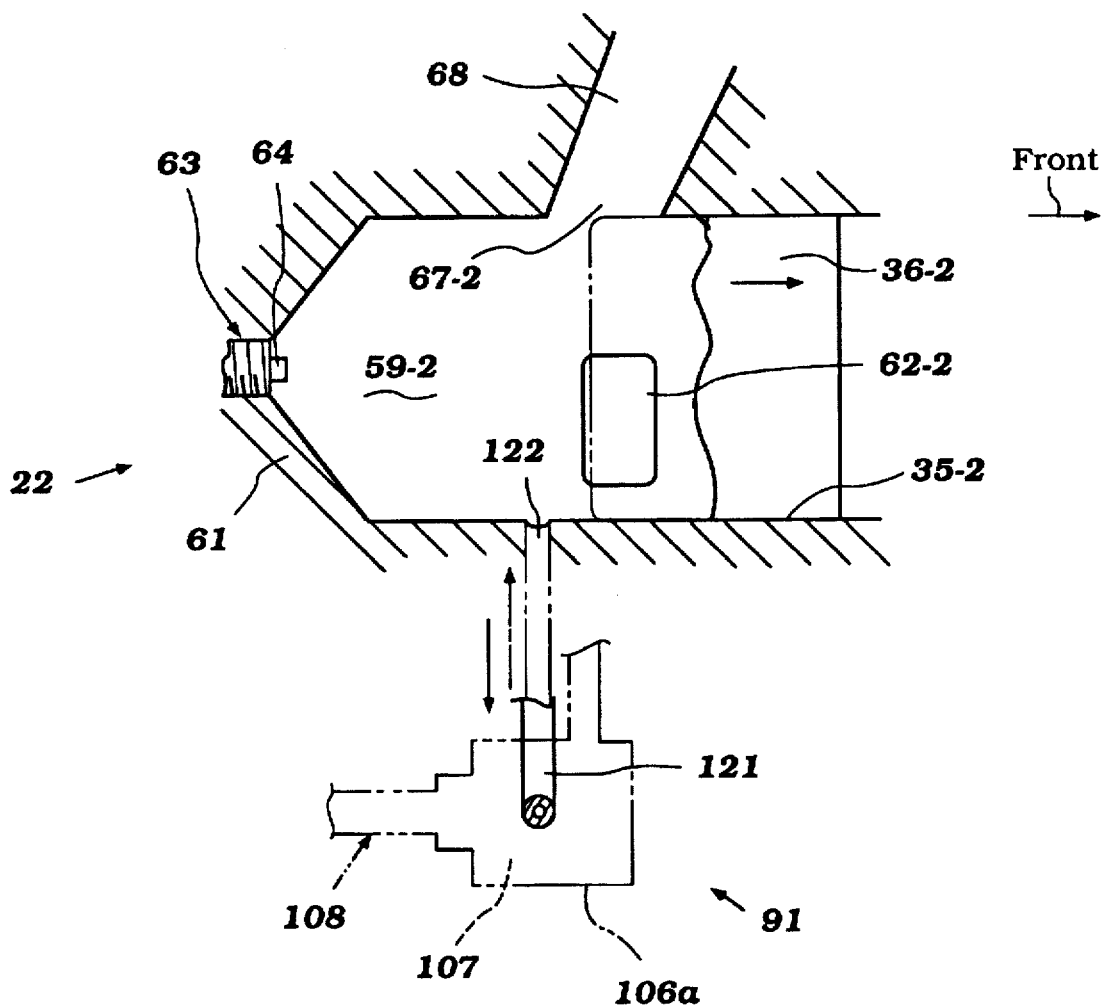
FIG. 9 is a view, in part similar to FIG. 8, and shows the connection of the sensor to the other cylinder in this embodiment.

A first or inlet conduit 121 opens into the accumulator chamber 107 and has an inlet port 122 which opens into the cylinder bore 35-2 of the no. 2 cylinder. This inlet port 122 is disposed at a point approximately equal to the point where the exhaust port 67-2 is opened as the piston 36-2 is moving down at the end of the expansion and the beginning of the scavenge stroke, as shown in FIG. 9. The direction of piston travel is indicated by the arrow 123. Thus, under the condition as shown in FIG. 9, exhaust or combustion gases will flow from the combustion chamber 59-2 into the accumulator chamber 107 through a port 123 formed at the end of the conduit 121, and as shown by the arrow 124. It should be noted that this communication is open at the time when the piston 36-2 first slides past the communication port 122, and this occurs substantially at the end of the combustion and expansion phase and before the scavenge ports 62-2 of this cylinder (2) are opened.

Figure 8:
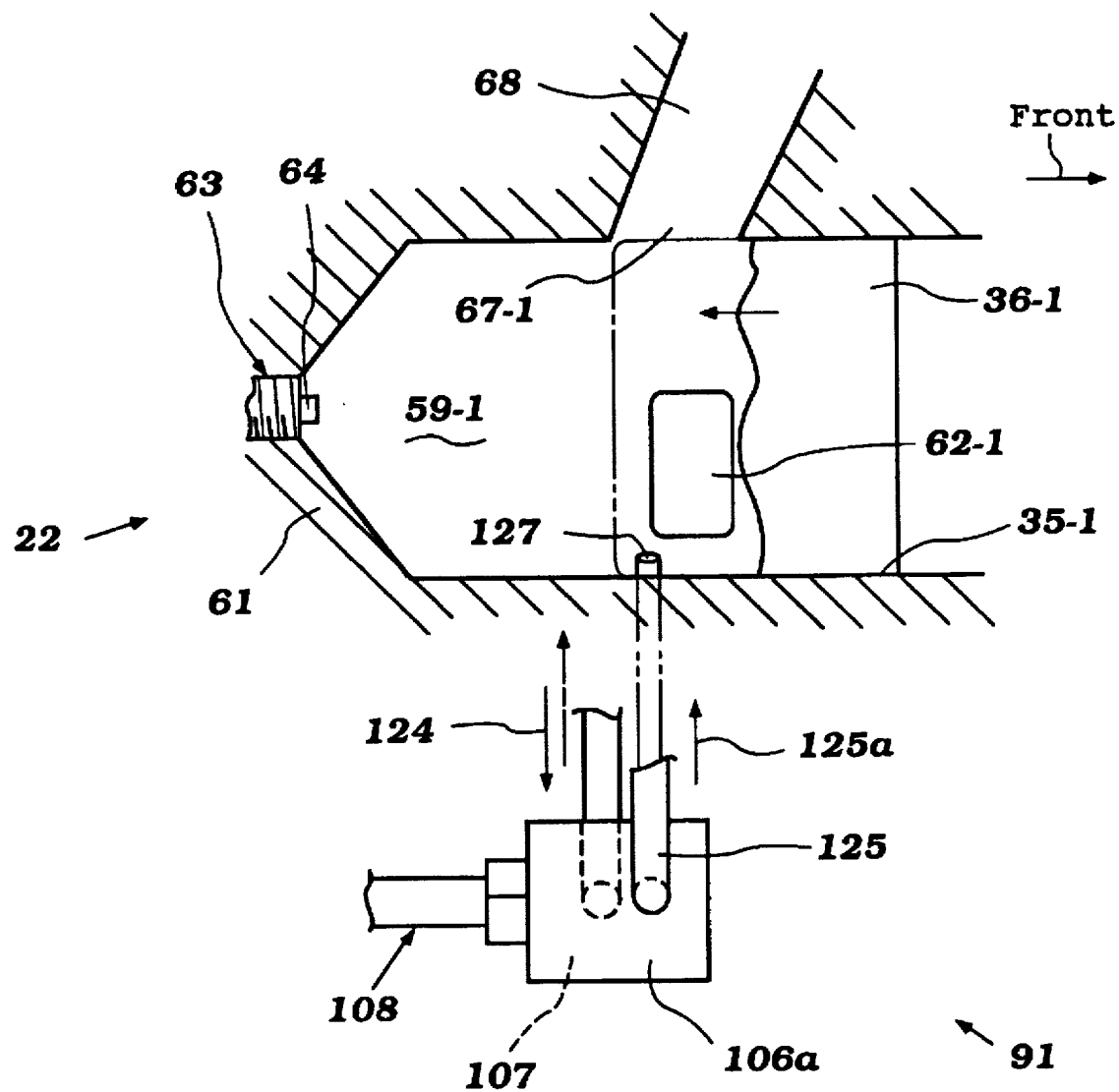
FIG. 8 is a partially schematic view and shows the relation of the sensor to one of the two cylinders with which it is connected in this embodiment.

A further and exhaust conduit 125 extends from a point in the accumulator chamber 107 that is, in this embodiment, spaced further from the sensor element 109 than the port 122 from cylinder no. 2. This communication passageway 125 has an inlet port 126 which opens into the accumulator chamber 107 and a discharge port 127 which communicates with cylinder no. 1, as shown in FIG. 8.

It should be noted that the communication port 127 intersects the cylinder bore 35-1 at a point adjacent where its scavenge port 62-1 will be opened when the piston 36-1 moves downwardly. That is, the ports 122 and 127 of the communication conduits 121 and 125 have a different timing relative to the events in the cylinders with which they are associated. Also, it should be noted that the cylinders are out of phase with each other, as is typical with engine practice, so as to provide more uniform firing impulses. This condition may be best seen in FIG. 10, wherein the timing phase for each cylinder is depicted in relation to crankshaft rotation.

It will be seen that the cylinders 1, 2 and 3 reach top dead center position at 120° from each other so as to provide equal firing impulses. It will be also seen from FIG. 10 that because of the spacing of the respective port openings 122 and 127, the port opening 122 will be opened and closed for approximately equal crank angles. However, the port 127 will be opened a shorter time than that of the port 122, and closed for a longer time than it is open. Also, the opening and closing times are staggered from each other, as shown in this figure, due to the difference in timing of the individual cylinders.

Figure 10:
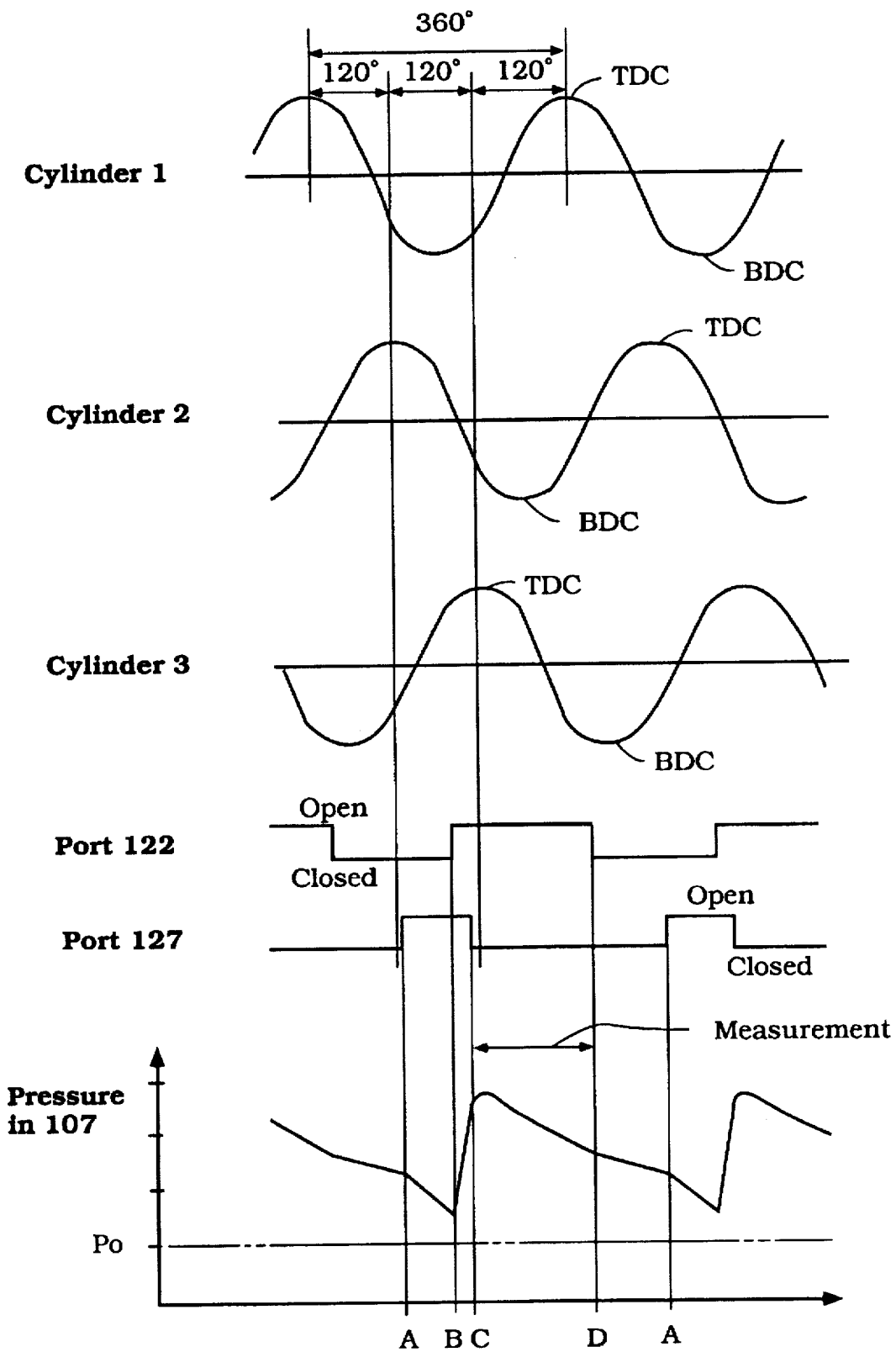
FIG. 10 is a graphical view showing the cycle of operation of each of the three cylinders of the engine of this embodiment in relation to crank angle, the condition of the porting communications to the sensor in the sensed cylinder and the controlling cylinder, and the pressure existent in the accumulator chamber where the sensor element is positioned, and the sensor timing interval.

Thus, beginning at the crankshaft rotation indicated by the point A in FIG. 10, cylinder no. 2 will be at a point slightly after its top dead center position, with the piston 36-2 moving downwardly in the cylinder bore, as shown by the arrow in FIG. 9. However, the piston 36-2 will be displaced in the cylinder bore 35-2 well above the position shown in FIG. 9 so that the port 22 will be closed and the combustion will have just begun and the gases will be expanding. At this same time, the piston 36-1 in cylinder no. 1 will still be traveling downwardly in a direction opposition to the arrows shown in FIG. 8 and the piston will be approximately in the position shown in FIG. 8, with the port 127 just about to open. At this time, the pressure of the gases trapped in the chamber 107 will have fallen to a point, as shown in this figure from internal leakage.

Upon continued rotation of the crankshaft 23, the port 127 will open, while the port 122 is still closed, and the pressure in the accumulator chamber 107 will fall and the gases will flow from the chamber 107 to the cylinder bore 35-1. At this point in time, the pressure in the cylinder bore 35-1, and specifically in its combustion chamber 39-1, will be substantially lowered because the exhaust port will have been open for some time and the scavenge port will have just opened along with the opening of the port 127. Thus, the pressure in the accumulator chamber 107 will be higher than this pressure and flow will occur in the direction of the arrows, as indicated in FIG. 8. FIG. 10 also shows the drop-off of pressure in the accumulator chamber.

This movement continues with the piston 36-1 of cylinder 1 reaching its bottom dead center position and then moving upwardly, as shown by the arrow in FIG. 8, in a direction to close the scavenge port 62-1 and eventually the port 127 communicating with the accumulator chamber 107. However, before the port 127 is closed, the piston in 36-2 in cylinder no. 2 will have moved past the port 122 and it will be opened at approximately the same time the exhaust port 67-2 of this cylinder opens. As a result, the high pressure gases from the combustion chamber 59-2, which have not had a chance to dissipate through full opening of its exhaust port 67-2, will flow through the conduit 121, as shown by the arrow 124, into the accumulator chamber 107.

When the port 122 does close at the point B, then the pressure in the accumulator chamber 107 will built up quite rapidly, and the accumulator chamber 107, which has been purged by the flow when both ports were open, will be charged with the fresh combustion products from combustion chamber 59-2. This build-up pressure occurs until and slightly after the point C when the port 127 closes. This operation continues, although the pressure in the accumulator chamber 107 will then begin to fall, due to the exhaust of gases as its exhaust port 67-2 is opened, until this port again closes at the crank angle D.

Hence, the time period C to D is a time period when the exhaust gases in the chamber 107 will represent the instantaneous condition in cylinder no. 2 and the ECU 66 is programmed so as to read the output from the sensor element 109 during this time period. Thus, a very good reading of exhaust gas constituents combustion process can be measured at this time, and then appropriate feedback control initiated by the ECU 66 to provide the appropriate air/fuel ratio and exhaust emission control.

Figure 11:
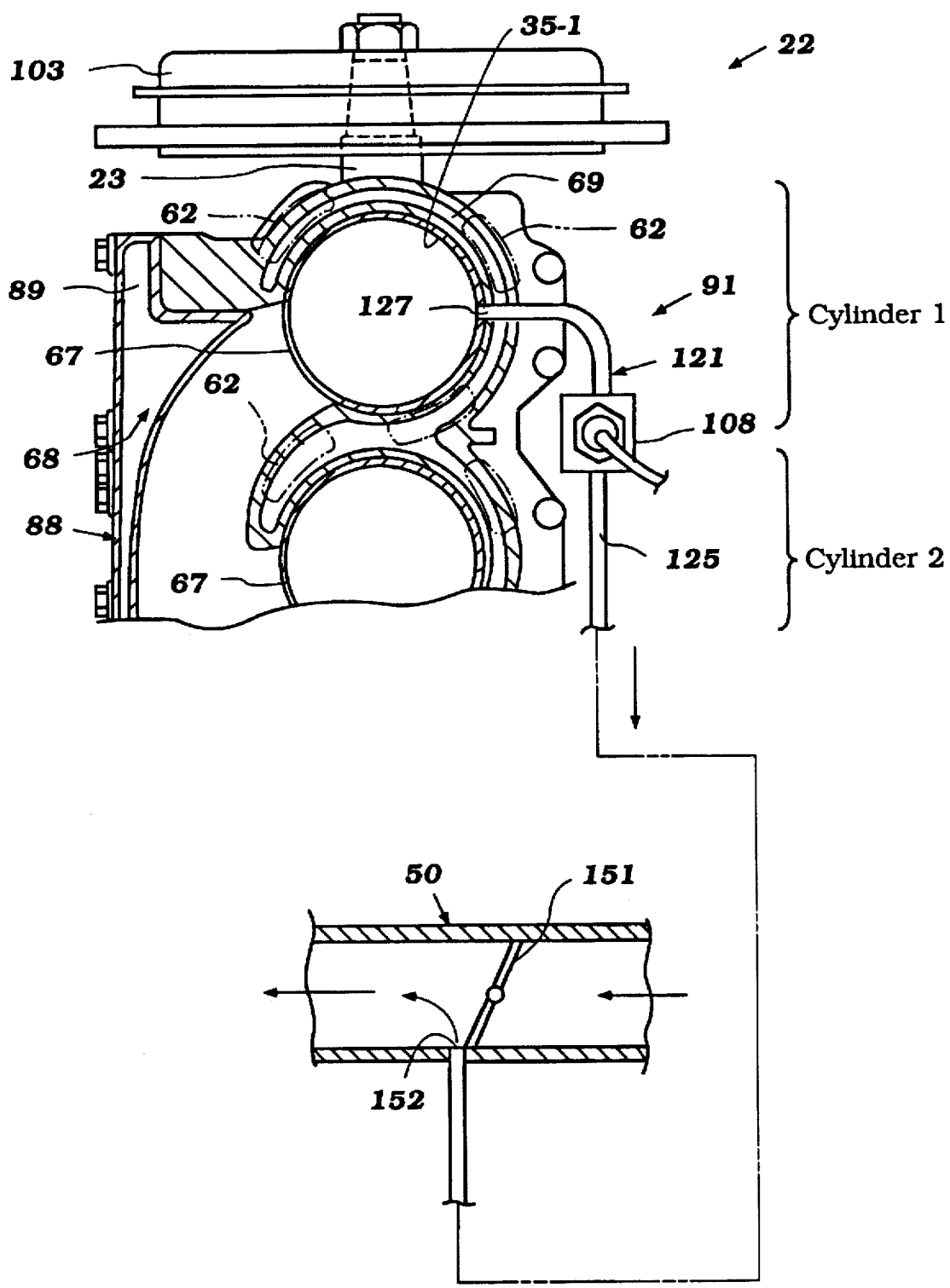
FIG. 11 is a view, in part similar to FIG. 4, with other portions being shown schematically, and illustrates another embodiment of the invention.

In the embodiment thus far described, the exhaust condition sensor 91 has received its inlet of exhaust gases from cylinder no. 2, and exhaust gases were discharged from the accumulator chamber 107 to cylinder no. 1. FIG. 11 shows another embodiment of the invention wherein the sensor 91 receives exhaust gases from cylinder no. 1 and the exhaust gases are discharged not directly back to another cylinder, but back to the induction system, and specifically the intake manifold 50 at a point downstream of the throttle valve of one of the intake runners. This throttle valve is shown in this figure and is identified by the reference numeral 151. Thus, the supply conduit 121 has its inlet port 122 in communication with the cylinder bore 34-1 at a point substantially the same as the communication passageway with cylinder bore 34-2 of the previously described embodiment. The discharge passageway 125, however, has a discharge end 152 in communication with the intake passage of the manifold 50 downstream of the throttle valve 151. Thus, the exhaust gases will be bled back in and mixed with the intake charge. This may, in fact, be utilized to provide a limited amount of exhaust gas recirculation. The operation of this embodiment should be apparent from the foregoing description and, for that reason, further description of this embodiment is not believed to be necessary to permit those skilled in the art to practice the invention.

Figure 12:
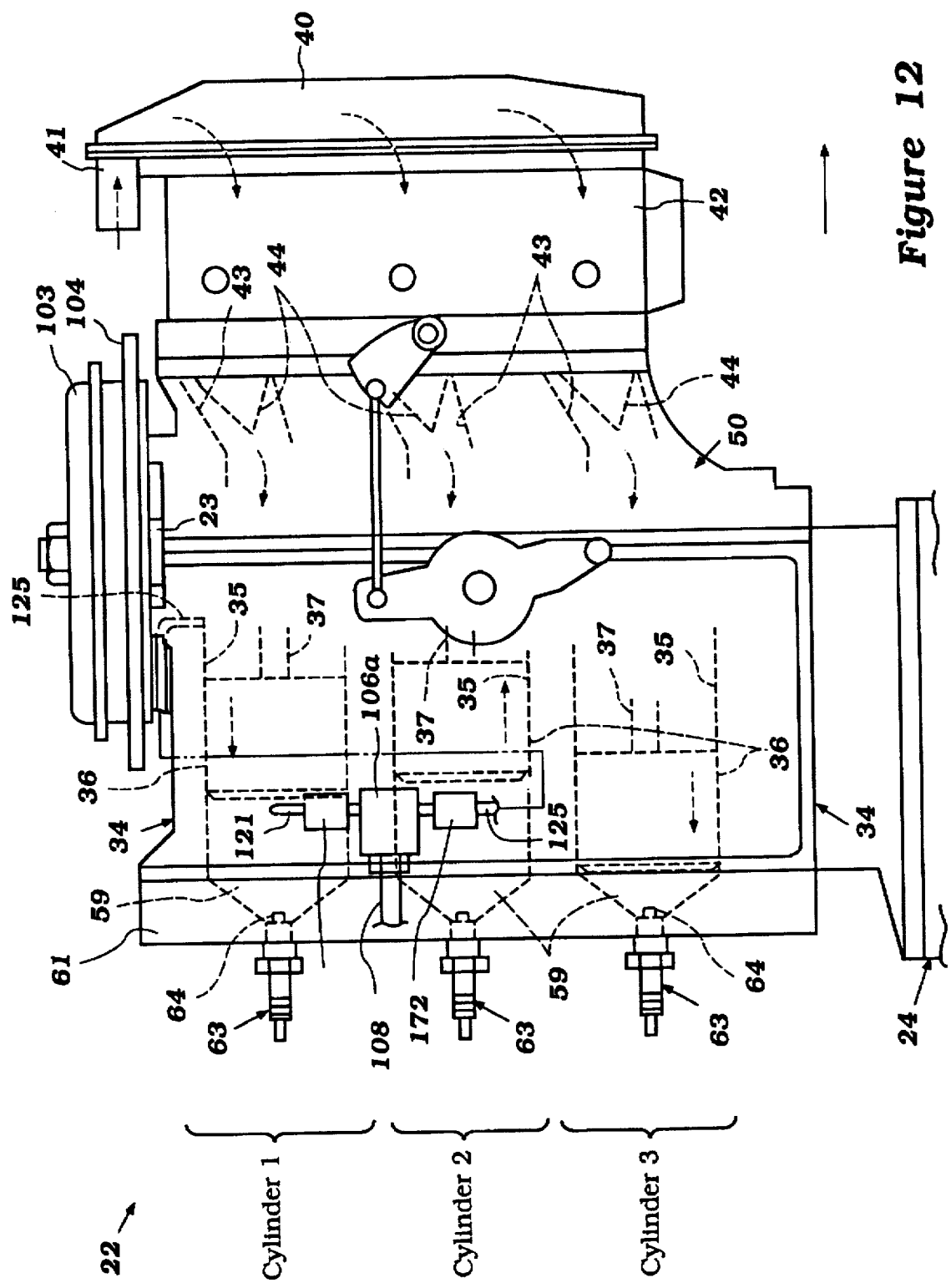
FIG. 12 is a side elevational view, in part similar to FIG. 2, and shows a further embodiment of the invention.
Figure 13:
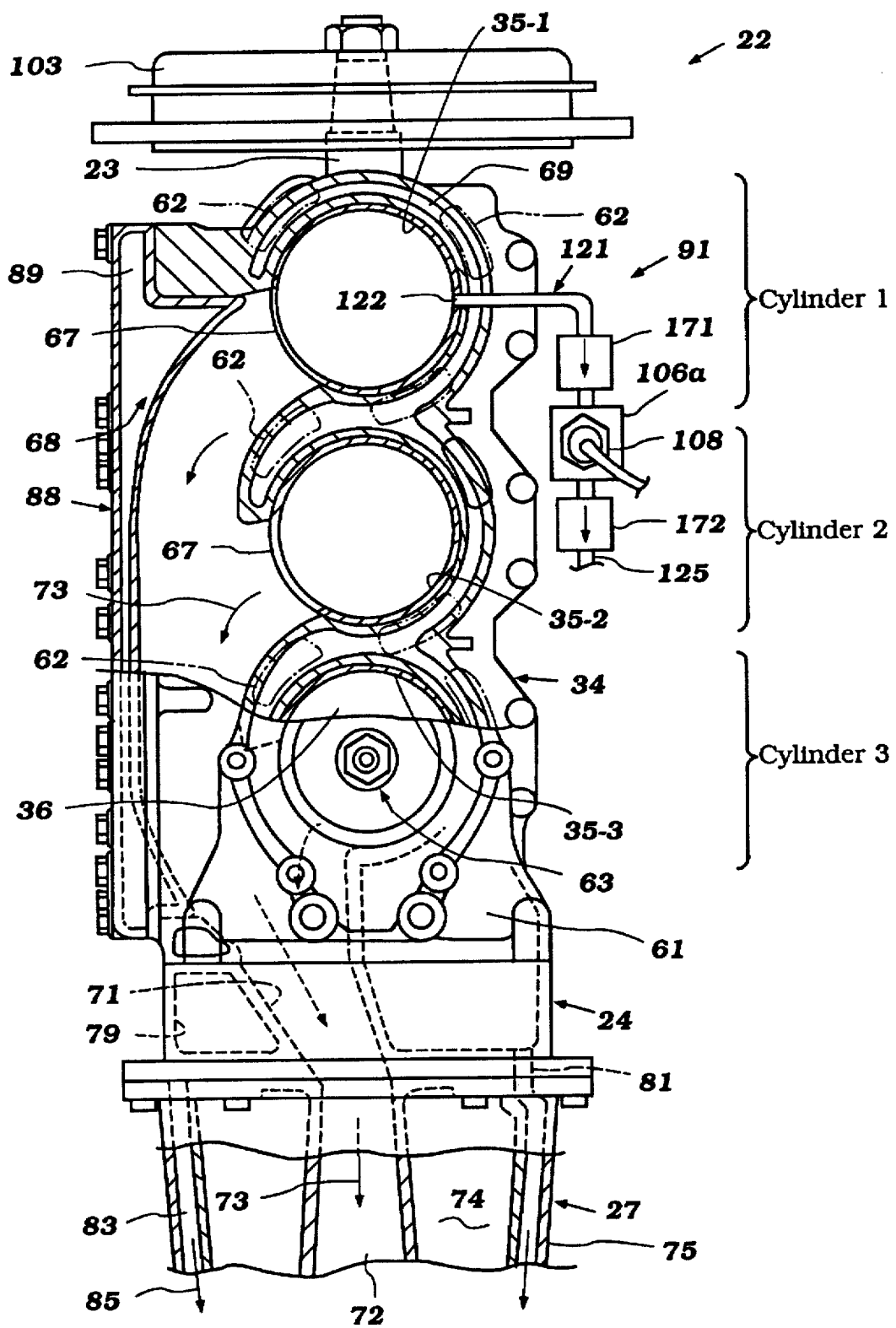
FIG. 13 is a rear elevational view, with a portion broken away, of the embodiment of FIG. 12.

FIGS. 12 and 13 show another embodiment which is similar to the embodiment of FIG. 11, and the overall engine construction is similar to the embodiment of FIGS. 1–10. For that reason, where components of this embodiment are the same or substantially the same as those previously described, they have been identified by the same reference numerals.

In this embodiment, the accumulator chamber 107, and specifically its discharge conduit 125, is communicated with a crankcase chamber of the engine. The conduit 121 has its port 122 communicating with the cylinder bore 34-1 in the manner previously described. In addition, a pair of one-way check valves, indicated by the reference numerals 171 and 172, are provided in the inlet conduit 121 and exhaust conduit 125, respectively. These check valves 171 and 172 permit flow only in the direction of the arrows illustrated, and, therefore, it will be ensured that reverse flow cannot occur. That is, the accumulator chamber 107 will always be charged from the cylinder bore 34-1 and will discharge always to the crankcase chamber. No reverse flow will be permitted because of the check valves 171 and 172.

Figure 14:
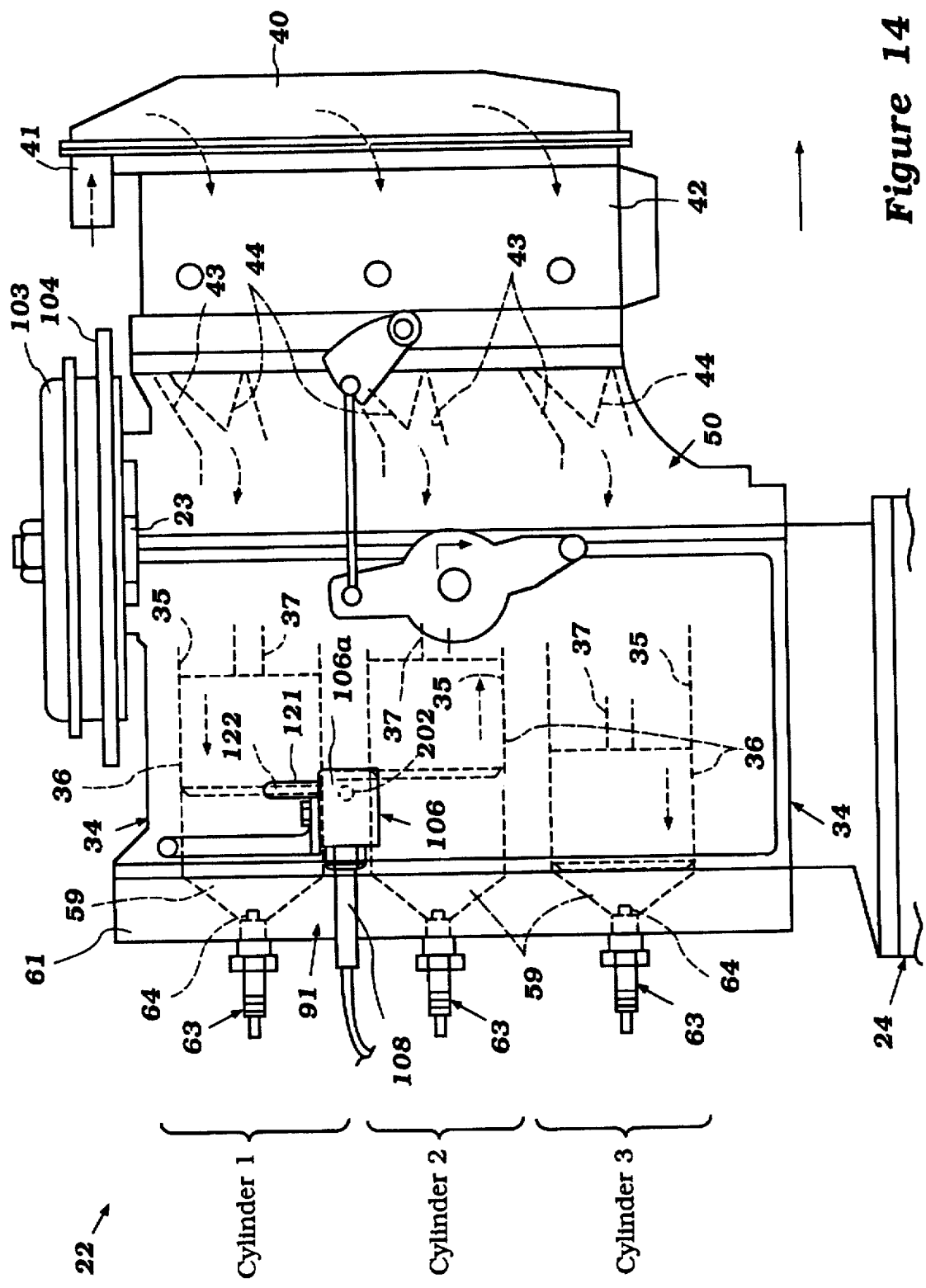
FIG. 14 is an enlarged side elevational view, in part similar to FIGS. 2 and 12, and shows another embodiment of the invention.
Figure 15:
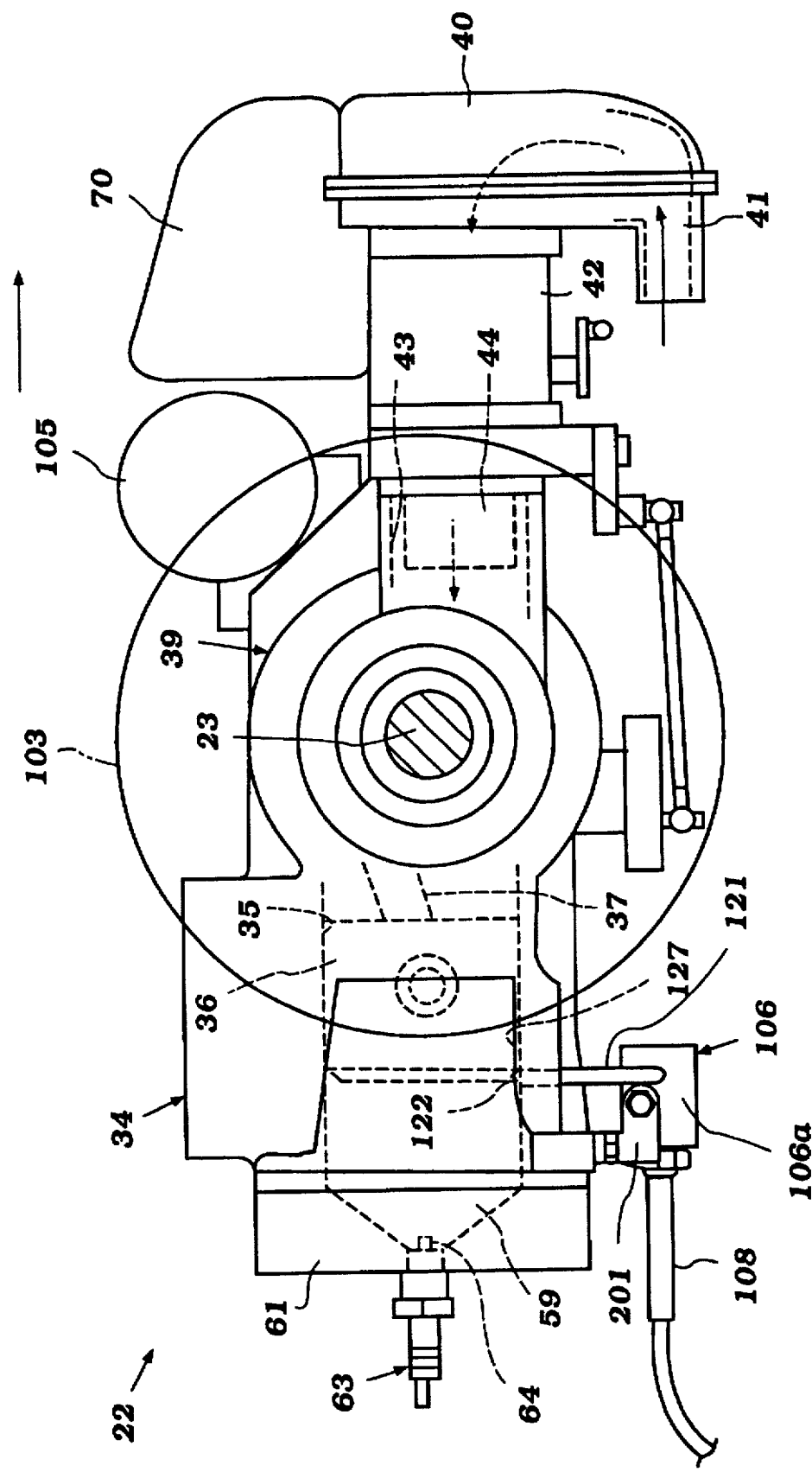
FIG. 15 is a top plan view of the embodiment of FIG. 14.
Figure 16:
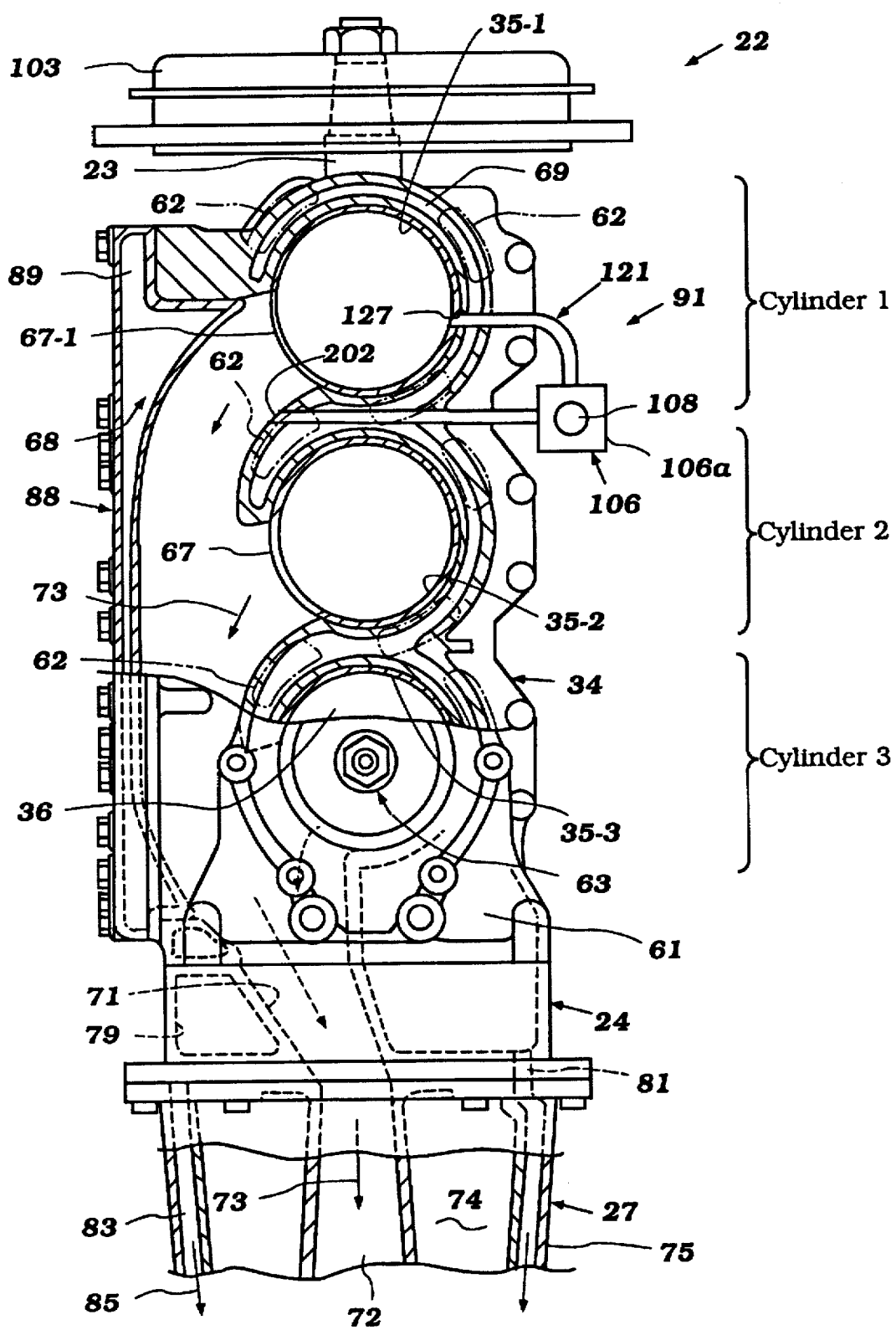
FIG. 16 is a rear elevational view of this embodiment, with a portion broken away, and is similar in part to FIGS. 4, 11 and 13.
Figure 17:
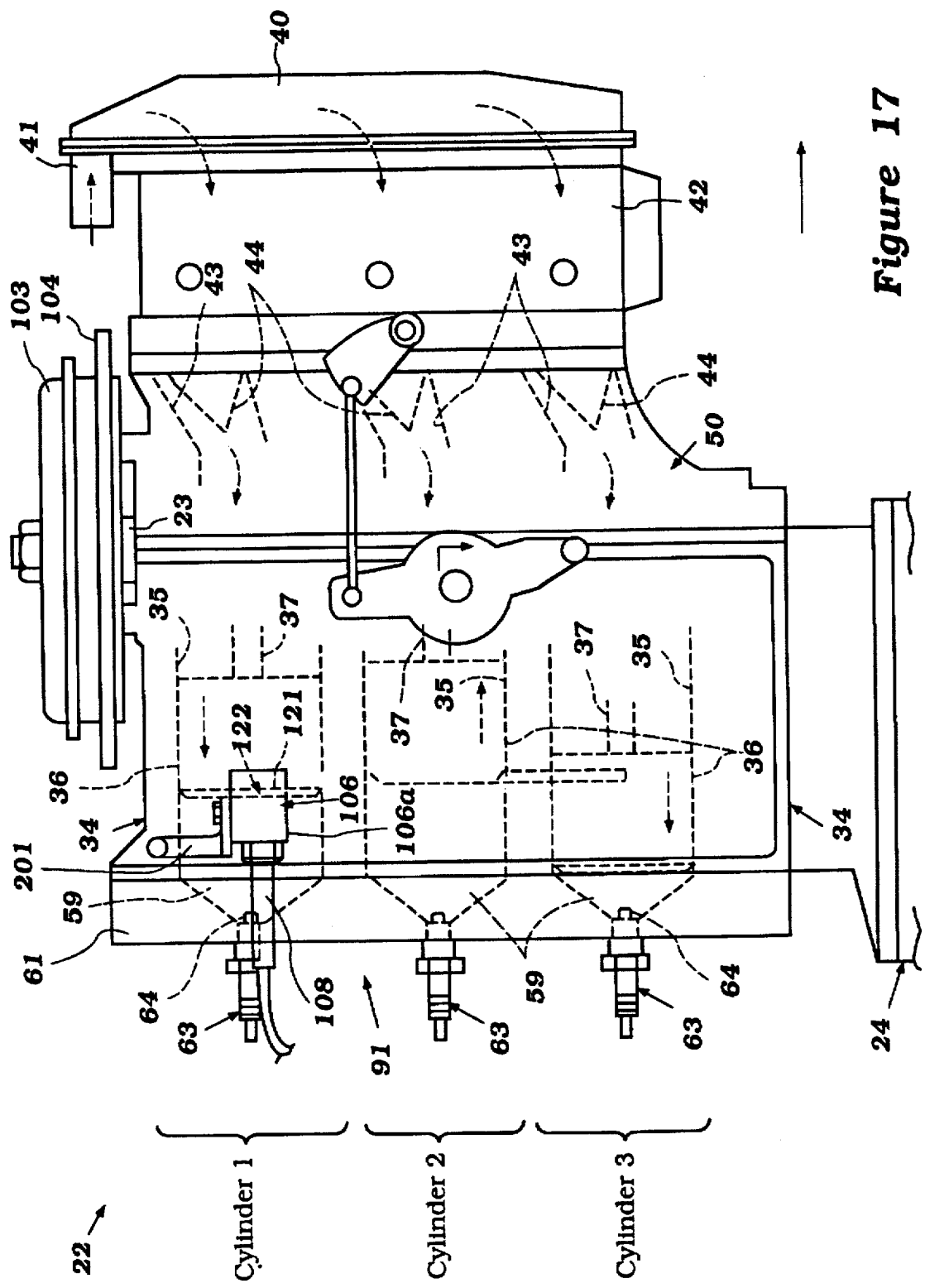
FIG. 17 is a side elevational view, in part similar to FIGS. 2, 12 and 14, and shows yet another embodiment of the invention.

FIGS. 14–16 show another embodiment of the invention which is generally similar to those embodiments thus far described, and where the components are the same or substantially the same, they have been identified by the same reference numerals and will only be described again as is necessary to understand the construction and operation of this embodiment.

In this embodiment, the sensor 91, and specifically its housing 106, is mounted to the cylinder block 34 by means of a mounting bracket 201. The mounting bracket 201 is appropriately affixed to the cylinder block.

In this embodiment, like those of FIGS. 11 and 12 and 13, the pressure supply conduit 121 for the accumulator chamber 107 has its inlet port 122 in registry with the first cylinder bore 34-1 at a location as previously described. With this embodiment, the discharge conduit 127 extends in part through the cylinder block 34 and terminates in a discharge opening 202 that communicates with the exhaust manifold 68, and specifically the portion of the exhaust manifold adjacent the exhaust port 67-1 of cylinder no. 1. In other regards, this embodiment is the same as those previously described and, for that reason, further description of this embodiment is not believed to be necessary to permit those skilled in the art to practice the invention.

FIGS. 17–20 show a sensor 91 constructed in accordance with yet another embodiment of the invention. Like those embodiments previously described, many components of this embodiment are the same as those described previously and, for that reason, components which are the same have been identified by the same reference numerals and will not be described again, except insofar as is necessary to understand the construction and operation of this embodiment.

Like the embodiment of FIGS. 14–16, the sensor housing 105 is mounted on the cylinder block 34 by a mounting bracket which has a slightly different configuration than that of that embodiment, but since it is the same in function, it has been indicated by the same reference numeral (201). In this embodiment, however, there is provided only an inlet conduit 121 which has its inlet port 122 in communication with the cylinder bore 34-1 at a point adjacent that corresponding to the opening of the exhaust port for this cylinder. In this embodiment, there is, however, no discharge conduit. Thus, the construction is simpler but will not provide as accurate an indication of each firing of the cylinder. However, the leak-down of pressure that occurs will cause sufficient fluctuation to provide good signals and, as noted above, this embodiment is simpler than those previously described.

Figure 18:
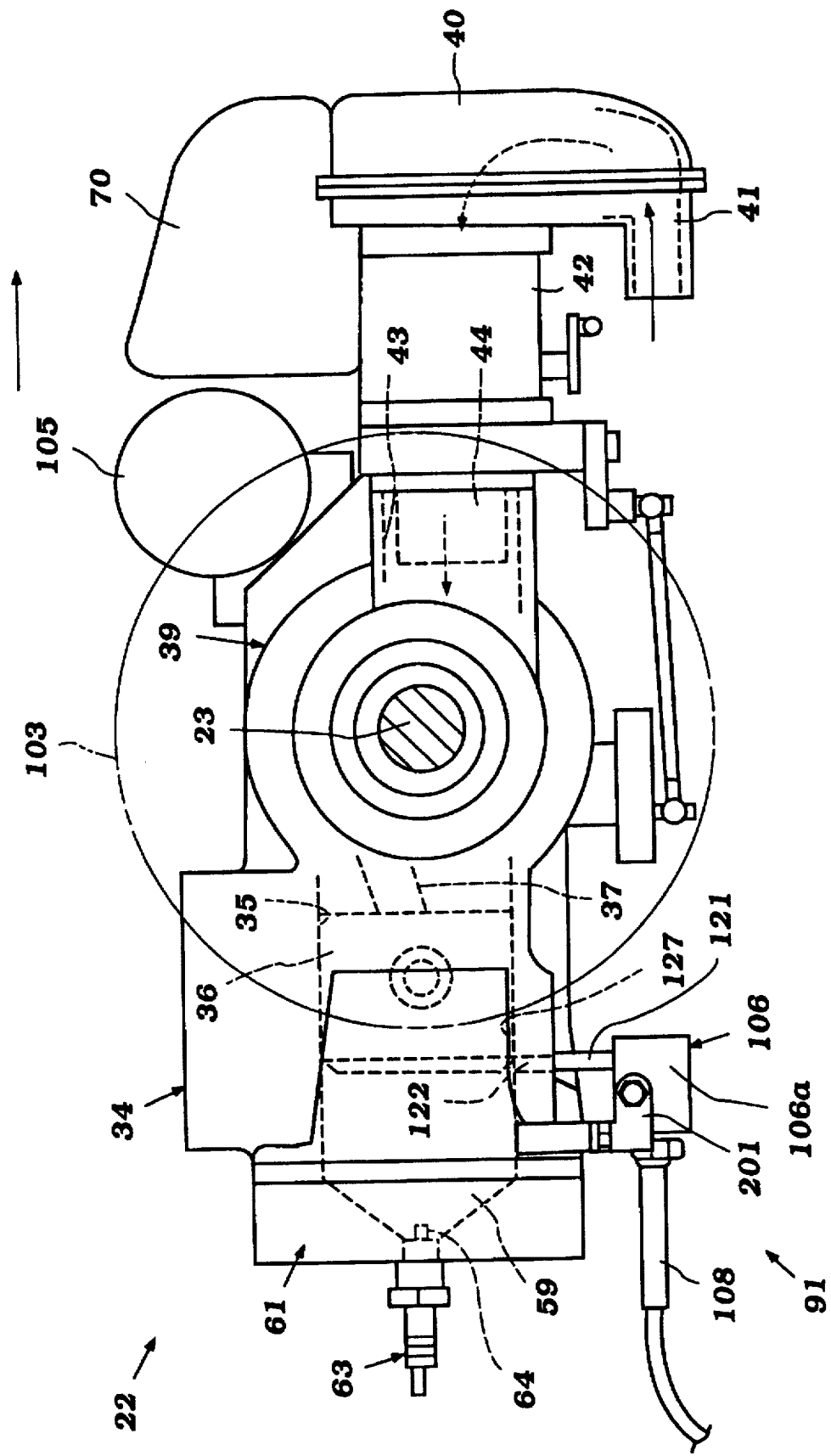
FIG. 18 is a top plan view of this embodiment.
Figure 19:
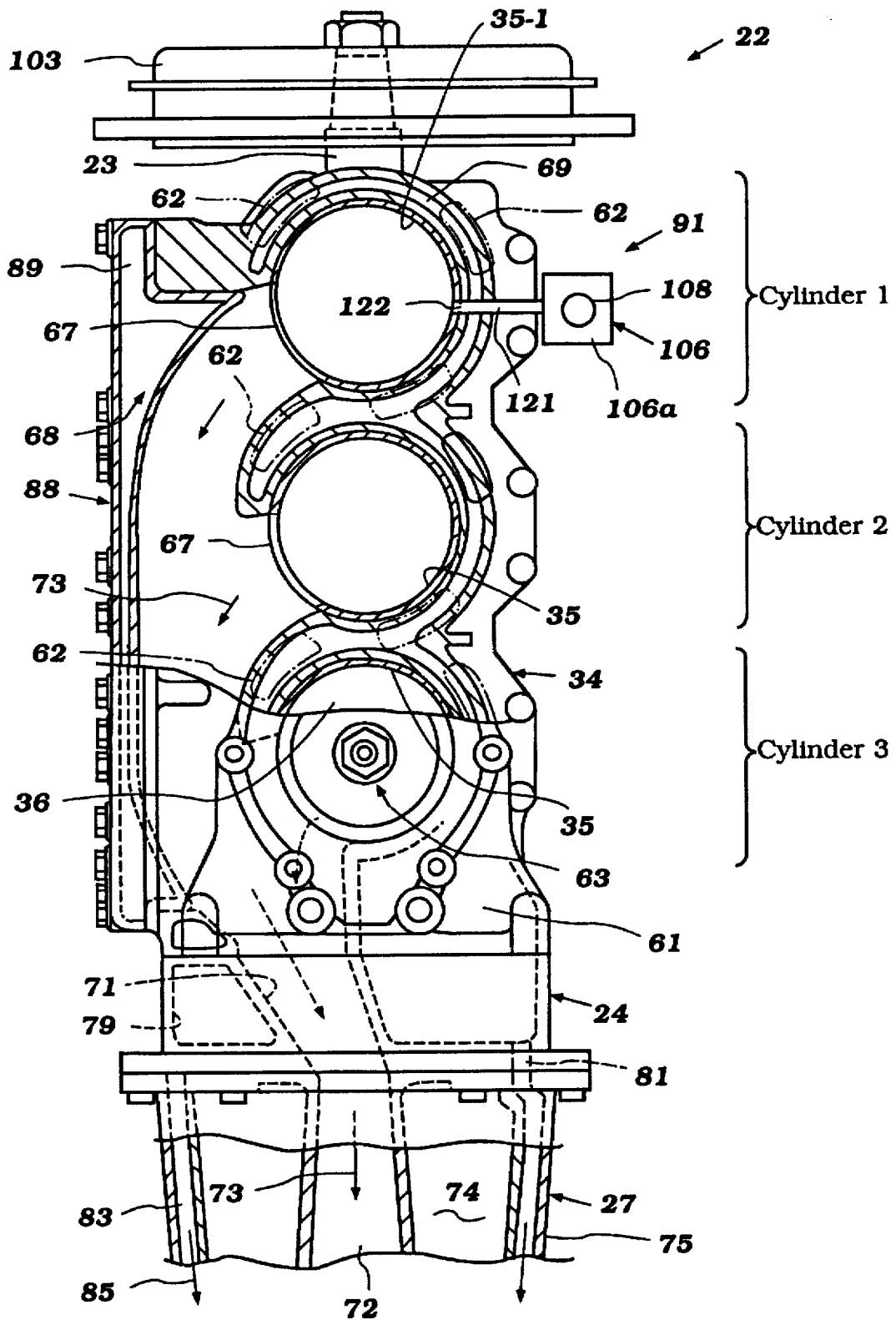
FIG. 19 is a rear elevational view of this embodiment, with a portion broken away and shown in section, and is in part similar to FIGS. 4, 11, 13 and 16.
Figure 20:
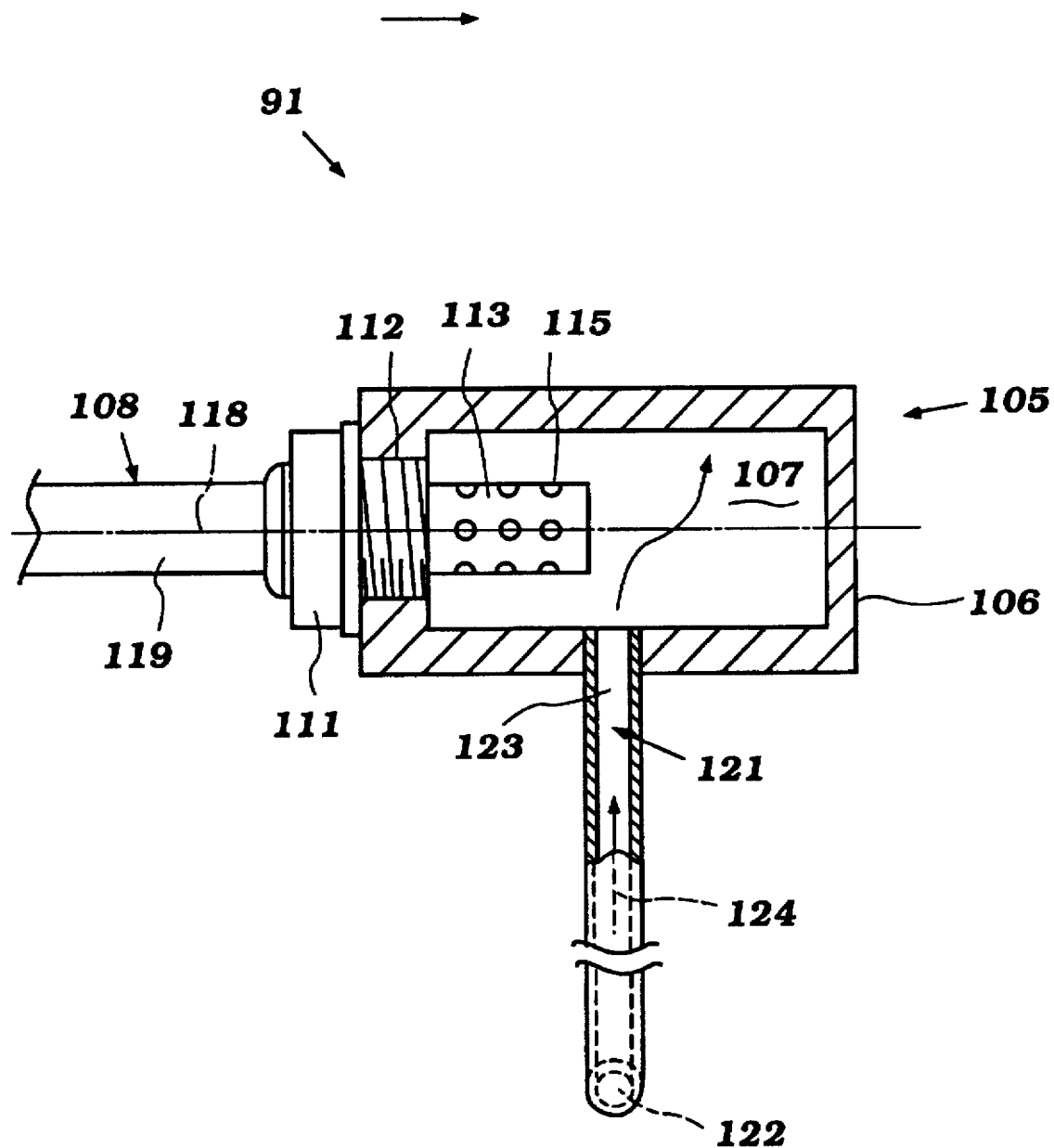
FIG. 20 is a further enlarged partially cross-sectional view, taken through the sensor of this embodiment.
Figure 21:
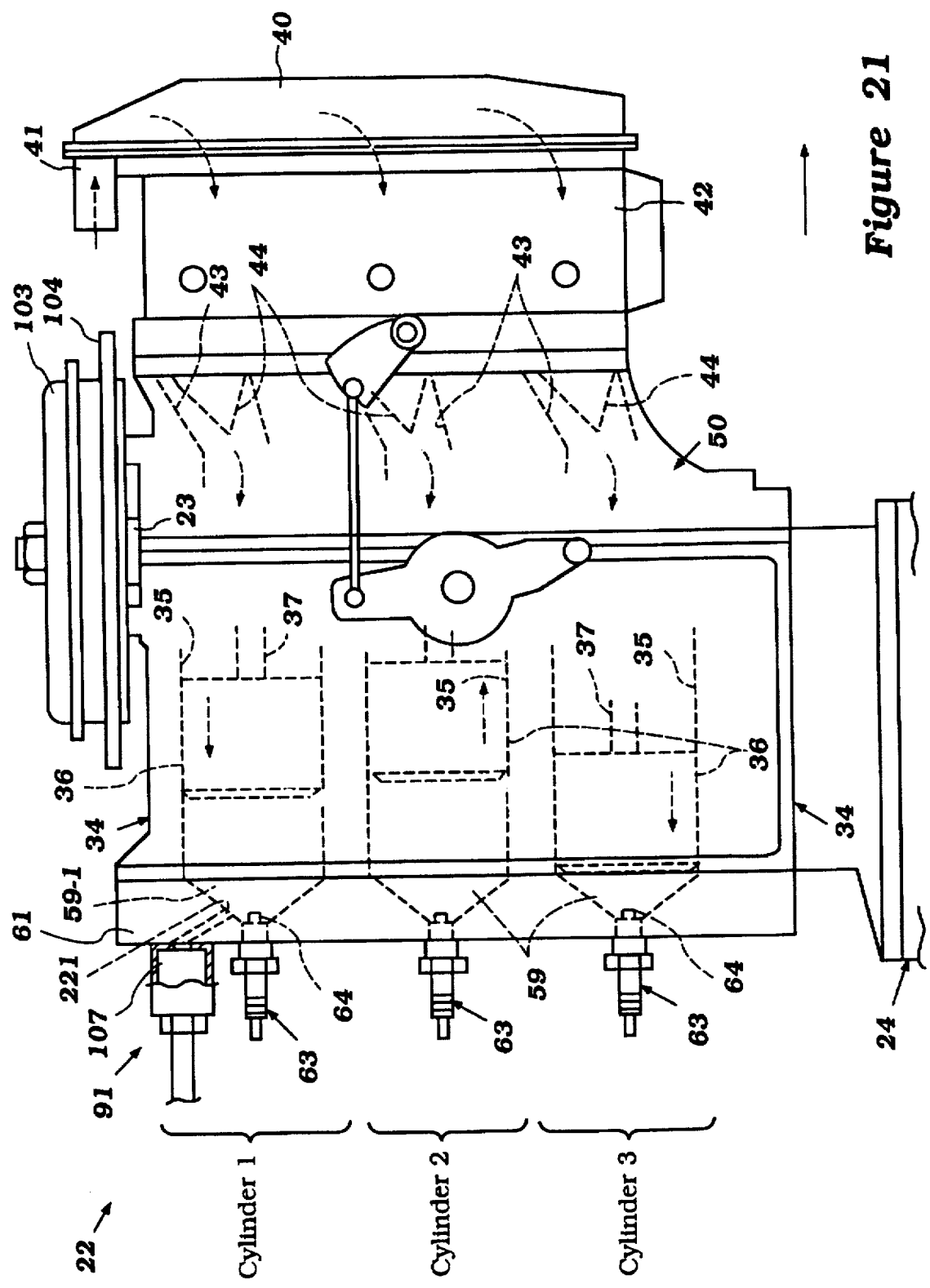
FIG. 21 is an enlarged side elevational view, in part similar to FIGS. 2, 12, 14 and 17 of a still further embodiment of the invention.
Figure 22:
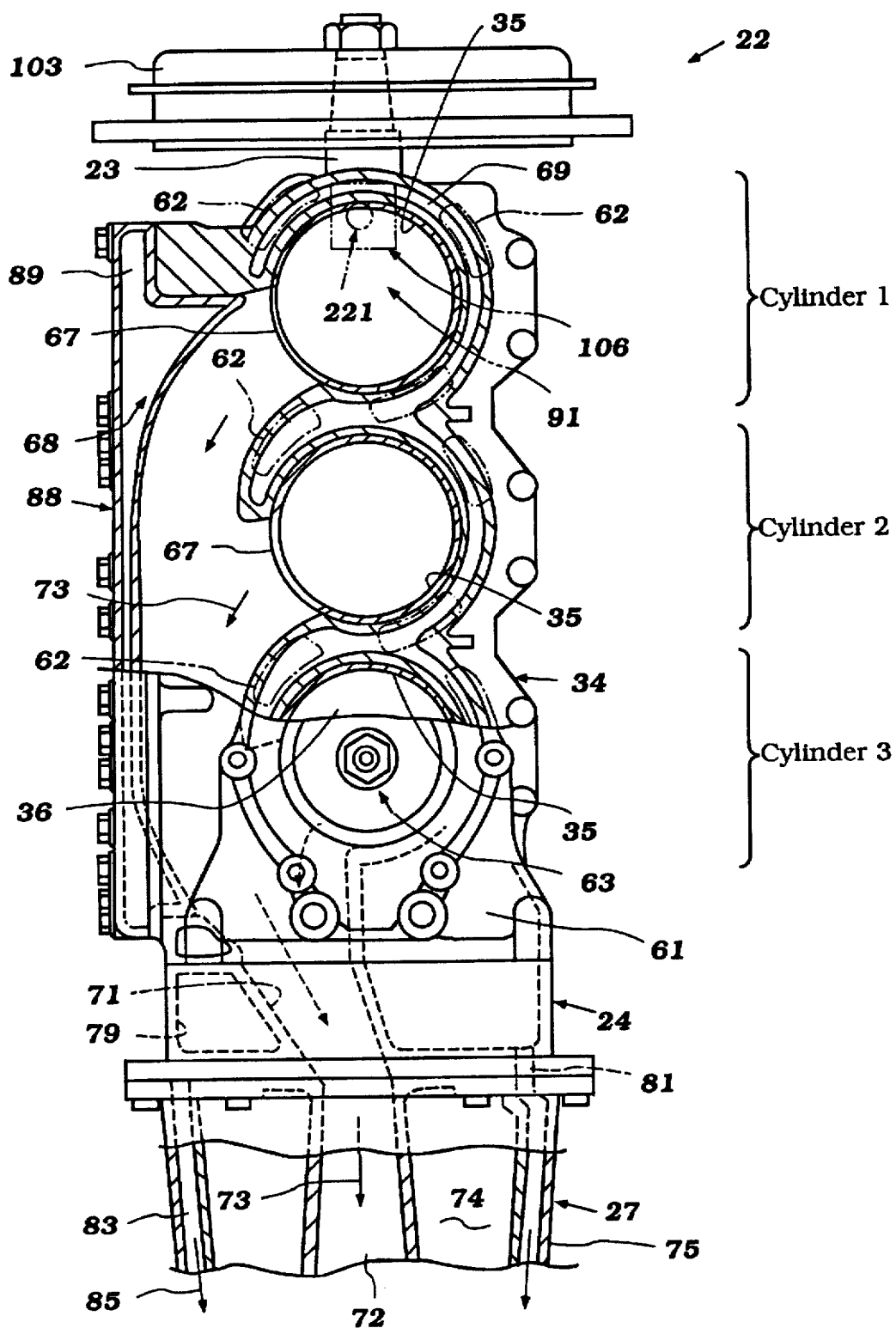
FIG. 22 is a rear elevational view, with a portion broken away and shown in section of this embodiment, and is in part similar to FIGS. 4, 11, 13, 16 and 19.

FIGS. 21 and 22 illustrate another embodiment which has the simplicity of the embodiment of FIGS. 18–20, in that it only has one communication passageway, but will also ensure that the accumulator chamber 107 will receive a charge that is indicative of cycle-to-cycle operations. In this embodiment, the sensor 91 is mounted directly on the cylinder head 61 and communicates with an internal passageway 221 formed therein, which communicates with one of the combustion chambers 59, in this instance the combustion chamber 59-1, associated with the no. 1 cylinder. Thus, there will be flow into and out of the accumulator chamber during the entire engine cycle.

In all of the embodiments as thus far described, the sensor 91 has been positioned and constructed so as to receive the combustion products directly from the respective combustion chamber 59. Next will be described a series of embodiments wherein the sensor 91 contacts the combustion products at a position in the exhaust system. In each of these embodiments, the structure of the sensor 108, per se, is the same as that previously described. However, the accumulator chamber, which will be identified by a different reference numerals, is formed integrally within either the engine 22 or another component of the outboard motor.

Figure 23:
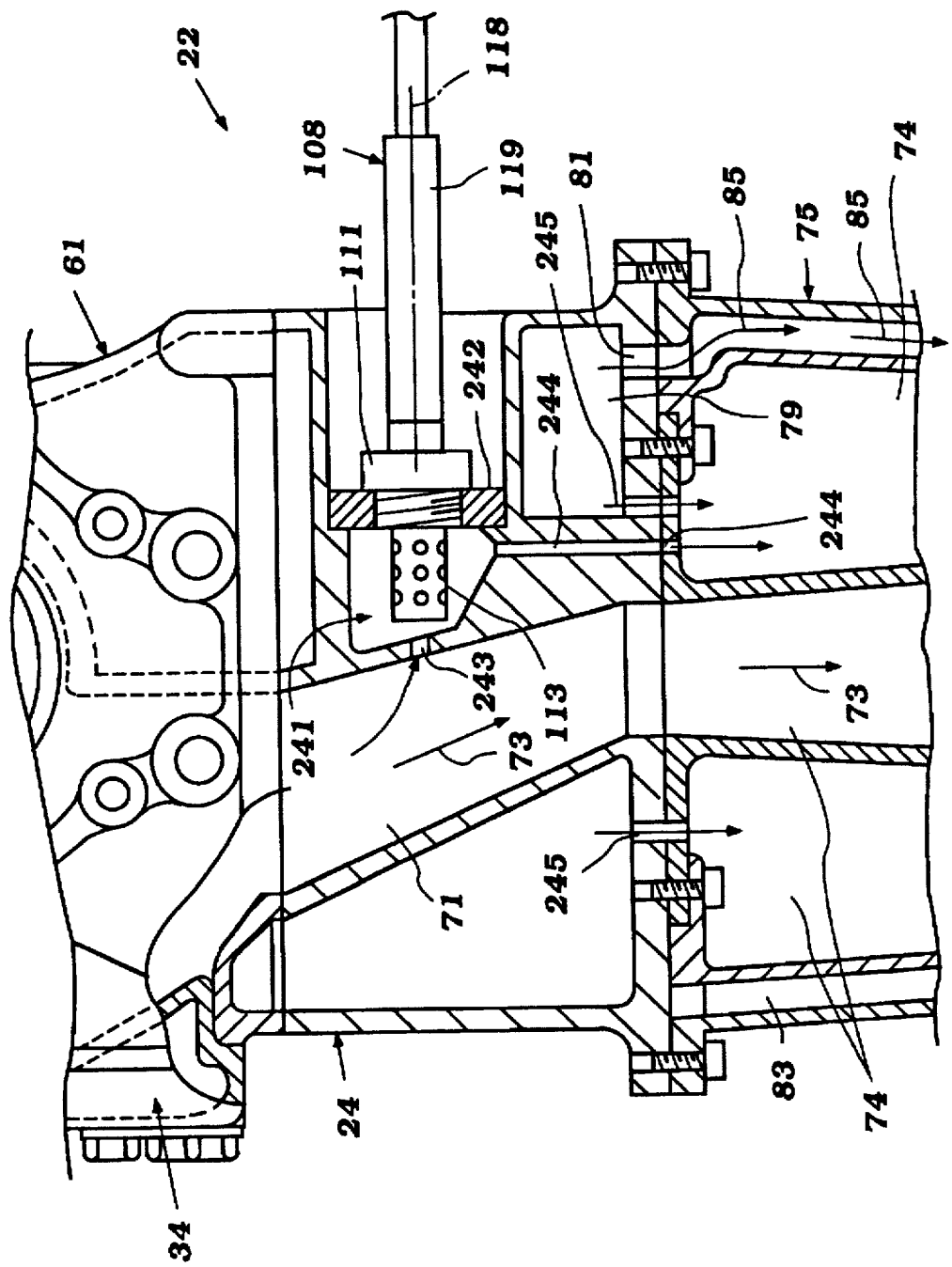
FIG. 23 is a cross-sectional view, taken in the area between the power head and driveshaft housing of an outboard motor constructed in accordance with a yet further embodiment of the invention.

Referring first to the embodiment of FIG. 23, in this embodiment, the guide plate 24 is provided with an integral accumulator chamber 241 which is formed on one side of the exhaust passage 71 therethrough. This defines a volume into which the sensor element and its surrounding protective sleeve 113 passes. This chamber 241 is closed by a mounting plate 242 onto which the fitting 111 of the sensor element log is threaded so as to provide a good support and yet one that would be well insulated. The sensor element 109 is not shown in this figure, but it may be the same as that shown in FIG. 7.

The accumulator chamber 241 communicates with the exhaust passage 71 through an opening 243. Thus, exhaust gases can flow into the accumulator chamber 241 through the opening 243.

A smaller vertically downwardly extending passage 244 extends through the guide plate 24 and into the exhaust expansion chamber 74 so that the exhaust gases may discharge. Also, this configuration permits any liquid which may condense in the accumulator chamber 241 also to drain into the expansion chamber 74.

This figure also shows small water drain openings 245 that extend from the spacer plate cooling jacket 79 into the expansion chamber 74 so that some water will be mixed directly with the exhaust gases and thus provide additional silencing and cooling therefor.

Figure 24:
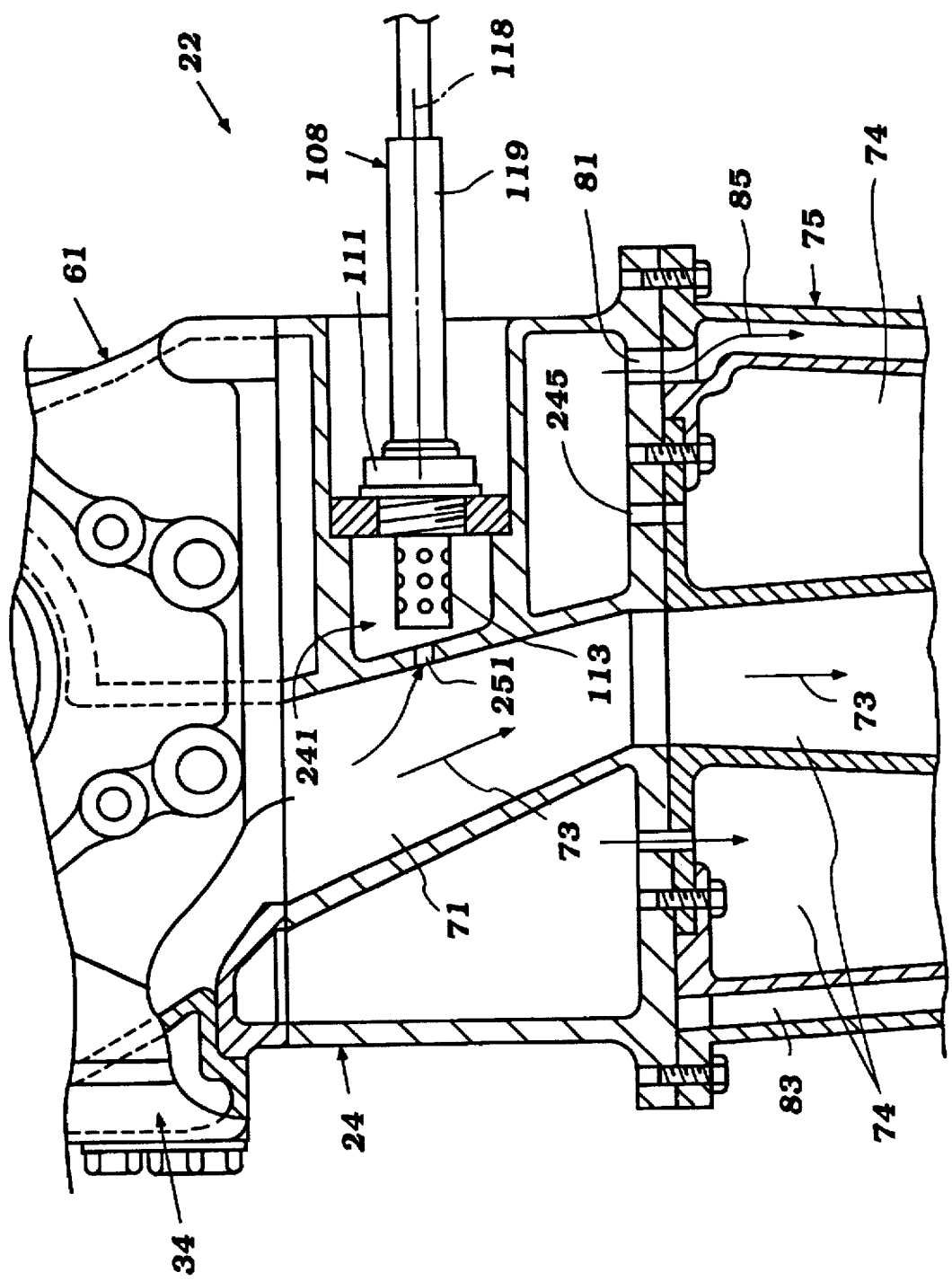
FIG. 24 is a cross-sectional view, in part similar to FIG. 23, and shows yet another embodiment of the invention.

FIG. 24 shows another embodiment which is basically the same as the embodiment of FIG. 23. This embodiment, however, lacks the drain passage 244 and provides a smaller communicating port 251 that communicates the accumulator chamber 241 with the guide plate exhaust passage 24.

Figure 25:
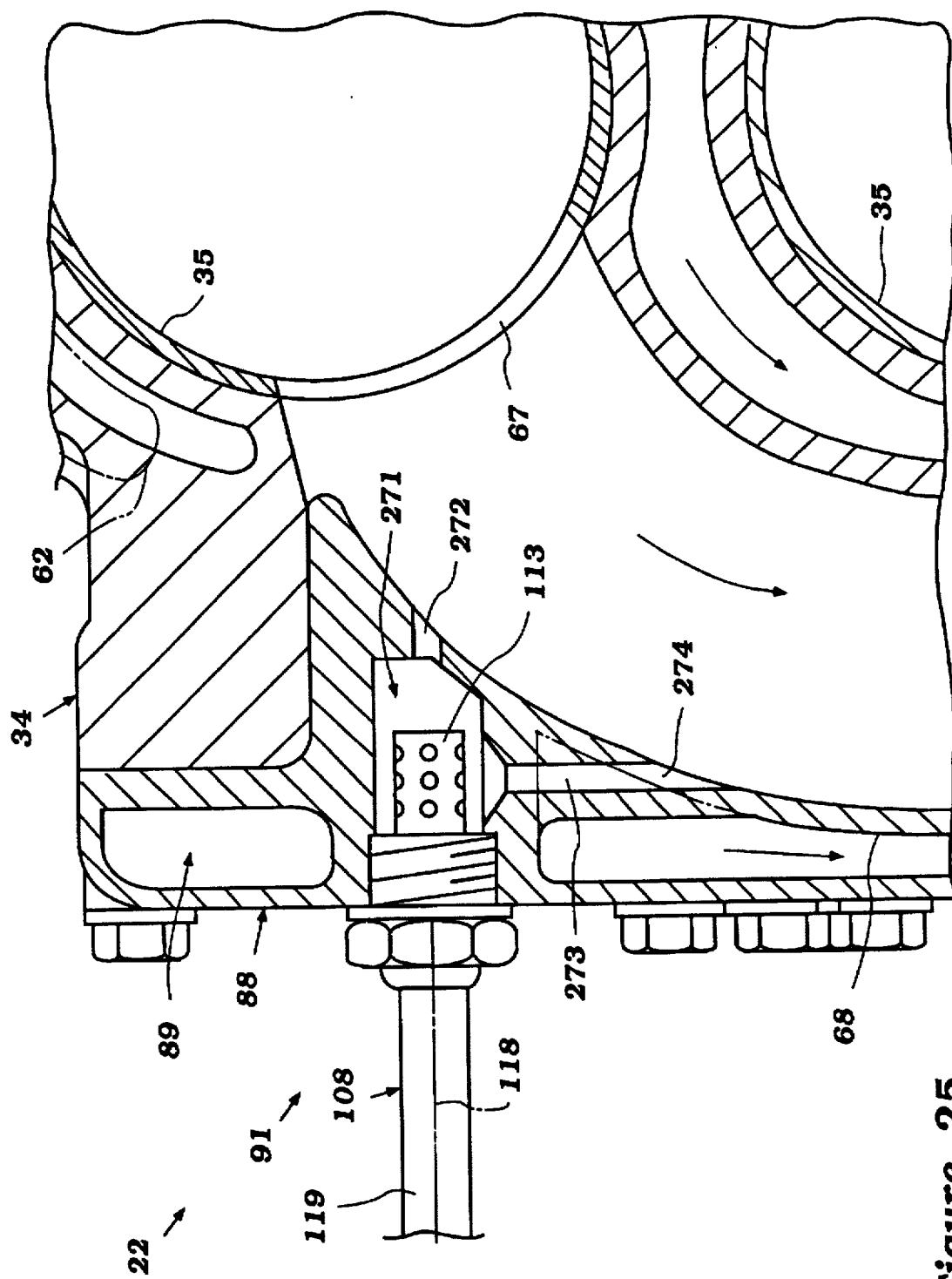
FIG. 25 is an enlarged cross-sectional view, in part similar to FIGS. 4, 11, 13, 16, 19 and 22 of still another embodiment of the invention.

Another mounting arrangement for the sensor 108 is shown in FIG. 25, and in this embodiment, the engine exhaust cover plate 88 is provided with an integral accumulator chamber 271 which communicates with the exhaust manifold 68 adjacent one of the exhaust ports 67 through a restricted opening 272. Again, the construction of the sensor 108 is the same as that shown in FIG. 7 and, accordingly, this structure will not be described again.

This embodiment also employs a drain and discharge passageway 273 that has a discharge end 274 formed in the exhaust manifold 68 and which will create a pressure difference for flow through the accumulator chamber 271 and will also permit liquids to drain away from the sensor element 109.

Next will be described a series of embodiments which are generally the same as the embodiment of FIGS. 1–10 in that the accumulator chamber 107 communicates with two cylinders of the engine but with different timing so as to promote a one-way flow through the accumulator chamber 107. The connected cylinders in these embodiments are different from those shown in the embodiment of FIGS. 1 and 10, but because this is the only difference in the basic engine construction and connection of the elements, those elements which are the same or substantially the same as those previously described have been identified by the same reference numerals and will be described again only insofar as is necessary to understand and practice these embodiments.

In addition to the aforenoted difference, these embodiments also incorporate an arrangement for ensuring against contamination of the exhaust sensor 109 and other improvements in the sensor unit 91 itself.

Figure 26:
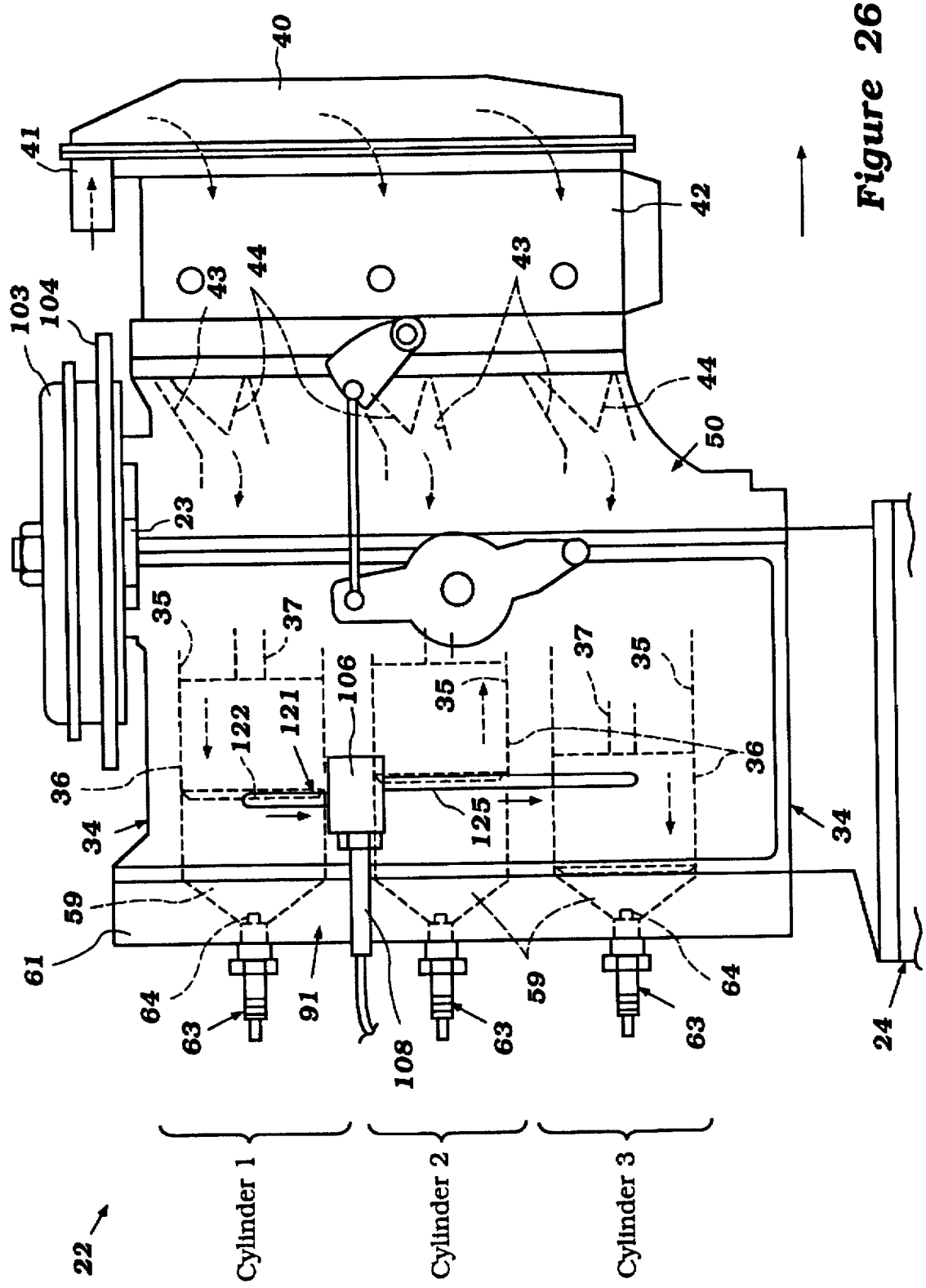
FIG. 26 is an enlarged side elevational view, in part similar to FIGS. 2, 12, 14, 17 and 21 of a still further embodiment of the invention.
Figure 27:
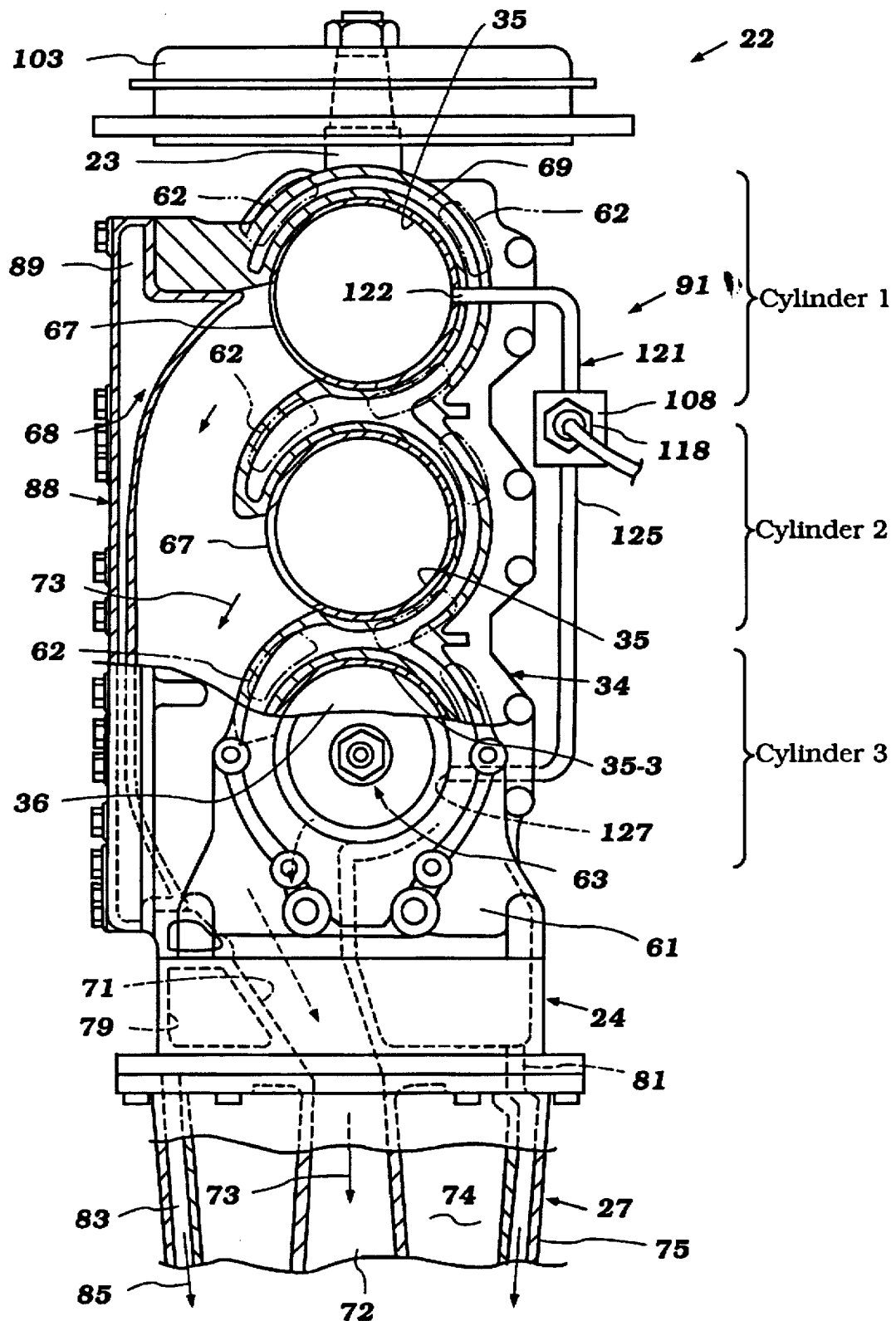
FIG. 27 is a rear elevational view, with a portion broken away, in part similar to FIGS. 4, 11, 13, 16, 19, 22 and 25 for this embodiment.
Figure 28:
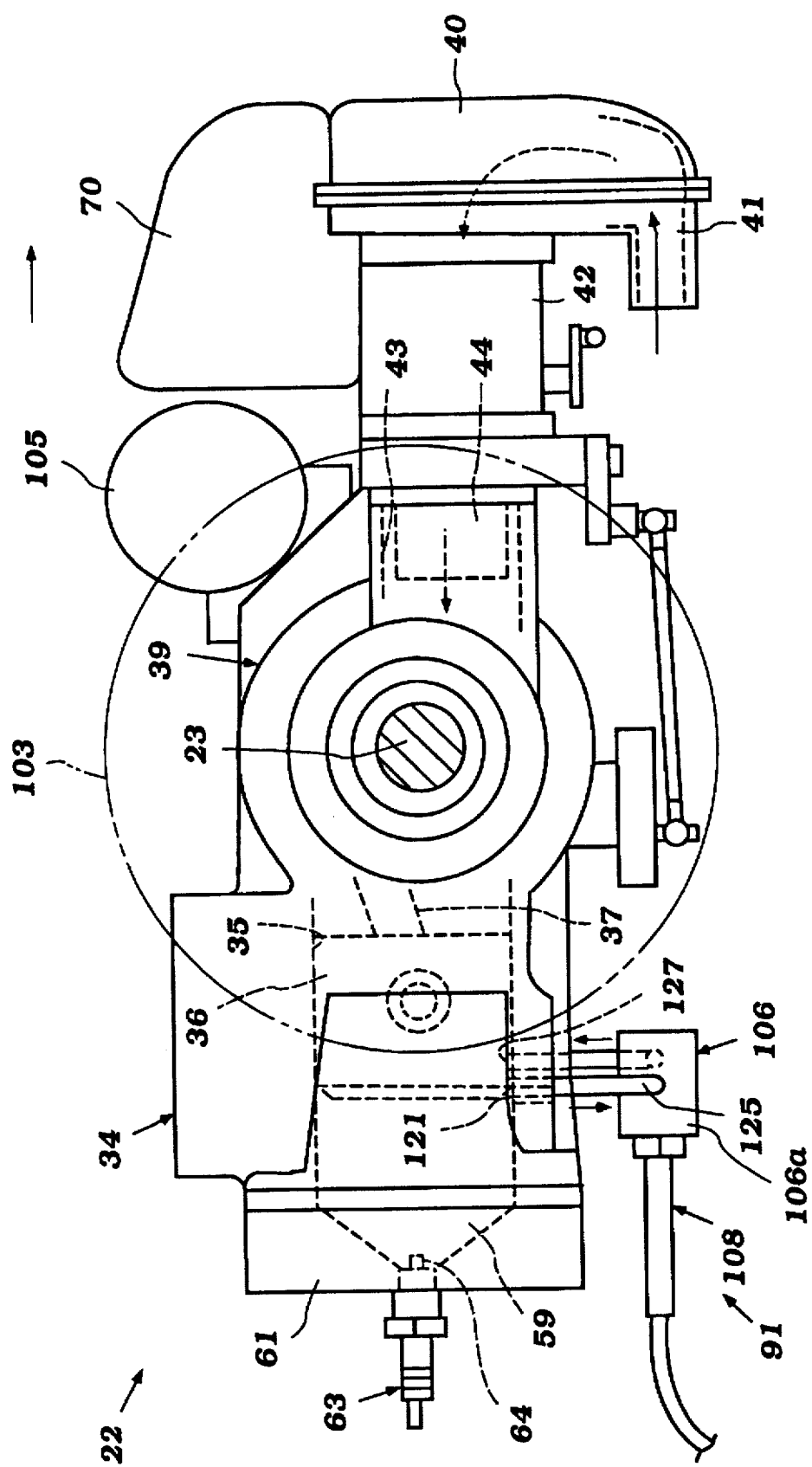
FIG. 28 is a top plan view of this embodiment.

Referring first to the embodiment of FIG. 26, it will be seen that the inlet conduit 121 that supplies exhaust gases to the sensor 91, and specifically the accumulator chamber 107 thereof, extends from no. 1 cylinder. Therefore, the inlet port 122 is disposed so that it will be located at a point in the cylinder bore 34-1 that is disposed immediately adjacent the top edge of the exhaust port so that it will open and close at substantially the same timing as the opening and closing of the respective exhaust port 37-1.

Figure 30:
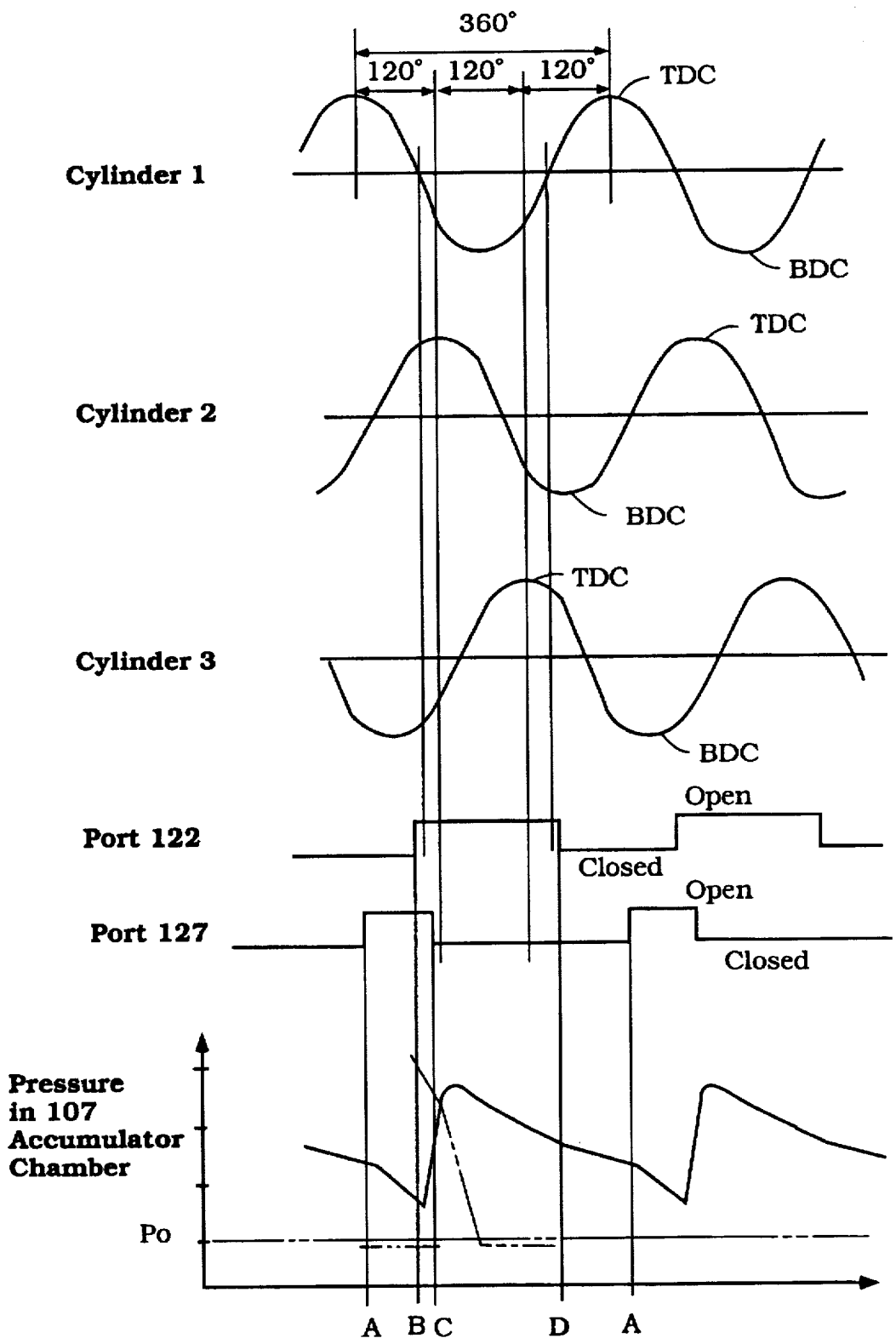
FIG. 30 is a graphical view, in part similar to FIG. 10, showing the operation of this embodiment.

The return passage 125 extends to the cylinder bore 34-3 of cylinder no. 3 and is disposed so as to be opened and closed later in this cylinder cycle than the inlet opening 122. These openings are at slightly different phases than the previously described embodiment and, for that reason, the opening and closing will be described by reference to FIG. 30. In the embodiment of FIGS. 1–10, cylinders 2 and 1 were 120° out of phase from each other, and thus, there was the relationship between the port openings of the ports 122 and 127, as shown in FIG. 10. Basically, the same relationship exists between the cylinders 1 and 3 in this embodiment where the port openings 122 and 127 are also shown.

As may be seen, starting from the point A, when the inlet port 122 and cylinder bore 34-1 is closed because the piston is still moving downwardly from its top dead center position, the port 127 in the cylinder no. 3 will be open and pressure will fall off in the chamber 107.

This fall off in pressure occurs until the point B when the port 122 is opened by the downward movement of the piston 36-1 in the cylinder bore 35-1 when both the exhaust port first opens. Hence, pressure will build up rather rapidly up to the point C when the port 127 moves to its closed position. At the same time, the pressure at the port 122 will begin to decrease because of the opening of the exhaust port and the pressure will fall off to the point D. As with the previously described embodiment, the actual measurement by the sensor takes place in this time period (C to D).

Figure 29:
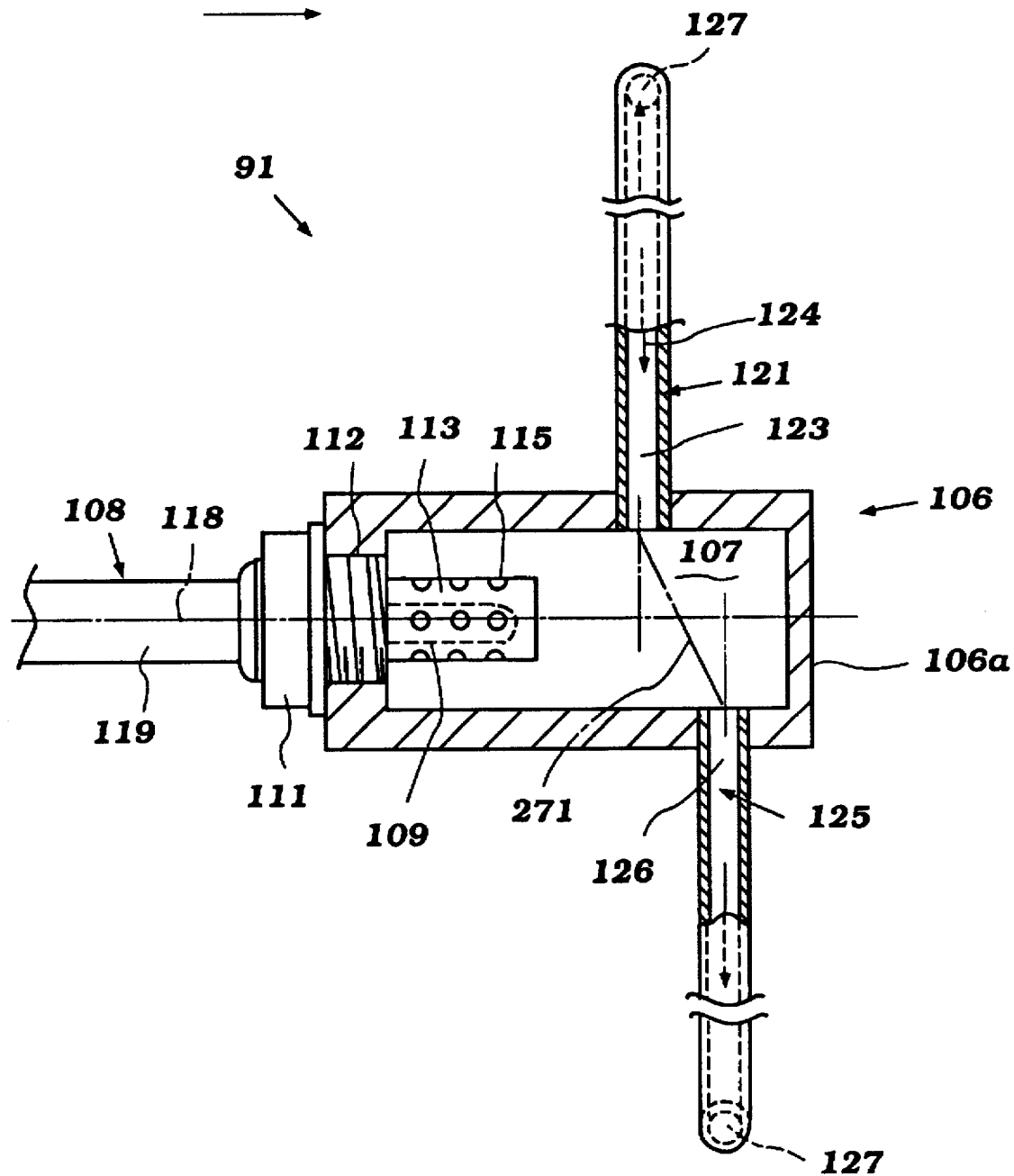
FIG. 29 is an enlarged cross-sectional view of the sensor arrangement for this embodiment.

As may be seen from FIG. 29, in this embodiment, the inlet port 123 is disposed at a greater distance from the sensor 109 than the earlier embodiment. In addition, the gases must flow at an angle, as shown by the line 271, to the outlet port 126. This movement is away from the sensor 109 and thus the sensor will be protected against impingement from foreign particles and lubricant in the combustion gases. In addition, any liquids that may condense in the accumulator chamber 107 can drain out of the opened port 126 down to the lowermost cylinder so as to avoid a build-up of contamination in the accumulator chamber. Thus, this embodiment provides the same advantages of the embodiment of FIGS. 1–10, but also the further advantage of better protection from contamination of the sensor 109.

Figure 31:
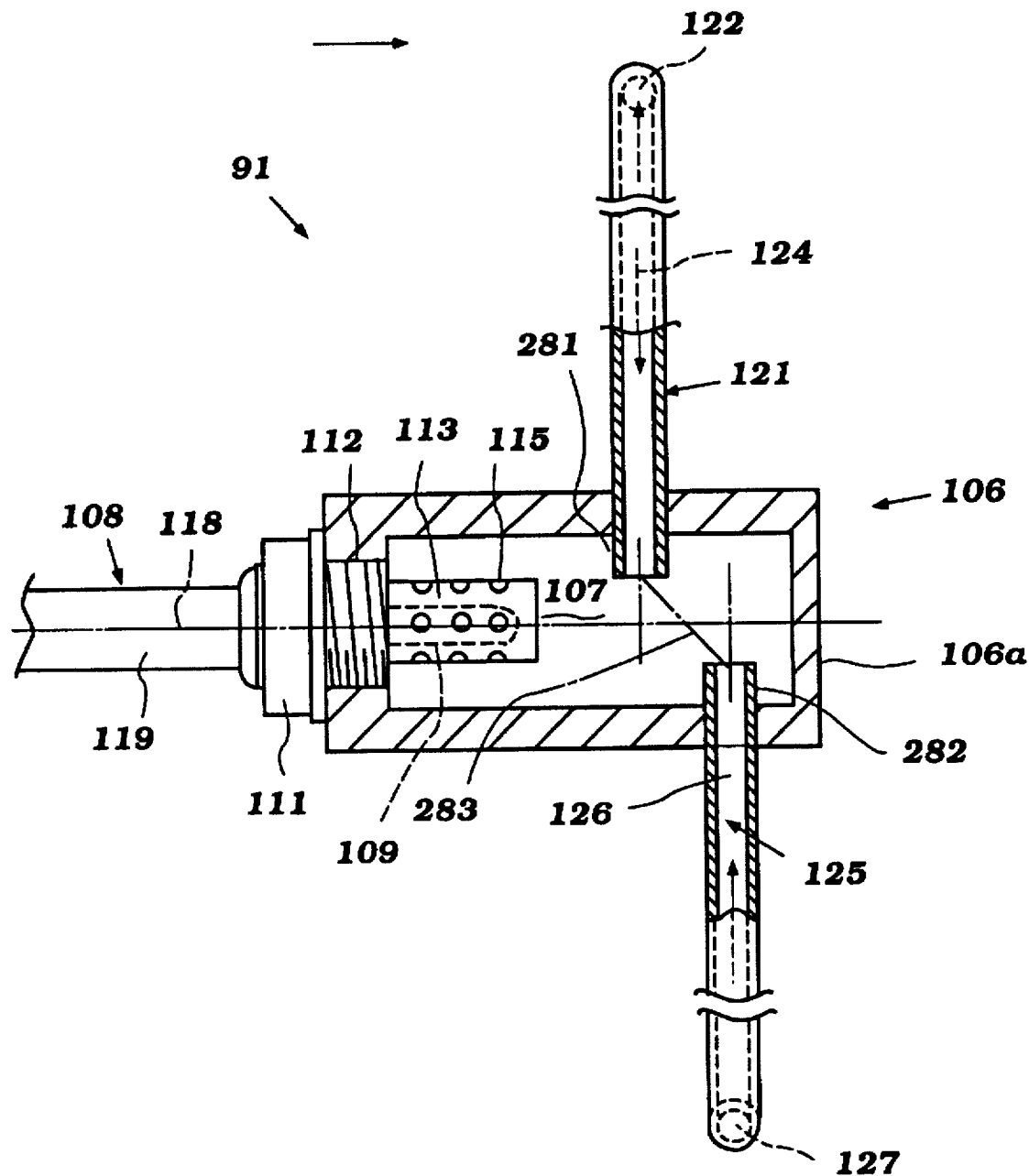
FIG. 31 is a cross-sectional view, taken through a sensor arrangement constructed in accordance with yet another embodiment of the invention.

FIG. 31 shows another embodiment of the invention, where both the inlet conduit 121 and discharge conduit 125 are extended so as to protrude in part into the accumulator chamber 107. These extending portions are indicated by the reference numerals 281 and 282, respectively. As may be seen, this causes the flow path 283 to be more acute and assist in separation due to the circuitous path that must be followed. In addition, this tends to further protect the sensor 109 from contamination.

Figures 32, 32A:
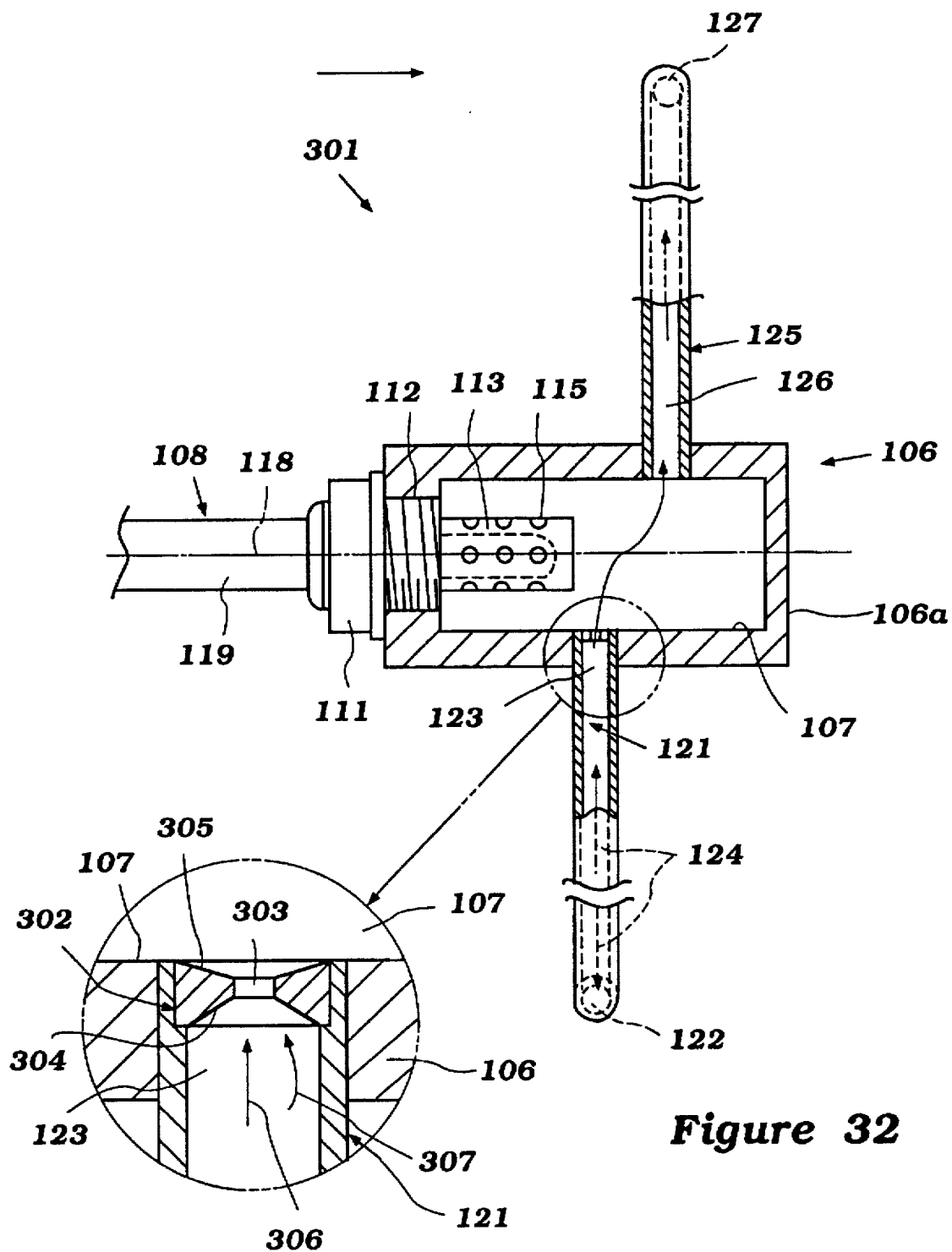
FIG. 32 is a view, with a portion broken away and shown in section, of a sensor constructed with still another embodiment of the invention, and is in part similar to FIGS. 6, 20, 29 and 31.
Figure 33:
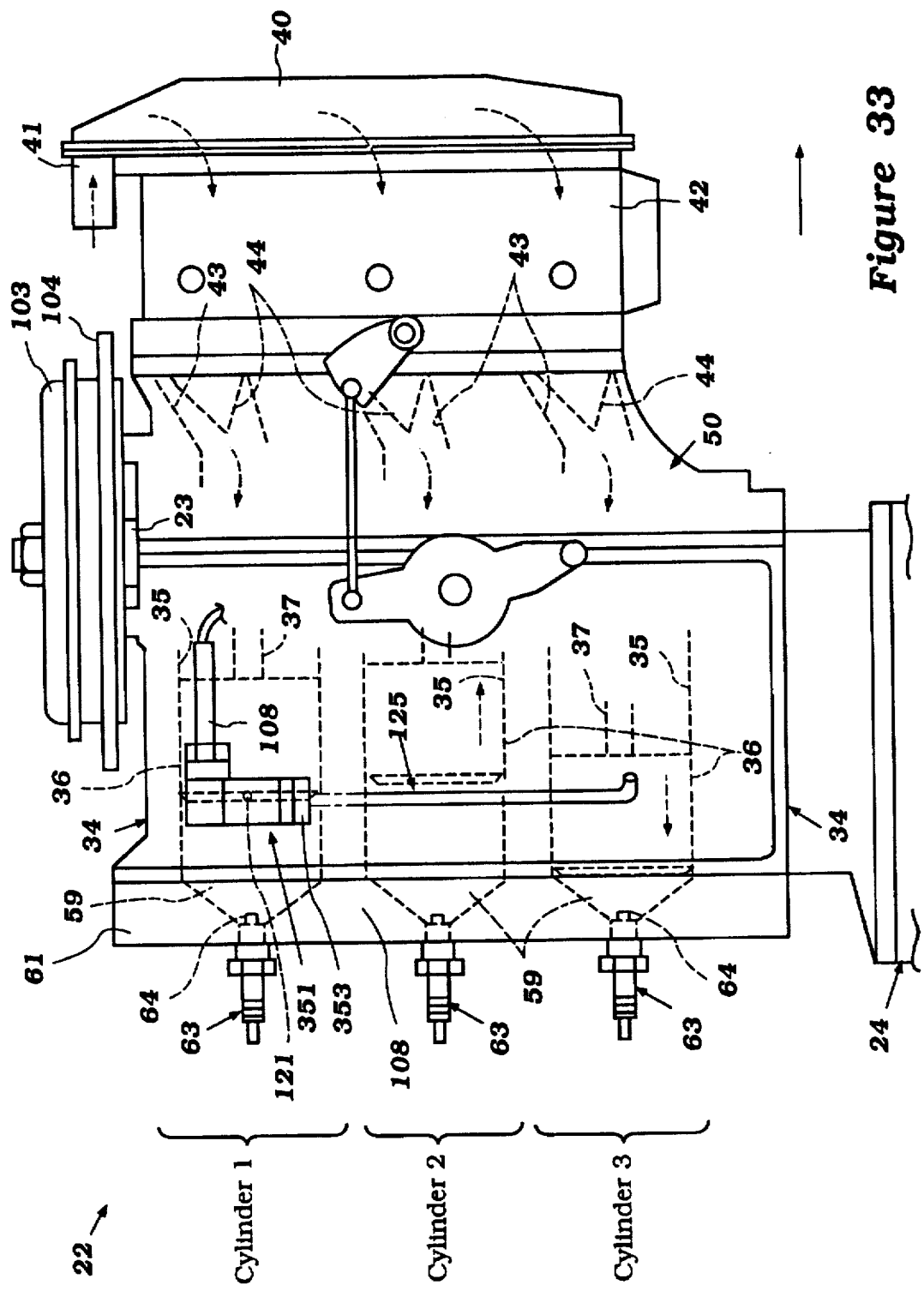
FIG. 33 is an enlarged side elevational view, in part similar to FIGS. 2, 12, 14, 17, 21 and 26, of still a further embodiment of the invention.
Figure 34:
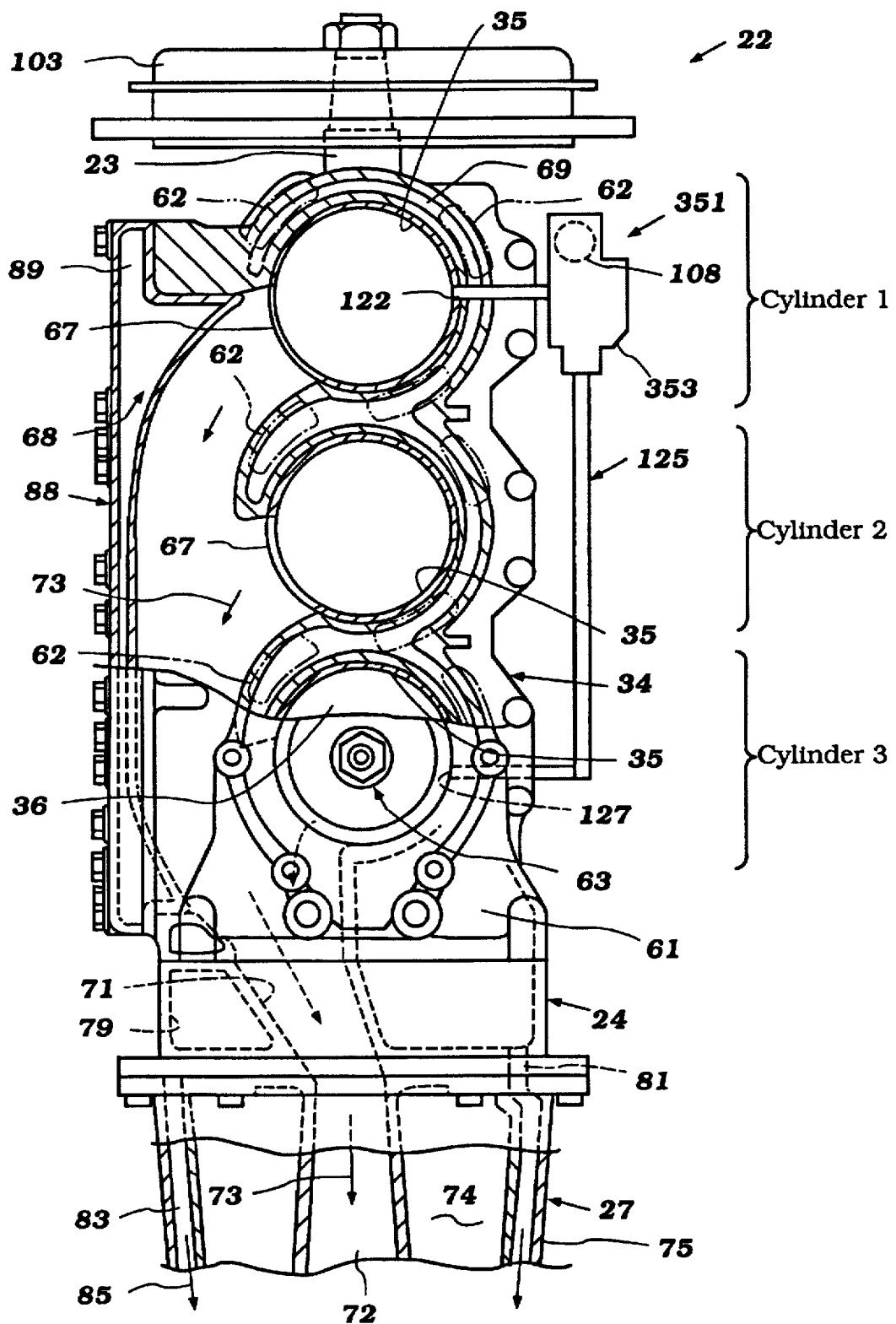
FIG. 34 is a rear elevational view, with portions broken away, in part similar to FIGS. 4, 11, 13, 16, 19, 22, 25 and 27 of this embodiment.
Figure 35:
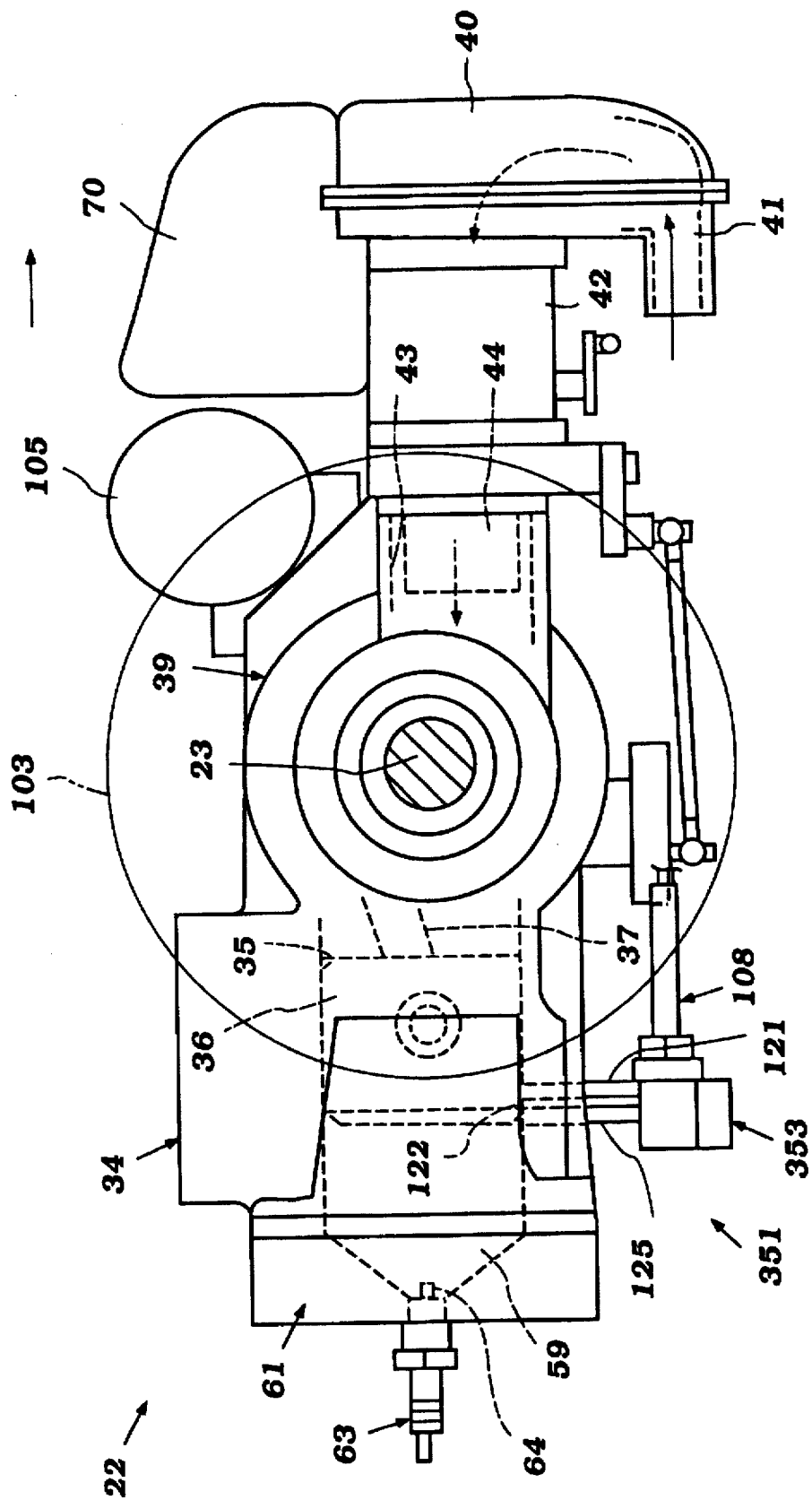
FIG. 35 is a top plan view of this embodiment.

Another sensor configuration that is constructed to protect the sensor element from contamination is shown in FIG. 32 and is identified generally by the reference numeral 301. This sensor 301 has the same basic construction and operation of the sensor of FIGS. 1–10, and which is shown in most detail in that embodiment in FIG. 6. Therefore, where components have the same construction and operation, they have been identified by the same reference numerals employed in that embodiment and will be described again only insofar as is necessary to understand the construction and operation of this embodiment.

It should be noted that this embodiment also reverts to the cylinder no. 2 to cylinder no. 1 connection of the embodiment of FIGS. 1–10, as opposed to the cylinder no. 1 to the cylinder no. 3 connection of the embodiment of FIGS. 26–30 and 31.

In this embodiment, protection is provided by placing an orifice plate, indicated generally by the reference numeral 302, at the discharge end 123 of the conduit 121 where it enters the accumulator chamber 107. This control orifice 302 has a restricted central opening 303 defined at the pair of conical sections 304 and 305 which in effect provide a convergent/divergent nozzle. Therefore, the flow along a path 306 will cause some of the air to be turned, as shown at 307, which will tend to reduce the likelihood that oil particles having larger inertia can enter the accumulator chamber 107. Thus, this slows down the flow and provides further assurance that the sensor 109 will not be contaminated.

FIGS. 33–37 show a still further embodiment of the invention which connects the sensor, indicated generally by the reference numeral 351 in this embodiment, with the engine in the same manner as with the embodiment of FIGS. 27–30. Because of that similarity, the basic engine and its association with the sensor will not be described again, and the same reference numerals have been applied so as to facilitate the understanding of the operation of this embodiment without necessitating a further description of components which have already been described.

In this embodiment, the sensor 351 is constructed in a way so as to further protect the exhaust sensing element, indicated generally by the reference numeral 108, and which has a construction substantially the same as that shown in FIG. 7. However, the protective device is constructed in a different manner, and it is comprised of an outer housing assembly, indicated generally by the reference numeral 352, and which includes a first housing piece 353 which defines a first chamber 354. The conduit 121 has an extending portion 355 which extends into the chamber 354 and which has a plurality of perforate openings 356 which communicate the discharge end 123 with the chamber 354.

The end of the extending portion 356 is received in a counterbore 357 formed adjacent the inner end of the chamber 354 and from which a U-shaped passage 358 extends. The passage 358 terminates in a counterbore 359 in which the inlet end 126 of the conduit 125 is press fit.

The chamber 354 is formed by a bore 361 that receives a closure plug 362 which is fitted around the inlet tube extension 355.

The sensor assembly 108, and specifically its outer protecting sleeve 113, which has the openings 115, extends into a further accumulator chamber 363 formed by an opening 364 in the housing piece 352 and which is closed by a closure plug 365. A small orifice 366 communicates the accumulator chamber 364 with the accumulator chamber 354. These two chambers and, in fact, either one of them, has a volume that is more than one-half of the volume of the sensor element 109 itself.

The orifice 366 is surrounded by a conical surface 367 so that any lubricant which may enter the accumulator chamber 363 through the orifice 365 will condense, collect and drain back into the accumulator chamber 354.

In a similar manner, a drain port 368 is formed in the lower wall 361 of the accumulator chamber 354 and communicates with the conduit opening 359. The lower surface of this drain opening 368 is also formed with a conical surface 369 so as to assist in the assurance that lubricant or other foreign materials cannot damage the sensor assembly 109.

Figure 37:
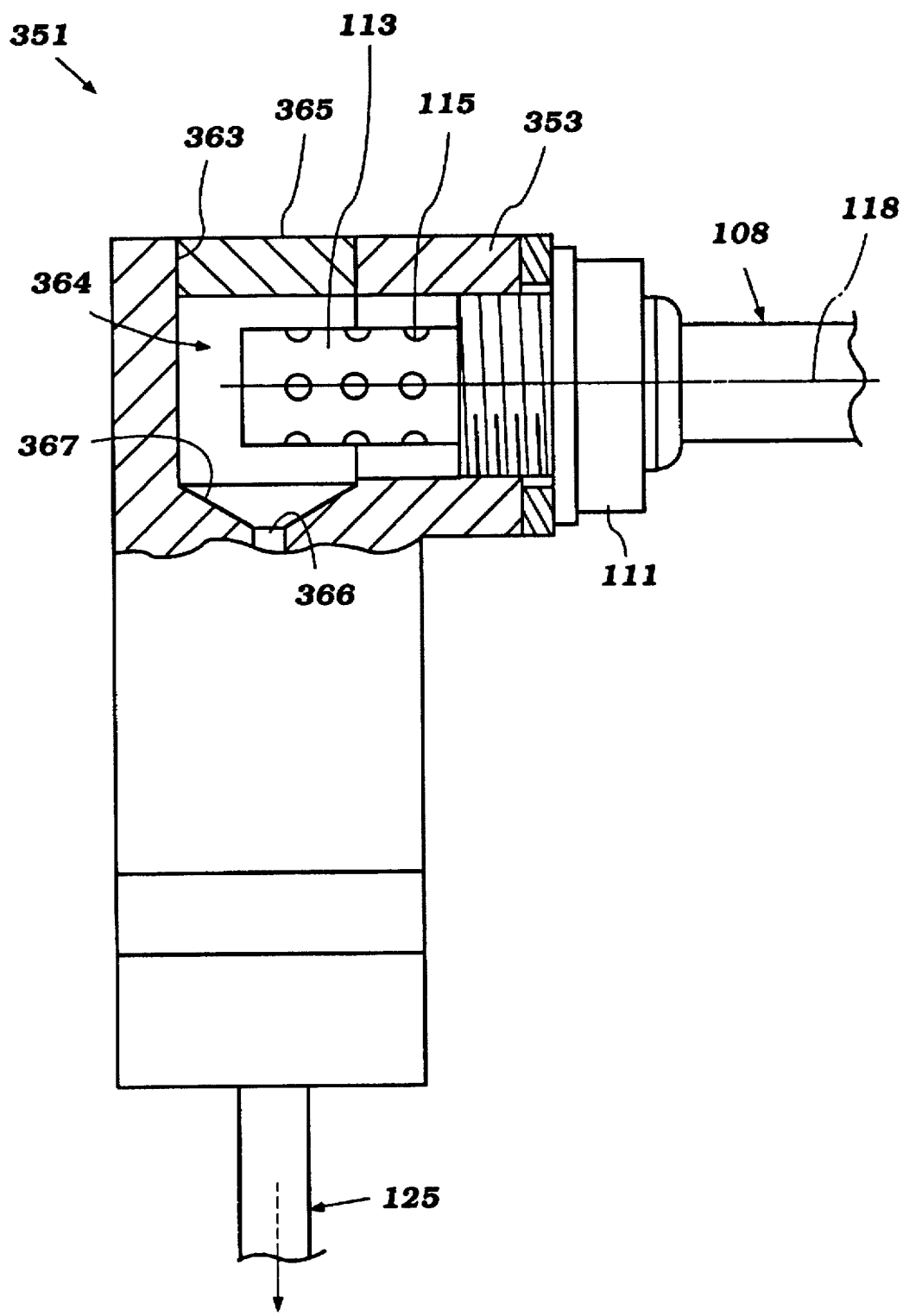
FIG. 37 is a view looking from the direction perpendicular to that of FIG. 36, and shows how the sensor element is mounted in this embodiment.
Figure 38:
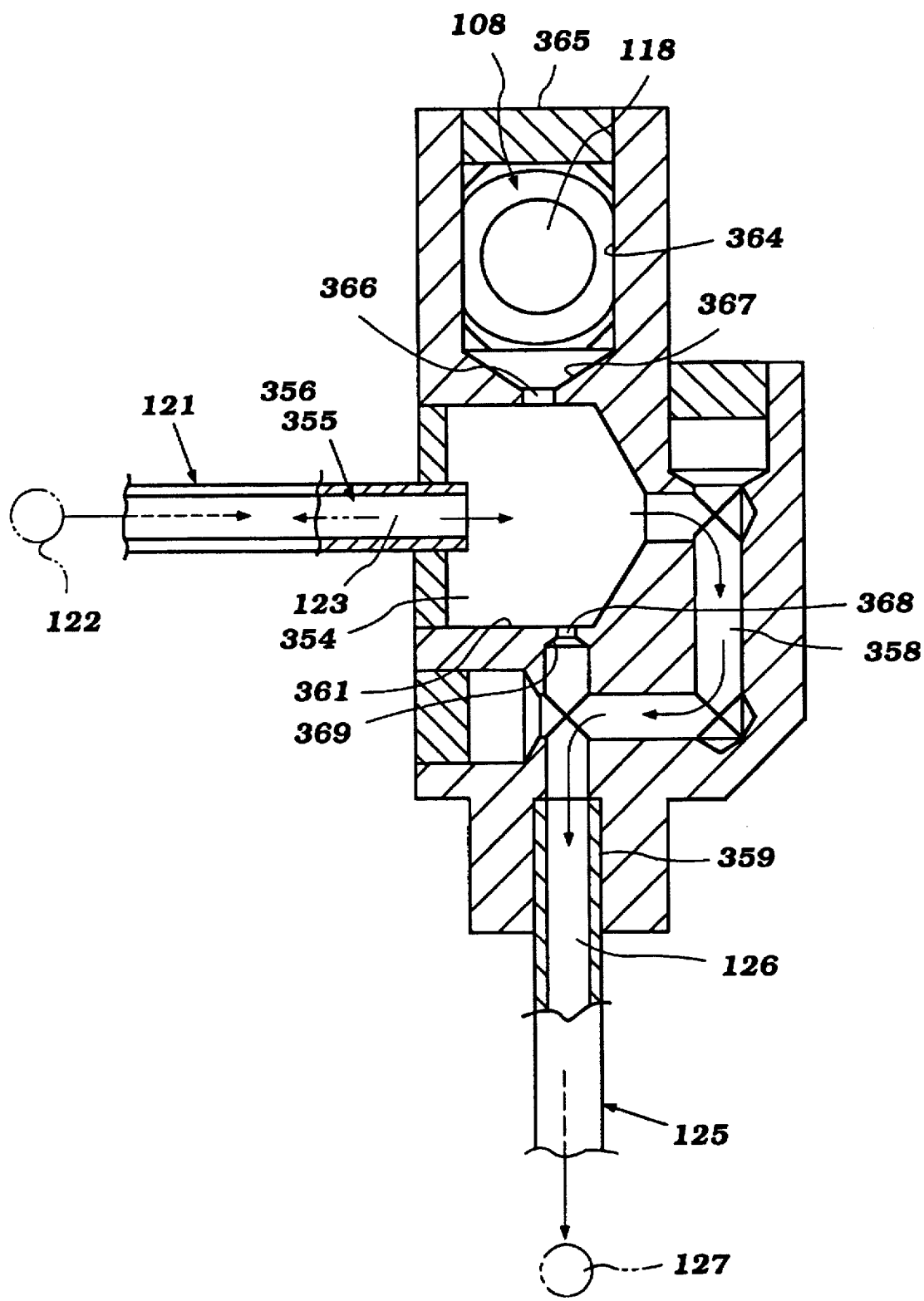
FIG. 38 is a cross-sectional view, in part similar to FIG. 36, and shows a further embodiment of a sensor.

A sensor arrangement constructed in accordance with another embodiment is illustrated in FIG. 38. This embodiment differs from the embodiment of FIGS. 36 and 37 only in that the conduit 125 is not provided with the extension 355 or the apertures 356 and thus freely communicates with the chamber 354. However, this still provides the circuitous flow path and the protection of the sensor 108 from foreign contaminants. Because of its other similarities to the earlier embodiment, it is believed that a further description of this embodiment is not necessary to permit those skilled in the art to practice the invention.

Figure 36:
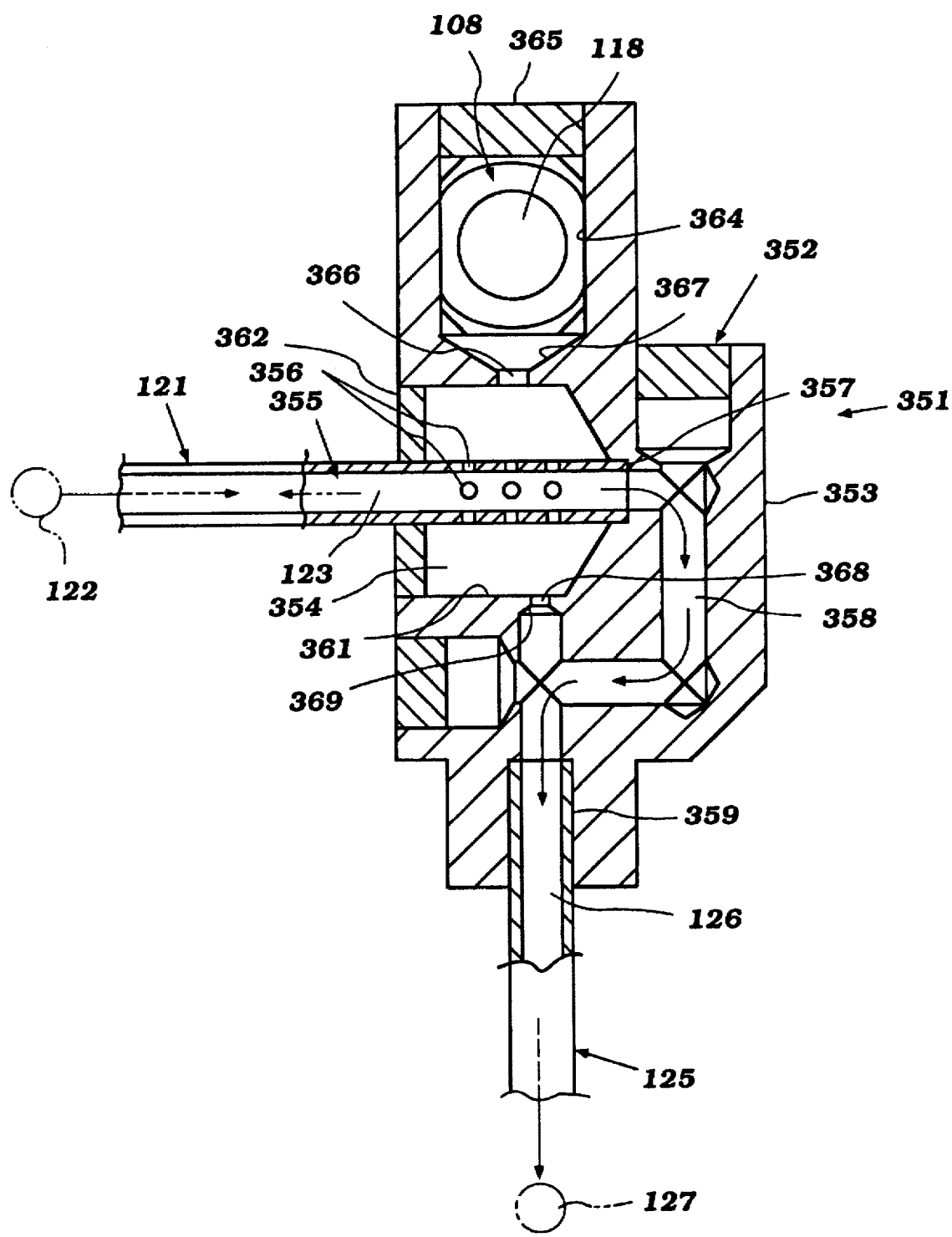
FIG. 36 is an enlarged cross-sectional view, taken through the sensor arrangement of this embodiment.
Figure 39:
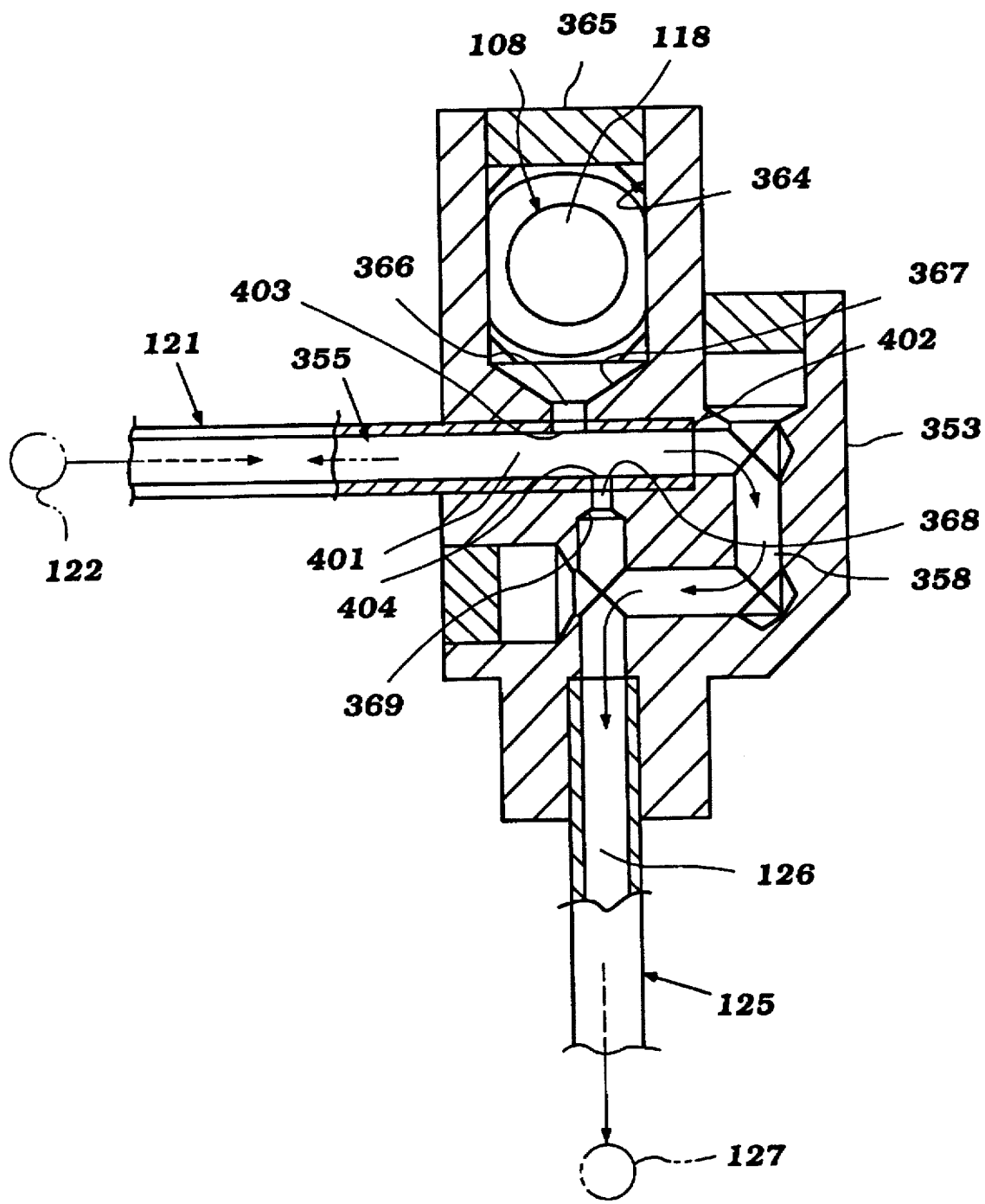
FIG. 39 is a cross-sectional view, in part similar to FIGS. 36 and 37, showing a still further sensor embodiment.

FIG. 39 shows yet another embodiment which is similar to the embodiments of FIGS. 36 and 37 and of FIG. 38. In this embodiment, however, the accumulator chamber 354 is eliminated and the supply conduit 121 has an extending portion 401 that extends through an elongated bore 402 formed in the housing piece 353. A first port 403 extends through once side of the tube to the accumulator chamber 364 in which the sensor 109 is positioned and permits the exhaust gases to flow through this and through the restricted passageway 366, as the previously described embodiment.

In addition, a further passageway 404 in the tube end 401 communicates with the drain passageway 368 for return of drained or accumulated fluids. Again, the volume of the accumulator chamber 364 is substantially greater than half of the volume displaced by the sensor 109.

Figure 40:
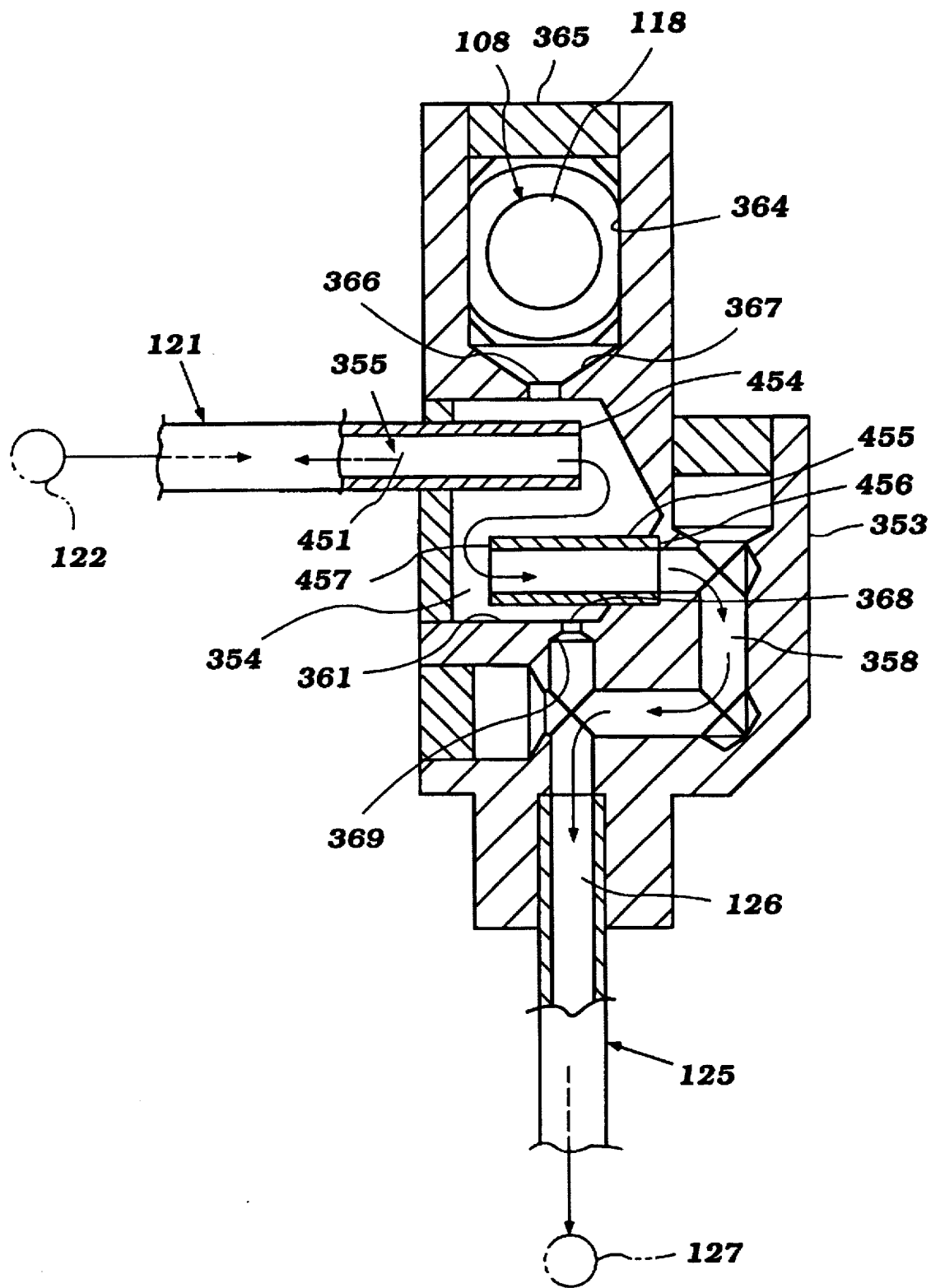
FIG. 40 is a cross-sectional view, in part similar to FIGS. 36, 38 and 39, of a still further sensor embodiment.

FIG. 40 shows another embodiment which is similar to the embodiments of FIGS. 36 and 37, FIG. 38 and FIG. 39. This embodiment employs the accumulator chamber 354 as the embodiments of FIGS. 36 and 37 and 38, but incorporates a further arrangement for providing a circuitous flow path therethrough that will help in the separation of lubricant and other foreign contaminants. Thus, the inlet conduit 121 is formed with an extending portion 451 that terminates at an end 452 in the chamber 354 which is spaced from the restricted opening 366 which communicates the accumulator chamber 354 with the accumulator chamber 364.

In addition, a discharge tube 455 is pressed into a counterbore 456 in the housing piece 353 and has its inlet end 457 spaced from and offset from the outlet end 454 of the conduit extension 451. As a result, there will be a circuitous flow path that will assist in the separation.

Figure 41:
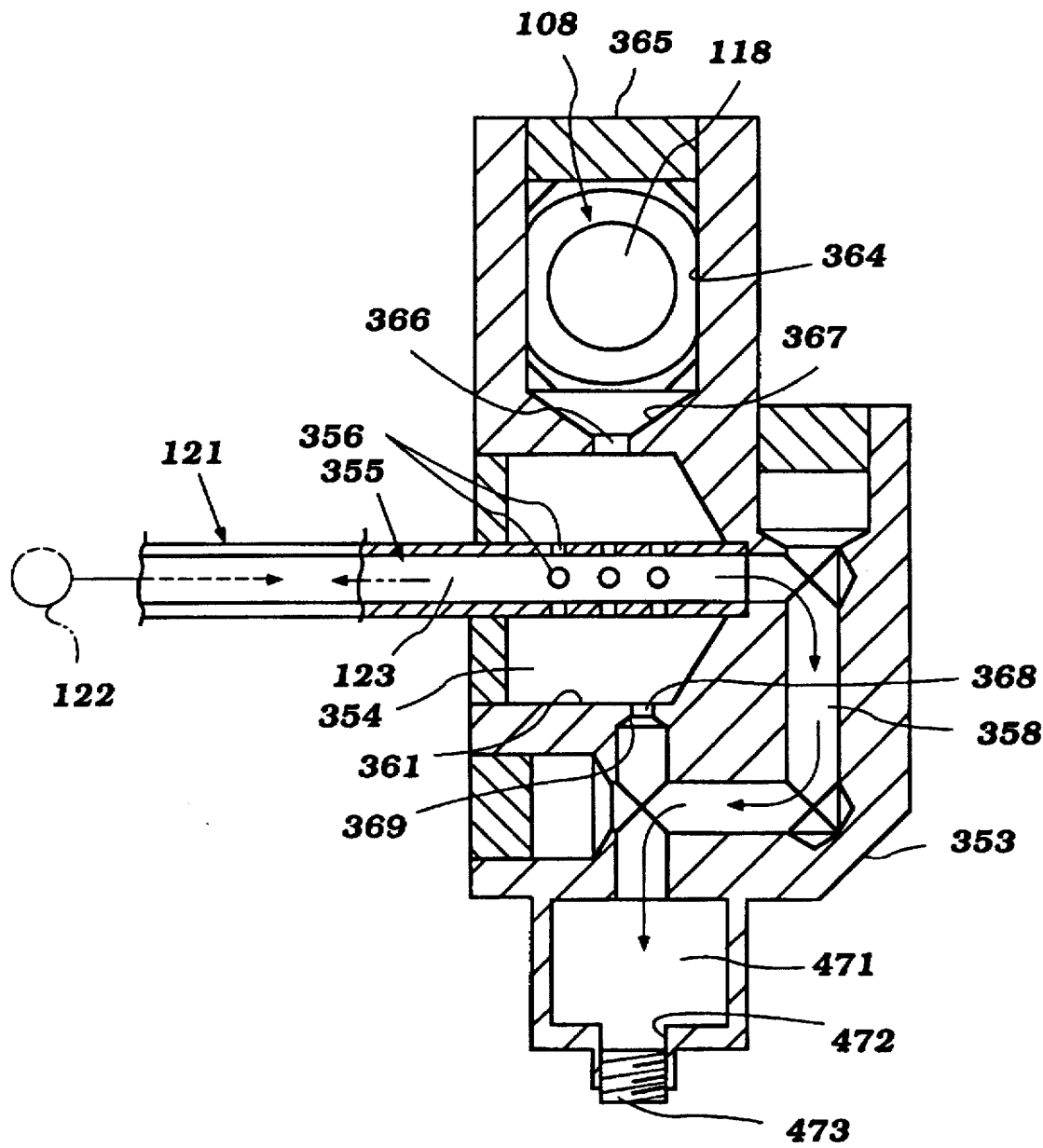
FIG. 41 is a cross-sectional view, in part similar to FIGS. 36, 38, 39 and 40, of a still further embodiment of the invention.

FIG. 41 illustrates an embodiment which is basically the same as the embodiment of FIGS. 36 and 37. Therefore, the components of this embodiment which are the same as that embodiment have been identified by the same reference numerals and will not be described again.

In this embodiment, the housing piece 353 is provided with a drain accumulation chamber 471 into which the gases flow from the passage 358 and also from the drain opening 368 and chamfered surface 369. The lower portion of the drain chamber 471 is provided with a drain opening 472 normally closed by a fitting 473. The fitting 473 may be removed for draining of accumulated fluids. The other cylinder of the engine (cylinder no. 3 in this embodiment) communicates with the drain chamber 471 or some other area upstream of the drain chamber 471.

The embodiments for protecting the sensor 108 from contamination thus far described have done this by primarily mechanical means. Now will be described several embodiments of the invention where this protection is achieved by means in addition to mechanical means. In these embodiments, heat is maintained in the accumulator chamber 107 in a variety of fashions. This provides two purposes. First, the sensor element 109 will be maintained at an elevated temperature and one which keeps it at its operating temperature. As know in this art, most exhaust sensors do not become fully operative until they reach an operating temperature that is relatively high. Thus, by maintaining heat in the chamber 107 and on the sensor element 109, it is possible to ensure good operation of the sensor. In addition, by keeping the temperature high, the likelihood of lubricant condensing in the accumulator chamber 107 is avoided.

Figures 42, 42A:
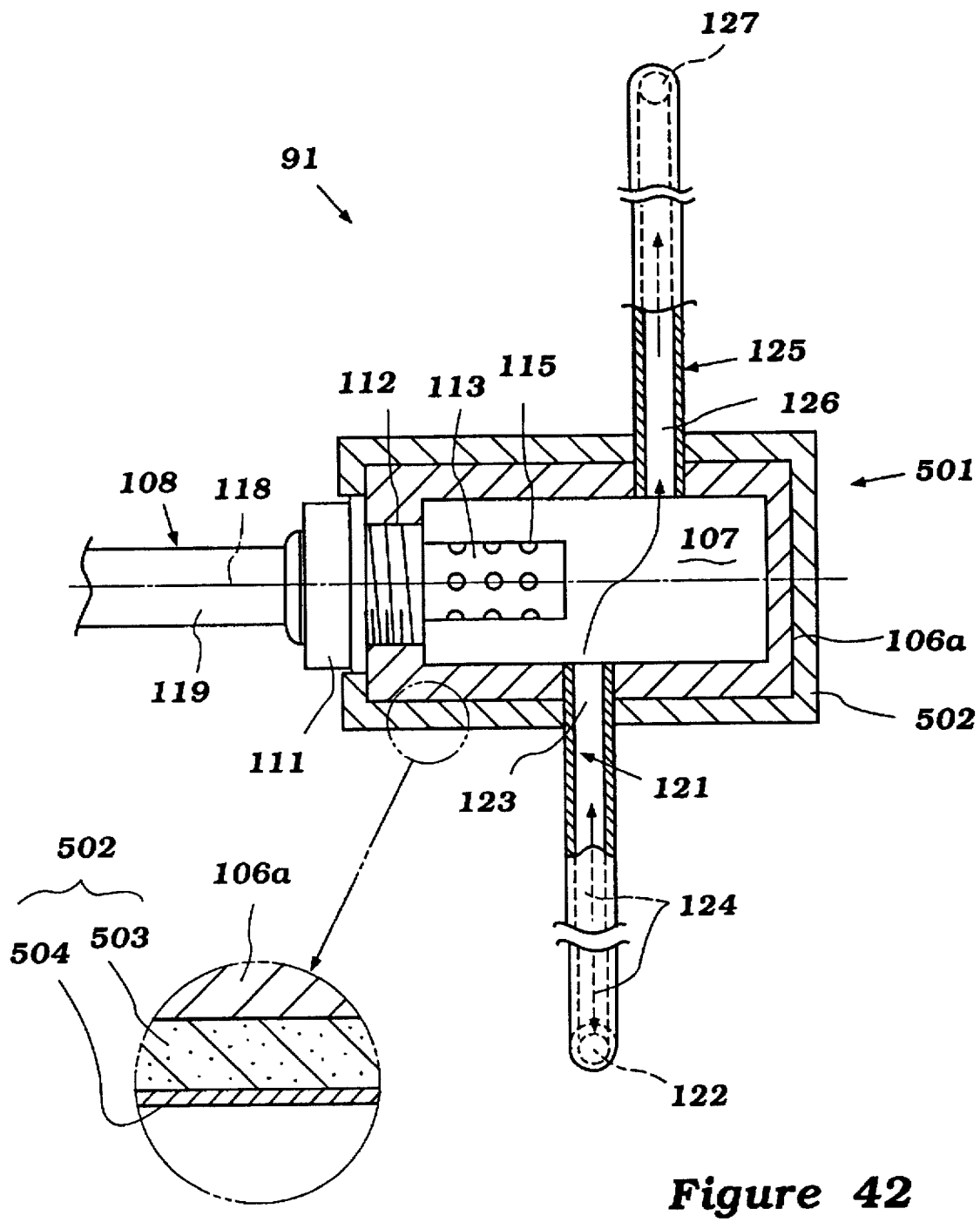
FIG. 42 is a cross-sectional view of another embodiment of the sensor.

Referring first to the embodiment of FIG. 42, the sensor is provided with an insulating outer housing, indicated generally by the reference numeral 501, which surrounds the housing 106 of the embodiment like that shown in FIG. 6, with an insulating layer, indicated generally by the reference numeral 502. As seen best in the enlarged view of FIG. 2, the insulating layer 502 comprises a thick insulating layer 503 formed from a suitable material and a thin protective covering 504. Aside from this, this embodiment operates and functions the same as the embodiment of FIG. 6. For that reason, further description of this embodiment is not believed to be necessary to understand the construction and operation.

Figures 43, 43A:
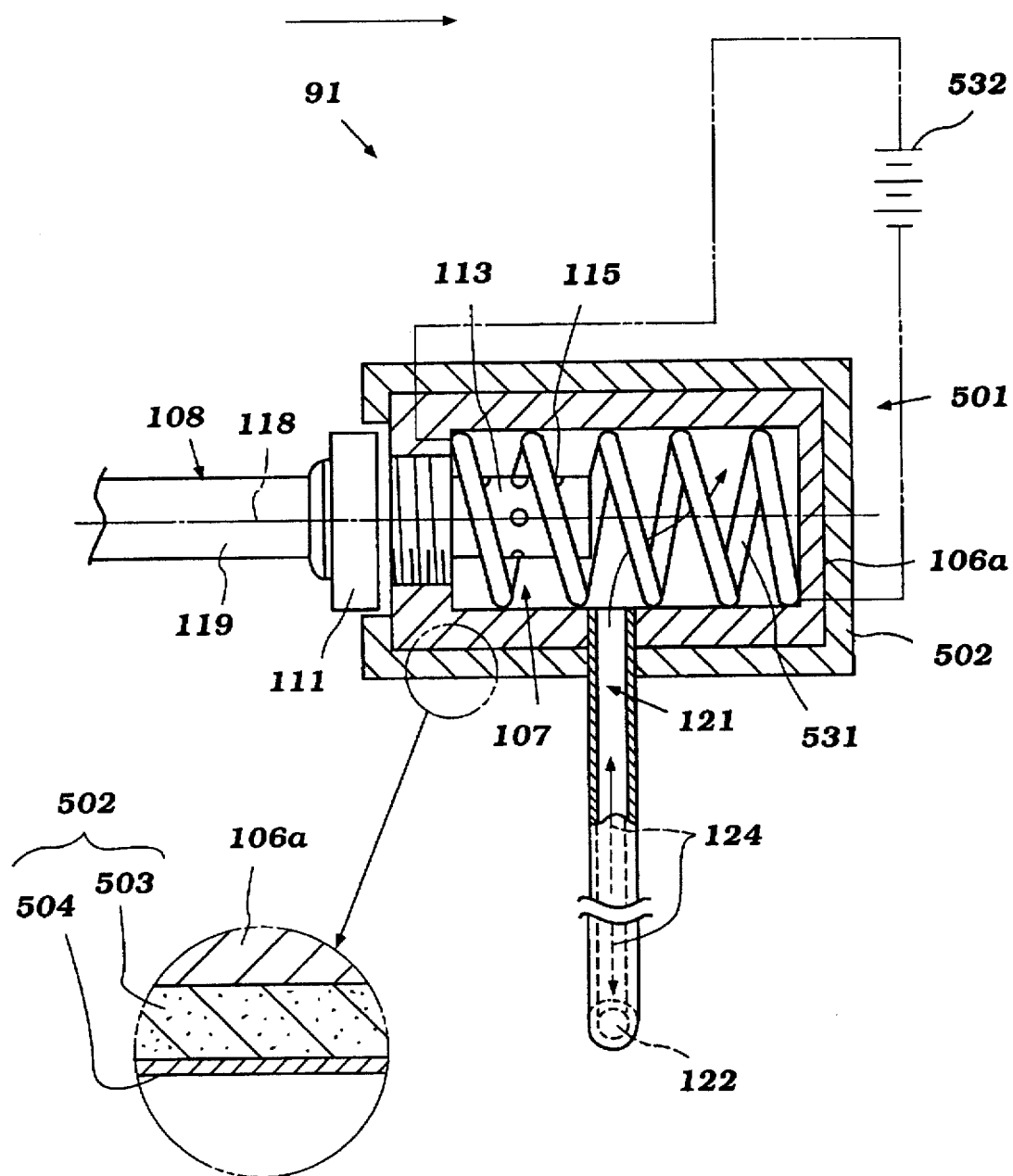
FIG. 43 is a cross-sectional view of a still further sensor embodiment.

FIG. 43 shows another embodiment which is basically the same as the embodiment of FIG. 42. However, this embodiment additionally provides an electrical heating element, indicated by the reference numeral 531, within the accumulator chamber 107. This heating element 531 not only is in heat exchanging relationship with the outer housing 106, but also extends around the sensor 109 and its protective sleeve 113.

The heating element 531 receives electrical power from a battery 532 and thus maintains the elevated temperature so as to provide oil protection and also to maintain a high temperature for good operation of the sensor 108.

Figure 44:
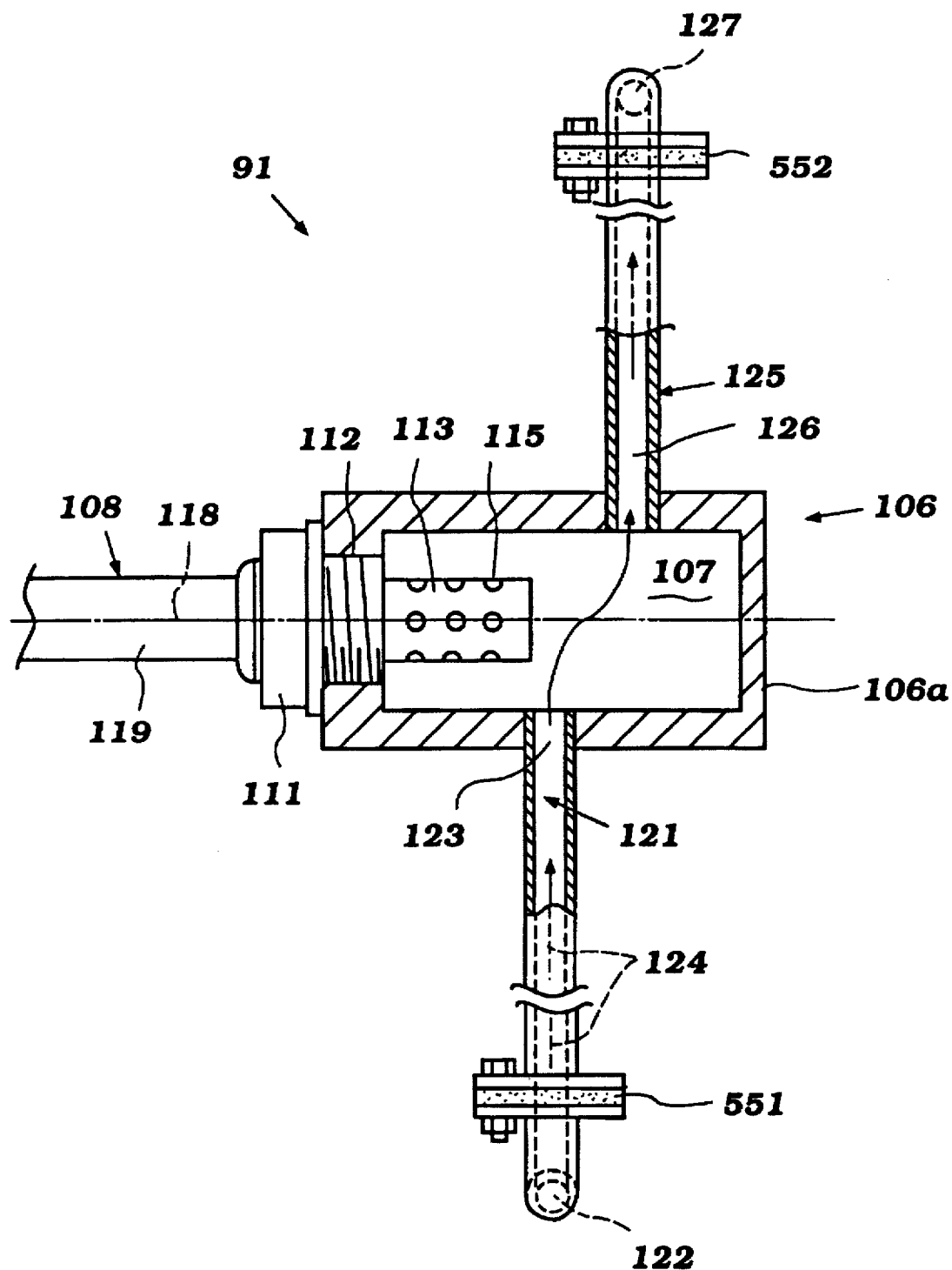
FIG. 44 is a cross-sectional view of another sensor embodiment.

FIG. 44 shows the final embodiment, and this embodiment maintains heat by providing heat insulating couplings 551 and 552 between the conduits 121 and 125 and the adjacent engine structure. Hence, heat in the accumulator chamber 107 cannot be easily transmitted away from the chamber through the metal-to-metal connection of the previously described embodiments.

Thus, from the foregoing description, it should be readily apparent that the described embodiments of the invention not only provide a very effective exhaust sensor that can be utilized with two-cycle engines, but also ensures that the sensor will have a long life and be relatively free of contamination and deterioration in output. Of course, various changes and modifications may be made without departing from the spirit and scope of the invention, as defined by the appended claims.

I claim:

1. A control system for an internal combustion engine having a combustion chamber that varies in volume cyclically during engine operation, an exhaust system for receiving exhaust gases from said combustion chamber during a cycle of engine operation, a fuel supply system for supplying fuel to said engine for combustion in said combustion chamber, an accumulator chamber for providing a volume in which exhaust gases from said combustion chamber may accumulate and communicating with said combustion chamber for at least a portion of the engine operating cycle, a sensor in said accumulator chamber and displacing less than one-half of the volume of said accumulator chamber for providing a control signal for control of said fuel supply system, and protecting means for preventing oil in the exhaust gases from contaminating said sensor.

2. A control system as set forth in claim 1, wherein the accumulator chamber is formed by an outer housing defining a cavity therein into which the sensor protrudes and which outer housing communicates with the combustion chamber.

3. A control system as set forth in claim 2, wherein the sensor has a threaded connection with the outer housing.

4. A control system as set forth in claim 3, wherein a protective screen surrounds the sensor within the accumulator chamber for protecting the sensor from contamination.

5. A control system as set forth in claim 2, wherein the communication of the accumulator chamber with the combustion chamber permits flow into and out of the accumulator chamber.

6. A control system as set forth in claim 5, wherein the flow into the accumulator chamber from the combustion chamber occurs only at the end of the combustion phase.

7. A control system as set forth in claim 6, wherein the engine is a ported engine having an exhaust port and the combustion chamber communicates with the accumulator chamber at a time substantially equal to the time when the exhaust port initially opens.

8. A control system as set forth in claim 7, wherein the communicating means further provides a discharge from the accumulator chamber of the gases to another portion of the engine so that the flow will be basically unidirectional through the accumulator chamber.

9. A control system as set forth in claim 8, wherein the discharge conduit discharges to another portion of the engine related to another combustion chamber.

10. A control system as set forth in claim 9, wherein the other combustion chamber is also formed by a variable volume chamber, the cycle of which varies at a different phase from that with which the accumulator chamber communicates directly.

11. A control system as set forth in claim 10, wherein the conduits communicating the accumulator chamber with the first combustion chamber and the second combustion chamber maintain respectively a longer communication with the first combustion chamber than with the second combustion chamber.

12. A control system as set forth in claim 8, wherein the discharge is to the exhaust system of the engine.

13. A control system as set forth in claim 12, wherein the communication with the exhaust system is to the exhaust port of the same combustion chamber.

14. A control system as set forth in claim 8, wherein the engine is a crankcase compression 2-cycle engine and the discharge is to a crankcase chamber.

15. A control system as set forth in claim 2, wherein the communication of the accumulator chamber with the combustion chamber is through a cylinder head of the engine.

16. A control system as set forth in claim 2, wherein the communication with the combustion chamber is through an exhaust system of the engine.

17. A control system as set forth in claim 16, wherein the engine is employed in combination with an outboard motor having a power head in which the engine is positioned and a guide plate beneath the engine and through which the exhaust gases flow.

18. A control system as set forth in claim 17, wherein the accumulator chamber is formed in the guide plate.

19. A control system as set forth in claim 18, wherein the accumulator chamber communicates with the exhaust passage through a restricted opening.

20. A control system as set forth in claim 18, wherein the accumulator chamber has a drain passage for returning condensed liquids to the exhaust system downstream of the first communication of the accumulator chamber to the exhaust system.

21. A control system as set forth in claim 5, wherein the exhaust gases from the accumulator chamber are returned to an induction system for the engine.

22. A control system as set forth in claim 1, wherein the protecting means comprises directing the inlet of the exhaust gases to the accumulator chamber away from the sensor.

23. A control system as set forth in claim 22, wherein the outlet of an inlet conduit that delivers the exhaust gases to the accumulator chamber is spaced from the sensor.

24. A control system as set forth in claim 23, further including an outlet conduit extending from the accumulator chamber for discharging the exhaust gases therefrom, said outlet conduit being spaced further from said sensor than the inlet conduit so that the exhaust gases flow away from the sensor from the inlet conduit to the outlet conduit.

25. A control system as set forth in claim 24, wherein both the inlet and outlet conduits extend into the interior of the accumulator chamber.

26. A control system as set forth in claim 25, wherein the outlet end of the inlet conduit and the inlet end of the outlet conduit are spaced apart a lesser distance from each other than the outlet conduit is spaced from the sensor.

27. A control system as set forth in claim 1, wherein the protecting means comprises a perforated sleeve surrounding the sensor.

28. A control system as set forth in claim 1, further including means for draining accumulated liquids from the accumulator chamber.

29. A control system as set forth in claim 1, wherein the protecting means comprises an orifice formed at the inlet of the exhaust gases to the accumulator chamber.

30. A control system as set forth in claim 29, wherein the orifice has a conical entrance through which the exhaust gases must enter the accumulator chamber.

31. A control system as set forth in claim 30, wherein the orifice further has a conical surface surrounding it on the side entering the accumulator chamber.

32. A control system as set forth in claim 1, wherein the sensor is provided in an accumulator chamber that communicates with the first accumulator chamber through a passageway so that the exhaust gases must flow through both accumulator chambers before contacting the sensor.

33. A control system as set forth in claim 32, wherein the communication between the two accumulator chambers is provided by a restricted orifice.

34. A control system as set forth in claim 33, wherein the restricted orifice communicating the accumulator chambers has a conical surface surrounding the inlet side of the orifice.

35. A control system as set forth in claim 32, wherein the exhaust gases flow through a serpentine path before exiting the accumulator chamber through an outlet conduit.

36. A control system as set forth in claim 35, wherein the serpentine path is formed downstream of the accumulator chamber.

37. A control system as set forth in claim 36, further including means for draining condensed liquids from the accumulator chamber.

38. A control system as set forth in claim 37, wherein the drain is through a restricted orifice.

39. A control system as set forth in claim 38, wherein the restricted orifice from the drain is formed with a conical surface surrounding its outlet side for restricting the backflow of gases to the accumulator chamber through the drain.

40. A control system as set forth in claim 35, wherein the serpentine path is formed in the first mentioned accumulator chamber.

41. A control system as set forth in claim 40, wherein there is further provided a serpentine path in the discharge of exhaust gases from the first mentioned accumulator chamber.

42. A control system as set forth in claim 41, further including means for draining condensed liquids from the accumulator chamber.

43. A control system as set forth in claim 42, wherein the drain is through a restricted orifice.

44. A control system as set forth in claim 40, wherein the serpentine path is provided by a first tube that enters the accumulator chamber and a second tube that discharges the accumulator chamber and the ends of the tubes are offset from each other.

45. A control system as set forth in claim 40, wherein the exhaust gases are delivered to the first accumulator chamber through a perforated tube.

46. A control system as set forth in claim 45, further including a drain area below the accumulator chamber wherein condensed liquids may be drained and accumulated.

47. A control system as set forth in claim 1, wherein the protecting means comprises means for maintaining a high temperature around the sensor so as to reduce the likelihood of liquids condensing on said sensor.

48. A control system as set forth in claim 47, wherein the means for maintaining the temperature of the sensor comprises means for insulating the accumulator chamber.

49. A control system as set forth in claim 48, wherein the insulation is provided on the outer housing of the accumulator chamber.

50. A control system as set forth in claim 47, wherein the means for maintaining the temperature of the sensor comprises a heater in the accumulator chamber and surrounding the sensor.

51. A control system as set forth in claim 50, wherein the means for maintaining the temperature of the sensor comprises means for insulating the accumulator chamber.

52. A control system as set forth in claim 51, wherein the insulation of the accumulator chamber is provided by an insulating medium on an outer housing of the accumulator chamber.

53. A control system as set forth in claim 47, wherein the means for maintaining the temperature of the sensor comprises means for insulating the connection of the exhaust conduit that delivers the exhaust gases to the accumulator chamber and the engine body from which the exhaust gases are drawn.

54. A control system as set forth in claim 47, wherein the means for maintaining the temperature of the sensor comprises insulating means interposed between the sensor and the housing that forms the accumulator chamber.

55. A control system for a 2-cycle, crankcase compression, internal combustion engine having a combustion chamber that varies in volume cyclically during engine operation, an exhaust system for receiving exhaust gases from said combustion chamber during a cycle of engine operation, a fuel supply system for supplying fuel to said engine for combustion in said combustion chamber, an accumulator chamber for providing a volume in which exhaust gases from said combustion chamber may accumulate and communicating with said combustion chamber for at least a portion of the engine operating cycle, a sensor in said accumulator chamber for providing a control signal for control of said fuel supply system, and protecting means for preventing oil and said exhaust gases from contaminating said sensor.

56. A control system as set forth in claim 55, wherein the protecting means comprises directing the inlet of the exhaust gases to the accumulator chamber away from the sensor.

57. A control system as set forth in claim 56, wherein the outlet of an inlet conduit that delivers the exhaust gases to the accumulator chamber is spaced from the sensor.

58. A control system as set forth in claim 57, further including an outlet conduit extending from the accumulator chamber for discharging the exhaust gases therefrom, said outlet conduit being spaced further from said sensor than the inlet conduit so that the exhaust gases flow away from the sensor from the inlet conduit to the outlet conduit.

59. A control system as set forth in claim 58, wherein both the inlet and outlet conduits extend into the interior of the accumulator chamber.

60. A control system as set forth in claim 59, wherein the outlet end of the inlet conduit and the inlet end of the outlet conduit are spaced apart a lesser distance from each other than the outlet conduit is spaced from the sensor.

61. A control system as set forth in claim 55, wherein the protecting means comprises a perforated sleeve surrounding the sensor.

62. A control system as set forth in claim 55, further including means for draining accumulated liquids from the accumulator chamber.

63. A control system as set forth in claim 55, wherein the protecting means comprises an orifice formed at the inlet of the exhaust gases to the accumulator chamber.

64. A control system as set forth in claim 63, wherein the orifice has a conical entrance through which the exhaust gases must enter the accumulator chamber.

65. A control system as set forth in claim 64, wherein the orifice further has a conical surface surrounding it on the side entering the accumulator chamber.

66. A control system as set forth in claim 55, wherein the sensor is provided in an accumulator chamber that communicates with the first accumulator chamber through a passageway so that the exhaust gases must flow through both accumulator chambers before contacting the sensor.

67. A control system as set forth in claim 66, wherein the communication between the two accumulator chambers is provided by a restricted orifice.

68. A control system as set forth in claim 67, wherein the restricted orifice communicating the accumulator chambers has a conical surface surrounding the inlet side of the orifice.

69. A control system as set forth in claim 66, wherein the exhaust gases flow through a serpentine path before exiting the accumulator chamber through an outlet conduit.

70. A control system as set forth in claim 69, wherein the serpentine path is formed downstream of the accumulator chamber.

71. A control system as set forth in claim 70, further including means for draining condensed liquids from the accumulator chamber.

72. A control system as set forth in claim 71, wherein the drain is through a restricted orifice.

73. A control system as set forth in claim 72, wherein the restricted orifice from the drain is formed with a conical surface surrounding its outlet side for restricting the backflow of gases to the accumulator chamber through the drain.

74. A control system as set forth in claim 69, wherein the serpentine path is formed in the first mentioned accumulator chamber.

75. A control system as set forth in claim 74, wherein there is further provided a serpentine path in the discharge of exhaust gases from the first mentioned accumulator chamber.

76. A control system as set forth in claim 71, further including means for draining condensed liquids from the accumulator chamber.

77. A control system as set forth in claim 76, wherein the drain is through a restricted orifice.

78. A control system as set forth in claim 74, wherein the serpentine path is provided by a first tube that enters the accumulator chamber and a second tube that discharges the accumulator chamber and the ends of the tubes are offset from each other.

79. A control system as set forth in claim 74, wherein the exhaust gases are delivered to the first accumulator chamber through a perforated tube.

80. A control system as set forth in claim 79, further including a drain area below the accumulator chamber wherein condensed liquids may be drained and accumulated.

81. A control system as set forth in claim 55, wherein the protecting means comprises means for maintaining a high temperature around the sensor so as to reduce the likelihood of liquids condensing on said sensor.

82. A control system as set forth in claim 81, wherein the means for maintaining the temperature of the sensor comprises means for insulating the accumulator chamber.

83. A control system as set forth in claim 82, wherein the insulation of the accumulator chamber is provided by an insulating medium on the outer housing of the accumulator chamber.

84. A control system as set forth in claim 81, wherein the means for maintaining the temperature of the sensor comprises a heater in the accumulator chamber and surrounding the sensor.

85. A control system as set forth in claim 84, wherein the means for maintaining the temperature of the sensor comprises means for insulating the accumulator chamber.

86. A control system as set forth in claim 83, wherein the insulation of the accumulator chamber is provided by an insulating medium on the outer housing of the accumulator chamber.

87. A control system as set forth in claim 81, wherein the means for maintaining the temperature of the sensor comprises means for insulating the connection of the exhaust conduit that delivers the exhaust gases to the accumulator chamber and the engine body from which the exhaust gases are drawn.

88. A control system as set forth in claim 81, wherein the means for maintaining the temperature of the sensor comprises insulating means interposed between the sensor and the housing that forms the accumulator chamber.

* * * * *